United States Patent [19]
Moore et al.

[11] Patent Number: 5,863,796
[45] Date of Patent: Jan. 26, 1999

[54] ANTIBODIES WHICH SPECIFICALLY BIND MAMMALIAN RECEPTORS FOR INTERLEUKIN-10 (IL-10)

[75] Inventors: Kevin W. Moore, Palo Alto; Ying Liu, Mountain View; Alice Suk-Yue Ho, Milpitas; Di-Hwei Hsu, Palo Alto; J. Fernando Bazan, Menlo Park, all of Calif.; Jimmy C. Tan, Edison; Chuan-Chu Chou, Westfield, both of N.J.

[73] Assignee: Schering Corporation, Kenilworth, N.J.

[21] Appl. No.: 477,166

[22] Filed: Jun. 7, 1995

Related U.S. Application Data

[60] Division of Ser. No. 110,683, Aug. 23, 1993, which is a continuation-in-part of Ser. No. 11,066, Jan. 29, 1993, abandoned, which is a continuation-in-part of Ser. No. 989,792, Dec. 10, 1992, abandoned.

[51] Int. Cl.$^6$ ............................. C07K 16/28; C12N 5/12; A61K 39/395; G01N 33/53
[52] U.S. Cl. ........................ 435/331; 435/334; 435/7.21; 424/139.1; 424/141.1; 424/143.1; 530/387.9; 530/388.22; 530/388.2; 530/388.85; 530/389.1; 530/389.6; 530/391.1; 530/391.3
[58] Field of Search .............................. 530/387.3, 387.9, 530/388.2, 389.1, 391.1, 391.3, 391.7, 388.22, 388.85, 389.6; 424/139, 141.1, 143.1; 435/331, 334, 7.21

[56] References Cited

PUBLICATIONS

C. -C. Chou, et al. "Interleukin–10 Receptor: Detection and Characterization on Human and Mouse Cell Lines," Abstract No. 350 *FASEB Journal* American Society of Biochemistry & Molecular Biology & Division of Biological Chemistry —American Chemical Society: Joint Meeting San Diego, CA May 30–Jun. 3, 1993.
David Cosman, "The Hematopoietin Receptor Superfamily," Cytokine, 5(2):95–106, 1993.
R.S. Kaczmarski, et al. "The Cytokine Receptor Superfamily," Blood Reviews, 5(3):193–203, 1991.
Jimmy C. Tan, et al. "Characterization of Interleukin–10 Receptors on Human and Mouse Cells," J. of Biol. Chem. 268(28):21053–21059, 1993.
J. Fernando Bazan, "Structural design and molecular evolution of a cytokine receptor superfamily," *PNAS*, vol. 87, pp. 6934–6938, Sep. 1990.
René de Waal Malefyt, et al., "Interleukin 10 (IL–10) Inhibits Cytokine Synthesis by Human Monocytes: An Autoregulatory Role of IL–10 Produced by Monocytes," *J. Exp. Med.*, vol. 174, pp. 1209–1220, Nov. 1991.
David F. Fiorentino, et al., "IL–10 Inhibits Cytokine Production By Activited Macrophages, "*J. Immunol.*, vol. 147, pp. 3815–3822, 1991.
David F. Fiorentino, et al., "Two Types Of Mouse T Helper Cell IV. Th2 Clones Secrete a Factor that Inhibits Cytokine Production by Th1 Clones," *J. Exp. Med.*, vol. 170, pp. 2081–2095, Dec. 1989.
David P. Gearing, et al., "Expression cloning of a rceptor for human granulocyte–marophage colony–stimulating factor," *The EMBO Journal*, vol. 8, No. 12, pp. 3667–3676, 1989.
Kazuhiro Hayashida, et al., "Molecular cloning of a second subunit of the receptor for human granulocyte–macrophage colony–stimulating factor (GM–CSF): Reconstitution of a high–affinity GM–CSF receptor," *PNAS*, vol. 87, pp. 9655–9659, Dec. 1990.
Di–Hwei Hsu, et al., "Differential effects of IL–4 and IL–10 on IL–2–induced IFN–γ synthesis and lymphokine–activated killer activity," *International Immunology*, vol. 4, No. 5, pp. 563–569, 1992.
Di–Hwei Hsu, et al., "Expression of Interleukin–10 Activity by Epstein–Barr Virus Protein BCFR1," *Science*, vol. 250, pp. 830–832, Nov. 1990.
Hiroshi Ishida, et al., "Continuous Anti–Interleukin 10 Antibody Administration Depletes Mice of Ly–1 B Cells but Not Conventional B Cells," *J. Exp. Med.*, vol. 175, pp. 1213–1220, May 1992.
Naoto Itoh, et al., "Cloning of an Interleukin–3 Receptor Gene: A Member of a Distinct Receptor Gene Family," *Science*, vol. 247, pp. 324–327, Jan. 1990.
Kevin W. Moore, et al., "Homology of Cytokine Synthesis Inhibitory Factor (IL–10) to the Epstein–Barr Virus Gene BCRFI," *Science*, vol. 248, pp. 1230–1234, Jun. 1990.
Tim R. Mosmann, et al., "The role of IL–10 in crossregulation of $T_h1$ and $T_h2$ resposes," *Immunology Today*, vol. 12, pp. A49–A53, 1991.
Stephen P. Squinto, et al., "Identification of Functional Receptors for Ciliary Neurotrophic Factor on Neuronal Cell Lines and Primary Neurons," *Neuron*, vol. 5, pp. 757–766, Dec. 1990.
Jan Tavernier, et al., "Human High Affinity Interleukin–5 Receptor (IL5R) Is Composed of an IL4–Specific α Chain and a β Chain Shared with the Receptor for GM–CSF," *Cell*, vol. 66, pp. 1175–1184, Sep. 20, 1991.
P. Vieira, et al., "Isolation and expression of human cytokine synthesis inhibitory factor cDNA clones: Homology to Epstein–Barr virus open reading frame BCRFI,"*PNAS*, vol. 88, pp. 1172–1176, Feb. 1991.
Liu, Y. J. Immunology 152:1821–1829, 1994.
Ho, A.S–Y, Therapeutic Immunology 1:173–185, 1994.

*Primary Examiner*—Toni R. Scheiner
*Assistant Examiner*—Nancy A. Johnson
*Attorney, Agent, or Firm*—Sheela Mohan-Peterson; Edwin P. Ching

[57] ABSTRACT

Receptor components for IL-10 are isolated and characterized. The amino acid sequence and nucleic acid encoding various species variants of the receptors are disclosed. Uses of the purified receptor gene and polypeptide are disclosed, including means for screening for agonists and antagonists of the receptor ligands, for producing diagnostic or therapeutic reagents, and for producing antibodies. Therapeutic or diagnostic reagents and kits are also provided.

25 Claims, 22 Drawing Sheets

MC9: mouse mast cells
J774: mouse macrophage

FACS was used to enrich for higher expression variants

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3632 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 62..1798

( x i ) SEQUENCE DESCRIPTION: SEQ ID NO:1:

```
AAAGAGCTGG  AGGCGCGCAG  GCCGGCTCCG  CTCCGGCCCC  GGACGATGCG  GCGCGCCCAG                60

G  ATG  CTG  CCG  TGC  CTC  GTA  GTG  CTG  CTG  GCG  GCG  CTC  CTC  AGC  CTC         106
   Met  Leu  Pro  Cys  Leu  Val  Val  Leu  Leu  Ala  Ala  Leu  Leu  Ser  Leu
   1                  5                           10                      15

CGT  CTT  GGC  TCA  GAC  GCT  CAT  GGG  ACA  GAG  CTG  CCC  AGC  CCT  CCG  TCT      154
Arg  Leu  Gly  Ser  Asp  Ala  His  Gly  Thr  Glu  Leu  Pro  Ser  Pro  Pro  Ser
                    20                      25                      30

GTG  TGG  TTT  GAA  GCA  GAA  TTT  TTC  CAC  CAC  ATC  CTC  CAC  TGG  ACA  CCC      202
Val  Trp  Phe  Glu  Ala  Glu  Phe  Phe  His  His  Ile  Leu  His  Trp  Thr  Pro
                35                          40                      45

ATC  CCA  AAT  CAG  TCT  GAA  AGT  ACC  TGC  TAT  GAA  GTG  GCG  CTC  CTG  AGG      250
Ile  Pro  Asn  Gln  Ser  Glu  Ser  Thr  Cys  Tyr  Glu  Val  Ala  Leu  Leu  Arg
            50                      55                      60

TAT  GGA  ATA  GAG  TCC  TGG  AAC  TCC  ATC  TCC  AAC  TGT  AGC  CAG  ACC  CTG      298
Tyr  Gly  Ile  Glu  Ser  Trp  Asn  Ser  Ile  Ser  Asn  Cys  Ser  Gln  Thr  Leu
```

-continued

|  |  |  |  |  |  |  |  |  |  |  |  |  |  |  |  |
|---|---|---|---|---|---|---|---|---|---|---|---|---|---|---|---|
| | | 65 | | | | | 70 | | | | | 75 | | | |
| TCC | TAT | GAC | CTT | ACC | GCA | GTG | ACC | TTG | GAC | CTG | TAC | CAC | AGC | AAT | GGC | 346
| Ser | Tyr | Asp | Leu | Thr | Ala | Val | Thr | Leu | Asp | Leu | Tyr | His | Ser | Asn | Gly |
| 80 | | | | | 85 | | | | | 90 | | | | | 95 |
| TAC | CGG | GCC | AGA | GTG | CGG | GCT | GTG | GAC | GGC | AGC | CGG | CAC | TCC | AAC | TGG | 394
| Tyr | Arg | Ala | Arg | Val | Arg | Ala | Val | Asp | Gly | Ser | Arg | His | Ser | Asn | Trp |
| | | | | 100 | | | | | 105 | | | | | 110 | |
| ACC | GTC | ACC | AAC | ACC | CGC | TTC | TCT | GTG | GAT | GAA | GTG | ACT | CTG | ACA | GTT | 442
| Thr | Val | Thr | Asn | Thr | Arg | Phe | Ser | Val | Asp | Glu | Val | Thr | Leu | Thr | Val |
| | | | 115 | | | | | 120 | | | | | 125 | | |
| GGC | AGT | GTG | AAC | CTA | GAG | ATC | CAC | AAT | GGC | TTC | ATC | CTC | GGG | AAG | ATT | 490
| Gly | Ser | Val | Asn | Leu | Glu | Ile | His | Asn | Gly | Phe | Ile | Leu | Gly | Lys | Ile |
| | | 130 | | | | | 135 | | | | | 140 | | | |
| CAG | CTA | CCC | AGG | CCC | AAG | ATG | GCC | CCC | GCG | AAT | GAC | ACA | TAT | GAA | AGC | 538
| Gln | Leu | Pro | Arg | Pro | Lys | Met | Ala | Pro | Ala | Asn | Asp | Thr | Tyr | Glu | Ser |
| | 145 | | | | | 150 | | | | | 155 | | | | |
| ATC | TTC | AGT | CAC | TTC | CGA | GAG | TAT | GAG | ATT | GCC | ATT | CGC | AAG | GTG | CCG | 586
| Ile | Phe | Ser | His | Phe | Arg | Glu | Tyr | Glu | Ile | Ala | Ile | Arg | Lys | Val | Pro |
| 160 | | | | | 165 | | | | | 170 | | | | | 175 |
| GGA | AAC | TTC | ACG | TTC | ACA | CAC | AAG | AAA | GTA | AAA | CAT | GAA | AAC | TTC | AGC | 634
| Gly | Asn | Phe | Thr | Phe | Thr | His | Lys | Lys | Val | Lys | His | Glu | Asn | Phe | Ser |
| | | | | 180 | | | | | 185 | | | | | 190 | |
| CTC | CTA | ACC | TCT | GGA | GAA | GTG | GGA | GAG | TTC | TGT | GTC | CAG | GTG | AAA | CCA | 682
| Leu | Leu | Thr | Ser | Gly | Glu | Val | Gly | Glu | Phe | Cys | Val | Gln | Val | Lys | Pro |
| | | | 195 | | | | | 200 | | | | | 205 | | |
| TCT | GTC | GCT | TCC | CGA | AGT | AAC | AAG | GGG | ATG | TGG | TCT | AAA | GAG | GAG | TGC | 730
| Ser | Val | Ala | Ser | Arg | Ser | Asn | Lys | Gly | Met | Trp | Ser | Lys | Glu | Glu | Cys |
| | | 210 | | | | | 215 | | | | | 220 | | | |
| ATC | TCC | CTC | ACC | AGG | CAG | TAT | TTC | ACC | GTG | ACC | AAC | GTC | ATC | ATC | TTC | 778
| Ile | Ser | Leu | Thr | Arg | Gln | Tyr | Phe | Thr | Val | Thr | Asn | Val | Ile | Ile | Phe |
| | 225 | | | | | 230 | | | | | 235 | | | | |
| TTT | GCC | TTT | GTC | CTG | CTG | CTC | TCC | GGA | GCC | CTC | GCC | TAC | TGC | CTG | GCC | 826
| Phe | Ala | Phe | Val | Leu | Leu | Leu | Ser | Gly | Ala | Leu | Ala | Tyr | Cys | Leu | Ala |
| 240 | | | | | 245 | | | | | 250 | | | | | 255 |
| CTC | CAG | CTG | TAT | GTG | CGG | CGC | CGA | AAG | AAG | CTA | CCC | AGT | GTC | CTG | CTC | 874
| Leu | Gln | Leu | Tyr | Val | Arg | Arg | Arg | Lys | Lys | Leu | Pro | Ser | Val | Leu | Leu |
| | | | | 260 | | | | | 265 | | | | | 270 | |
| TTC | AAG | AAG | CCC | AGC | CCC | TTC | ATC | TTC | ATC | AGC | CAG | CGT | CCC | TCC | CCA | 922
| Phe | Lys | Lys | Pro | Ser | Pro | Phe | Ile | Phe | Ile | Ser | Gln | Arg | Pro | Ser | Pro |
| | | | 275 | | | | | 280 | | | | | 285 | | |
| GAG | ACC | CAA | GAC | ACC | ATC | CAC | CCG | CTT | GAT | GAG | GAG | GCC | TTT | TTG | AAG | 970
| Glu | Thr | Gln | Asp | Thr | Ile | His | Pro | Leu | Asp | Glu | Glu | Ala | Phe | Leu | Lys |
| | | 290 | | | | | 295 | | | | | 300 | | | |
| GTG | TCC | CCA | GAG | CTG | AAG | AAC | TTG | GAC | CTG | CAC | GGC | AGC | ACA | GAC | AGT | 1018
| Val | Ser | Pro | Glu | Leu | Lys | Asn | Leu | Asp | Leu | His | Gly | Ser | Thr | Asp | Ser |
| | 305 | | | | | 310 | | | | | 315 | | | | |
| GGC | TTT | GGC | AGC | ACC | AAG | CCA | TCC | CTG | CAG | ACT | GAA | GAG | CCC | CAG | TTC | 1066
| Gly | Phe | Gly | Ser | Thr | Lys | Pro | Ser | Leu | Gln | Thr | Glu | Glu | Pro | Gln | Phe |
| 320 | | | | | 325 | | | | | 330 | | | | | 335 |
| CTC | CTC | CCT | GAC | CCT | CAC | CCC | CAG | GCT | GAC | AGA | ACG | CTG | GGA | AAC | GGG | 1114
| Leu | Leu | Pro | Asp | Pro | His | Pro | Gln | Ala | Asp | Arg | Thr | Leu | Gly | Asn | Gly |
| | | | | 340 | | | | | 345 | | | | | 350 | |
| GAG | CCC | CCT | GTG | CTG | GGG | GAC | AGC | TGC | AGT | AGT | GGC | AGC | AGC | AAT | AGC | 1162
| Glu | Pro | Pro | Val | Leu | Gly | Asp | Ser | Cys | Ser | Ser | Gly | Ser | Ser | Asn | Ser |
| | | | | 355 | | | | | 360 | | | | | 365 | |
| ACA | GAC | AGC | GGG | ATC | TGC | CTG | CAG | GAG | CCC | AGC | CTG | AGC | CCC | AGC | ACA | 1210
| Thr | Asp | Ser | Gly | Ile | Cys | Leu | Gln | Glu | Pro | Ser | Leu | Ser | Pro | Ser | Thr |
| | | | 370 | | | | | 375 | | | | | 380 | | |
| GGG | CCC | ACC | TGG | GAG | CAA | CAG | GTG | GGG | AGC | AAC | AGC | AGG | GGC | CAG | GAT | 1258
| Gly | Pro | Thr | Trp | Glu | Gln | Gln | Val | Gly | Ser | Asn | Ser | Arg | Gly | Gln | Asp |

-continued

```
            385                         390                         395
GAC AGT GGC ATT GAC TTA GTT CAA AAC TCT GAG GGC CGG GCT GGG GAC       1306
Asp Ser Gly Ile Asp Leu Val Gln Asn Ser Glu Gly Arg Ala Gly Asp
400                 405                 410                 415

ACA CAG GGT GGC TCG GCC TTG GGC CAC CAC AGT CCC CCG GAG CCT GAG       1354
Thr Gln Gly Gly Ser Ala Leu Gly His His Ser Pro Pro Glu Pro Glu
                420                 425                 430

GTG CCT GGG GAA GAA GAC CCA GCT GCT GTG GCA TTC CAG GGT TAC CTG       1402
Val Pro Gly Glu Glu Asp Pro Ala Ala Val Ala Phe Gln Gly Tyr Leu
            435                 440                 445

AGG CAG ACC AGA TGT GCT GAA GAG AAG GCA ACC AAG ACA GGC TGC CTG       1450
Arg Gln Thr Arg Cys Ala Glu Glu Lys Ala Thr Lys Thr Gly Cys Leu
    450                 455                 460

GAG GAA GAA TCG CCC TTG ACA GAT GGC CTT GGC CCC AAA TTC GGG AGA       1498
Glu Glu Glu Ser Pro Leu Thr Asp Gly Leu Gly Pro Lys Phe Gly Arg
465                 470                 475

TGC CTG GTT GAT GAG GCA GGC TTG CAT CCA CCA GCC CTG GCC AAG GGC       1546
Cys Leu Val Asp Glu Ala Gly Leu His Pro Pro Ala Leu Ala Lys Gly
480                 485                 490                 495

TAT TTG AAA CAG GAT CCT CTA GAA ATG ACT CTG GCT TCC TCA GGG GCC       1594
Tyr Leu Lys Gln Asp Pro Leu Glu Met Thr Leu Ala Ser Ser Gly Ala
                500                 505                 510

CCA ACG GGA CAG TGG AAC CAG CCC ACT GAG GAA TGG TCA CTC CTG GCC       1642
Pro Thr Gly Gln Trp Asn Gln Pro Thr Glu Glu Trp Ser Leu Leu Ala
            515                 520                 525

TTG AGC AGC TGC AGT GAC CTG GGA ATA TCT GAC TGG AGC TTT GCC CAT       1690
Leu Ser Ser Cys Ser Asp Leu Gly Ile Ser Asp Trp Ser Phe Ala His
        530                 535                 540

GAC CTT GCC CCT CTA GGC TGT GTG GCA GCC CCA GGT GGT CTC CTG GGC       1738
Asp Leu Ala Pro Leu Gly Cys Val Ala Ala Pro Gly Gly Leu Leu Gly
    545                 550                 555

AGC TTT AAC TCA GAC CTG GTC ACC CTG CCC CTC ATC TCT AGC CTG CAG       1786
Ser Phe Asn Ser Asp Leu Val Thr Leu Pro Leu Ile Ser Ser Leu Gln
560                 565                 570                 575

TCA AGT GAG TGACTCGGGC TGAGAGGCTG CTTTTGATTT TAGCCATGCC              1835
Ser Ser Glu

TGCTCCTCTG CCTGGACCAG GAGGAGGGCC CTGGGGCAGA AGTTAGGCAC GAGGCAGTCT    1895

GGGCACTTTT CTGCAAGTCC ACTGGGGCTG CCCAGCCAG GCTGCAGGGC TGGTCAGGGT    1955

GTCTGGGGCA GGAGGAGGCC AACTCACTGA ACTAGTGCAG GGTATGTGGG TGGCACTGAC   2015

CTGTTCTGTT GACTGGGGCC CTGCAGACTC TGGCAGAGCT GAGAAGGGCA GGGACCTTCT   2075

CCCTCCTAGG AACTCTTTCC TGTATCATAA AGGATTATTT GCTCAGGGGA ACCATGGGGC   2135

TTTCTGGAGT TGTGGTGAGG CCACCAGGCT GAAGTCAGCT CAGACCCAGA CCTCCCTGCT   2195

TAGGCCACTC GAGCATCAGA GCTTCCAGCA GGAGGAAGGG CTGTAGGAAT GGAAGCTTCA   2255

GGGCCTTGCT GCTGGGGTCA TTTTTAGGGG AAAAAGGAGG ATATGATGGT CACATGGGGA   2315

ACCTCCCCTC ATCGGGCCTC TGGGGCAGGA AGCTTGTCAC TGGAAGATCT TAAGGTATAT   2375

ATTTTCTGGA CACTCAAACA CATCATAATG GATTCACTGA GGGGAGACAA AGGGAGCCGA   2435

GACCCTGGAT GGGGCTTCCA GCTCAGAACC CATCCCTCTG GTGGGTACCT CTGGCACCCA   2495

TCTGCAAATA TCTCCCTCTC TCCAACAAAT GGAGTAGCAT CCCCCTGGGG CACTTGCTGA   2555

GGCCAAGCCA CTCACATCCT CACTTTGCTG CCCCACCATC TTGCTGACAA CTTCCAGAGA   2615

AGCCATGGTT TTTTGTATTG GTCATAACTC AGCCCTTTGG GCGGCCTCTG GCTTGGGCA    2675

CCAGCTCATG CCAGCCCCAG AGGGTCAGGG TTGGAGGCCT GTGCTTGTGT TTGCTGCTAA   2735

TGTCCAGCTA CAGACCCAGA GGATAAGCCA CTGGGCACTG GCTGGGGTC CCTGCCTTGT    2795
```

| | | | | | |
|---|---|---|---|---|---|
| TGGTGTTCAG | CTGTGTGATT | TTGGACTAGC | CACTTGTCAG | AGGGCCTCAA | TCTCCCATCT | 2855 |
| GTGAAATAAG | GACTCCACCT | TTAGGGGACC | CTCCATGTTT | GCTGGGTATT | AGCCAAGCTG | 2915 |
| GTCCTGGGAG | AATGCAGATA | CTGTCCGTGG | ACTACCAAGC | TGGCTTGTTT | CTTATGCCAG | 2975 |
| AGGCTAACAG | ATCCAATGGG | AGTCCATGGT | GTCATGCCAA | GACAGTATCA | GACACAGCCC | 3035 |
| CAGAAGGGGG | CATTATGGGC | CCTGCCTCCC | CATAGGCCAT | TTGGACTCTG | CCTTCAAACA | 3095 |
| AAGGCAGTTC | AGTCCACAGG | CATGGAAGCT | GTGAGGGAC | AGGCCTGTGC | GTGCCATCCA | 3155 |
| GAGTCATCTC | AGCCCTGCCT | TTCTCTGGAG | CATTCTGAAA | ACAGATATTC | TGGCCCAGGG | 3215 |
| AATCCAGCCA | TGACCCCCAC | CCCTCTGCCA | AAGTACTCTT | AGGTGCCAGT | CTGGTAACTG | 3275 |
| AACTCCCTCT | GGAGGCAGGC | TTGAGGGAGG | ATTCCTCAGG | GTTCCCTTGA | AAGCTTTATT | 3335 |
| TATTTATTTT | GTTCATTTAT | TTATTGGAGA | GGCAGCATTG | CACAGTGAAA | GAATTCTGGA | 3395 |
| TATCTCAGGA | GCCCCGAAAT | TCTAGCTCTG | ACTTTGCTGT | TTCCAGTGGT | ATGACCTTGG | 3455 |
| AGAAGTCACT | TATCCTCTTG | GAGCCTCAGT | TTCCTCATCT | GCAGAATAAT | GACTGACTTG | 3515 |
| TCTAATTCAT | AGGGATGTGA | GGTTCTGCTG | AGGAAATGGG | TATGAATGTG | CCTTGAACAC | 3575 |
| AAAGCTCTGT | CAATAAGTGA | TACATGTTTT | TTATTCCAAT | AAATTGTCAA | GACCACA | 3632 |

( 2 ) INFORMATION FOR SEQ ID NO:2:

( i ) SEQUENCE CHARACTERISTICS:
      ( A ) LENGTH: 578 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

| Met | Leu | Pro | Cys | Leu | Val | Val | Leu | Leu | Ala | Ala | Leu | Leu | Ser | Leu | Arg |
|---|---|---|---|---|---|---|---|---|---|---|---|---|---|---|---|
| 1 | | | | 5 | | | | | 10 | | | | | 15 | |
| Leu | Gly | Ser | Asp | Ala | His | Gly | Thr | Glu | Leu | Pro | Ser | Pro | Pro | Ser | Val |
| | | | 20 | | | | | 25 | | | | | 30 | | |
| Trp | Phe | Glu | Ala | Glu | Phe | Phe | His | His | Ile | Leu | His | Trp | Thr | Pro | Ile |
| | | | 35 | | | | | 40 | | | | | 45 | | |
| Pro | Asn | Gln | Ser | Glu | Ser | Thr | Cys | Tyr | Glu | Val | Ala | Leu | Leu | Arg | Tyr |
| | | 50 | | | | | 55 | | | | | 60 | | | |
| Gly | Ile | Glu | Ser | Trp | Asn | Ser | Ile | Ser | Asn | Cys | Ser | Gln | Thr | Leu | Ser |
| 65 | | | | | 70 | | | | | 75 | | | | | 80 |
| Tyr | Asp | Leu | Thr | Ala | Val | Thr | Leu | Asp | Leu | Tyr | His | Ser | Asn | Gly | Tyr |
| | | | | 85 | | | | | 90 | | | | | 95 | |
| Arg | Ala | Arg | Val | Arg | Ala | Val | Asp | Gly | Ser | Arg | His | Ser | Asn | Trp | Thr |
| | | | | 100 | | | | | 105 | | | | | 110 | |
| Val | Thr | Asn | Thr | Arg | Phe | Ser | Val | Asp | Glu | Val | Thr | Leu | Thr | Val | Gly |
| | | | 115 | | | | | 120 | | | | | 125 | | |
| Ser | Val | Asn | Leu | Glu | Ile | His | Asn | Gly | Phe | Ile | Leu | Gly | Lys | Ile | Gln |
| | 130 | | | | | 135 | | | | | 140 | | | | |
| Leu | Pro | Arg | Pro | Lys | Met | Ala | Pro | Ala | Asn | Asp | Thr | Tyr | Glu | Ser | Ile |
| 145 | | | | | 150 | | | | | 155 | | | | | 160 |
| Phe | Ser | His | Phe | Arg | Glu | Tyr | Glu | Ile | Ala | Ile | Arg | Lys | Val | Pro | Gly |
| | | | | 165 | | | | | 170 | | | | | 175 | |
| Asn | Phe | Thr | Phe | Thr | His | Lys | Lys | Val | Lys | His | Glu | Asn | Phe | Ser | Leu |
| | | | 180 | | | | | 185 | | | | | 190 | | |
| Leu | Thr | Ser | Gly | Glu | Val | Gly | Glu | Phe | Cys | Val | Gln | Val | Lys | Pro | Ser |
| | | 195 | | | | | 200 | | | | | 205 | | | |

| | | | | | | | | | | | | | | |
|---|---|---|---|---|---|---|---|---|---|---|---|---|---|---|
| Val | Ala | Ser | Arg | Ser | Asn | Lys | Gly | Met | Trp | Ser | Lys | Glu | Glu | Cys | Ile |
| | 210 | | | | 215 | | | | | 220 | | | | |
| Ser | Leu | Thr | Arg | Gln | Tyr | Phe | Thr | Val | Thr | Asn | Val | Ile | Ile | Phe | Phe |
| 225 | | | | | 230 | | | | | 235 | | | | | 240 |
| Ala | Phe | Val | Leu | Leu | Leu | Ser | Gly | Ala | Ala | Tyr | Cys | Leu | Ala | Leu |
| | | | | 245 | | | | | 250 | | | | 255 | |
| Gln | Leu | Tyr | Val | Arg | Arg | Arg | Lys | Lys | Leu | Pro | Ser | Val | Leu | Leu | Phe |
| | | | 260 | | | | | 265 | | | | | 270 | | |
| Lys | Lys | Pro | Ser | Pro | Phe | Ile | Phe | Ile | Ser | Gln | Arg | Pro | Ser | Pro | Glu |
| | | 275 | | | | | 280 | | | | | 285 | | | |
| Thr | Gln | Asp | Thr | Ile | His | Pro | Leu | Asp | Glu | Glu | Ala | Phe | Leu | Lys | Val |
| | 290 | | | | | 295 | | | | | 300 | | | | |
| Ser | Pro | Glu | Leu | Lys | Asn | Leu | Asp | Leu | His | Gly | Ser | Thr | Asp | Ser | Gly |
| 305 | | | | | 310 | | | | | 315 | | | | | 320 |
| Phe | Gly | Ser | Thr | Lys | Pro | Ser | Leu | Gln | Thr | Glu | Glu | Pro | Gln | Phe | Leu |
| | | | | 325 | | | | | 330 | | | | | 335 | |
| Leu | Pro | Asp | Pro | His | Pro | Gln | Ala | Asp | Arg | Thr | Leu | Gly | Asn | Gly | Glu |
| | | | 340 | | | | | 345 | | | | | 350 | | |
| Pro | Pro | Val | Leu | Gly | Asp | Ser | Cys | Ser | Ser | Gly | Ser | Ser | Asn | Ser | Thr |
| | | 355 | | | | | 360 | | | | | 365 | | | |
| Asp | Ser | Gly | Ile | Cys | Leu | Gln | Glu | Pro | Ser | Leu | Ser | Pro | Ser | Thr | Gly |
| 370 | | | | | 375 | | | | | 380 | | | | | |
| Pro | Thr | Trp | Glu | Gln | Gln | Val | Gly | Ser | Asn | Ser | Arg | Gly | Gln | Asp | Asp |
| 385 | | | | | 390 | | | | | 395 | | | | | 400 |
| Ser | Gly | Ile | Asp | Leu | Val | Gln | Asn | Ser | Glu | Gly | Arg | Ala | Gly | Asp | Thr |
| | | | | 405 | | | | | 410 | | | | | 415 | |
| Gln | Gly | Gly | Ser | Ala | Leu | Gly | His | His | Ser | Pro | Pro | Glu | Pro | Glu | Val |
| | | | 420 | | | | | 425 | | | | | 430 | | |
| Pro | Gly | Glu | Glu | Asp | Pro | Ala | Ala | Val | Ala | Phe | Gln | Gly | Tyr | Leu | Arg |
| | | 435 | | | | | 440 | | | | | 445 | | | |
| Gln | Thr | Arg | Cys | Ala | Glu | Glu | Lys | Ala | Thr | Lys | Thr | Gly | Cys | Leu | Glu |
| | 450 | | | | | 455 | | | | | 460 | | | | |
| Glu | Glu | Ser | Pro | Leu | Thr | Asp | Gly | Leu | Gly | Pro | Lys | Phe | Gly | Arg | Cys |
| 465 | | | | | 470 | | | | | 475 | | | | | 480 |
| Leu | Val | Asp | Glu | Ala | Gly | Leu | His | Pro | Pro | Ala | Leu | Ala | Lys | Gly | Tyr |
| | | | | 485 | | | | | 490 | | | | | 495 | |
| Leu | Lys | Gln | Asp | Pro | Leu | Glu | Met | Thr | Leu | Ala | Ser | Ser | Gly | Ala | Pro |
| | | | 500 | | | | | 505 | | | | | 510 | | |
| Thr | Gly | Gln | Trp | Asn | Gln | Pro | Thr | Glu | Glu | Trp | Ser | Leu | Leu | Ala | Leu |
| | | 515 | | | | | 520 | | | | | 525 | | | |
| Ser | Ser | Cys | Ser | Asp | Leu | Gly | Ile | Ser | Asp | Trp | Ser | Phe | Ala | His | Asp |
| | 530 | | | | | 535 | | | | | 540 | | | | |
| Leu | Ala | Pro | Leu | Gly | Cys | Val | Ala | Ala | Pro | Gly | Gly | Leu | Leu | Gly | Ser |
| 545 | | | | | 550 | | | | | 555 | | | | | 560 |
| Phe | Asn | Ser | Asp | Leu | Val | Thr | Leu | Pro | Leu | Ile | Ser | Ser | Leu | Gln | Ser |
| | | | | 565 | | | | | 570 | | | | | 575 | |
| Ser | Glu | | | | | | | | | | | | | | |

( 2 ) INFORMATION FOR SEQ ID NO:3:

( i ) SEQUENCE CHARACTERISTICS:
( A ) LENGTH: 3520 base pairs
( B ) TYPE: nucleic acid
( C ) STRANDEDNESS: single
( D ) TOPOLOGY: linear (  i i  ) MOLECULE TYPE: cDNA (  i x  ) FEATURE:
    ( A ) NAME/KEY: CDS
    ( B ) LOCATION: 80..1807

(  x i  ) SEQUENCE DESCRIPTION: SEQ ID NO:3:

```
CCATTGTGCT GGAAAGCAGG ACGCGCCGGC CGGAGGCGTA AAGGCCGGCT CCAGTGGACG                    60

ATGCCGCTGT GCGCCCAGG ATG TTG TCG CGT TTG CTC CCA TTC CTC GTC ACG                    112
                    Met Leu Ser Arg Leu Leu Pro Phe Leu Val Thr
                     1               5                      10

ATC TCC AGC CTG AGC CTA GAA TTC ATT GCA TAC GGG ACA GAA CTG CCA                     160
Ile Ser Ser Leu Ser Leu Glu Phe Ile Ala Tyr Gly Thr Glu Leu Pro
             15                  20                  25

AGC CCT TCC TAT GTG TGG TTT GAA GCC AGA TTT TTC CAG CAC ATC CTC                     208
Ser Pro Ser Tyr Val Trp Phe Glu Ala Arg Phe Phe Gln His Ile Leu
         30                  35                  40

CAC TGG AAA CCT ATC CCA AAC CAG TCT GAG AGC ACC TAC TAT GAA GTG                     256
His Trp Lys Pro Ile Pro Asn Gln Ser Glu Ser Thr Tyr Tyr Glu Val
     45                  50                  55

GCC CTC AAA CAG TAC GGA AAC TCA ACC TGG AAT GAC ATC CAT ATC TGT                     304
Ala Leu Lys Gln Tyr Gly Asn Ser Thr Trp Asn Asp Ile His Ile Cys
 60                  65                  70                  75

AGA AAG GCT CAG GCA TTG TCC TGT GAT CTC ACA ACG TTC ACC CTG GAT                     352
Arg Lys Ala Gln Ala Leu Ser Cys Asp Leu Thr Thr Phe Thr Leu Asp
                 80                  85                  90

CTG TAT CAC CGA AGC TAT GGC TAC CGG GCC AGA GTC CGG GCA GTG GAC                     400
Leu Tyr His Arg Ser Tyr Gly Tyr Arg Ala Arg Val Arg Ala Val Asp
             95                 100                 105

AAC AGT CAG TAC TCC AAC TGG ACC ACC ACT GAG ACT CGC TTC ACA GTG                     448
Asn Ser Gln Tyr Ser Asn Trp Thr Thr Thr Glu Thr Arg Phe Thr Val
        110                 115                 120

GAT GAA GTG ATT CTG ACA GTG GAT AGC GTG ACT CTG AAA GCA ATG GAC                     496
Asp Glu Val Ile Leu Thr Val Asp Ser Val Thr Leu Lys Ala Met Asp
    125                 130                 135

GGC ATC ATC TAT GGG ACA ATC CAT CCC CCC AGG CCC ACG ATA ACC CCT                     544
Gly Ile Ile Tyr Gly Thr Ile His Pro Pro Arg Pro Thr Ile Thr Pro
140                 145                 150                 155

GCA GGG GAT GAG TAC GAA CAA GTC TTC AAG GAT CTC CGA GTT TAC AAG                     592
Ala Gly Asp Glu Tyr Glu Gln Val Phe Lys Asp Leu Arg Val Tyr Lys
                160                 165                 170

ATT TCC ATC CGG AAG TTC TCA GAA CTA AAG AAT GCA ACC AAG AGA GTG                     640
Ile Ser Ile Arg Lys Phe Ser Glu Leu Lys Asn Ala Thr Lys Arg Val
            175                 180                 185

AAA CAG GAA ACC TTC ACC CTC ACG GTC CCC ATA GGG GTG AGA AAG TTT                     688
Lys Gln Glu Thr Phe Thr Leu Thr Val Pro Ile Gly Val Arg Lys Phe
        190                 195                 200

TGT GTC AAG GTG CTG CCC CGC TTG GAA TCC CGA ATT AAC AAG GCA GAG                     736
Cys Val Lys Val Leu Pro Arg Leu Glu Ser Arg Ile Asn Lys Ala Glu
    205                 210                 215

TGG TCG GAG GAG CAG TGT TTA CTT ATC ACG ACG GAG CAG TAT TTC ACT                     784
Trp Ser Glu Glu Gln Cys Leu Leu Ile Thr Thr Glu Gln Tyr Phe Thr
220                 225                 230                 235

GTG ACC AAC CTG AGC ATC TTA GTC ATA TCT ATG CTG CTA TTC TGT GGA                     832
Val Thr Asn Leu Ser Ile Leu Val Ile Ser Met Leu Leu Phe Cys Gly
                240                 245                 250

ATC CTG GTC TGT CTG GTT CTC CAG TGG TAC ATC CGG CAC CCG GGG AAG                     880
Ile Leu Val Cys Leu Val Leu Gln Trp Tyr Ile Arg His Pro Gly Lys
            255                 260                 265

TTG CCT ACA GTC CTG GTC TTC AAG AAG CCT CAC GAC TTC TTC CCA GCC                     928
Leu Pro Thr Val Leu Val Phe Lys Lys Pro His Asp Phe Phe Pro Ala
```

```
                    270                        275                        280
AAC  CCT  CTC  TGC  CCA  GAA  ACT  CCC  GAT  GCC  ATT  CAC  ATC  GTG  GAC  CTG        976
Asn  Pro  Leu  Cys  Pro  Glu  Thr  Pro  Asp  Ala  Ile  His  Ile  Val  Asp  Leu
     285                      290                     295

GAG  GTT  TTC  CCA  AAG  GTG  TCA  CTA  GAG  CTG  AGA  GAC  TCA  GTC  CTG  CAT       1024
Glu  Val  Phe  Pro  Lys  Val  Ser  Leu  Glu  Leu  Arg  Asp  Ser  Val  Leu  His
300                           305                     310                      315

GGC  AGC  ACC  GAC  AGT  GGC  TTT  GGC  AGT  GGT  AAA  CCA  TCA  CTT  CAG  ACT       1072
Gly  Ser  Thr  Asp  Ser  Gly  Phe  Gly  Ser  Gly  Lys  Pro  Ser  Leu  Gln  Thr
               320                     325                           330

GAA  GAG  TCC  CAA  TTC  CTC  CTC  CCT  GGC  TCC  CAC  CCC  CAG  ATA  CAG  GGG       1120
Glu  Glu  Ser  Gln  Phe  Leu  Leu  Pro  Gly  Ser  His  Pro  Gln  Ile  Gln  Gly
               335                     340                      345

ACT  CTG  GGA  AAA  GAA  GAG  TCT  CCA  GGG  CTA  CAG  GCC  ACC  TGT  GGG  GAC       1168
Thr  Leu  Gly  Lys  Glu  Glu  Ser  Pro  Gly  Leu  Gln  Ala  Thr  Cys  Gly  Asp
          350                     355                           360

AAC  ACG  GAC  AGT  GGG  ATC  TGC  CTG  CAG  GAG  CCC  GGC  TTA  CAC  TCC  AGC       1216
Asn  Thr  Asp  Ser  Gly  Ile  Cys  Leu  Gln  Glu  Pro  Gly  Leu  His  Ser  Ser
     365                      370                           375

ATG  GGG  CCC  GCC  TGG  AAG  CAG  CAG  CTT  GGA  TAT  ACC  CAT  CAG  GAC  CAG       1264
Met  Gly  Pro  Ala  Trp  Lys  Gln  Gln  Leu  Gly  Tyr  Thr  His  Gln  Asp  Gln
380                           385                     390                      395

GAT  GAC  AGT  GAC  GTT  AAC  CTA  GTC  CAG  AAC  TCT  CCA  GGG  CAG  CCT  AAG       1312
Asp  Asp  Ser  Asp  Val  Asn  Leu  Val  Gln  Asn  Ser  Pro  Gly  Gln  Pro  Lys
               400                     405                           410

TAC  ACA  CAG  GAT  GCA  TCT  GCC  TTG  GGC  CAT  GTC  TGT  CTC  CTA  GAA  CCT       1360
Tyr  Thr  Gln  Asp  Ala  Ser  Ala  Leu  Gly  His  Val  Cys  Leu  Leu  Glu  Pro
               415                     420                           425

AAA  GCC  CCT  GAG  GAG  AAA  GAC  CAA  GTC  ATG  GTG  ACA  TTC  CAG  GGC  TAC       1408
Lys  Ala  Pro  Glu  Glu  Lys  Asp  Gln  Val  Met  Val  Thr  Phe  Gln  Gly  Tyr
          430                     435                           440

CAG  AAA  CAG  ACC  AGA  TGG  AAG  GCA  GAG  GCA  GCA  GGC  CCA  GCA  GAA  TGC       1456
Gln  Lys  Gln  Thr  Arg  Trp  Lys  Ala  Glu  Ala  Ala  Gly  Pro  Ala  Glu  Cys
     445                      450                           455

TTG  GAC  GAA  GAG  ATT  CCC  TTG  ACA  GAT  GCC  TTT  GAT  CCT  GAA  CTT  GGG       1504
Leu  Asp  Glu  Glu  Ile  Pro  Leu  Thr  Asp  Ala  Phe  Asp  Pro  Glu  Leu  Gly
460                           465                     470                      475

GTA  CAC  CTG  CAG  GAT  GAT  TTG  GCT  TGG  CCT  CCA  CCA  GCT  CTG  GCC  GCA       1552
Val  His  Leu  Gln  Asp  Asp  Leu  Ala  Trp  Pro  Pro  Pro  Ala  Leu  Ala  Ala
               480                     485                           490

GGT  TAT  TTG  AAA  CAG  GAG  TCT  CAA  GGG  ATG  GCT  TCT  GCT  CCA  CCA  GGG       1600
Gly  Tyr  Leu  Lys  Gln  Glu  Ser  Gln  Gly  Met  Ala  Ser  Ala  Pro  Pro  Gly
               495                     500                           505

ACA  CCA  AGT  AGA  CAG  TGG  AAT  CAA  CTG  ACC  GAA  GAG  TGG  TCA  CTC  CTG       1648
Thr  Pro  Ser  Arg  Gln  Trp  Asn  Gln  Leu  Thr  Glu  Glu  Trp  Ser  Leu  Leu
          510                     515                           520

GGT  GTG  GTT  AGC  TGT  GAA  GAT  CTA  AGC  ATA  GAA  AGT  TGG  AGG  TTT  GCC       1696
Gly  Val  Val  Ser  Cys  Glu  Asp  Leu  Ser  Ile  Glu  Ser  Trp  Arg  Phe  Ala
     525                      530                           535

CAT  AAA  CTT  GAC  CCT  CTG  GAC  TGT  GGG  GCA  GCC  CCT  GGT  GGC  CTC  CTG       1744
His  Lys  Leu  Asp  Pro  Leu  Asp  Cys  Gly  Ala  Ala  Pro  Gly  Gly  Leu  Leu
540                           545                     550                      555

GAT  AGC  CTT  GGC  TCT  AAC  CTG  GTC  ACC  CTG  CCG  TTG  ATC  TCC  AGC  CTG       1792
Asp  Ser  Leu  Gly  Ser  Asn  Leu  Val  Thr  Leu  Pro  Leu  Ile  Ser  Ser  Leu
               560                     565                           570

CAG  GTA  GAA  GAA  TGACAGCGGC TAAGAGTTAT TTGTATTCCA GCCATGCCTG                     1844
Gln  Val  Glu  Glu
               575

CTCCCCTCCC TGTACCTGGG AGGCTCAGGA GTCAAAGAAA TATGTGGGTC CTTTTCTGCA                   1904
```

```
GACCTACTGT  GACCAGCTAG  CCAGGCTCCA  CGGGGCAAGG  AAAGGCCATC  TTGATACACG   1964

AGTGTCAGGT  ACATGAGAGG  TTGTGGCTAG  TCTGCTGAGT  GAGGGTCTGT  AGATACCAGC   2024

AGAGCTGAGC  AGGATTGACA  GAGACCTCCT  CATGCCTCAG  GGCTGGCTCC  TACACTGGAA   2084

GGACCTGTGT  TTGGGTGTAA  CCTCAGGGCT  TTCTGGATGT  GGTAAGACTG  TAGGTCTGAA   2144

GTCAGCTGAG  CCTGGATGTC  TGCGGAGGTG  TTGGAGTGGC  TAGCCTGCTA  CAGGATAAAG   2204

GGAAGGCTCA  AGAGATAGAA  GGGCAGAGCA  TGAGCCAGGT  TTAATTTTGT  CCTGTAGAGA   2264

TGGTCCCCAG  CCAGGATGGG  TTACTTGTGG  CTGGGAGATC  TTGGGGTATA  CACCACCCTG   2324

AATGATCAGC  CAGTCAATTC  AGAGCTGTGT  GGCAAAAGGG  ACTGAGACCC  AGAATTTCTG   2384

TTCCTCTTGT  GAGGTGTCTC  TGCTACCCAT  CTGCAGACAG  ACATCTTCAT  CTTTTACTA    2444

TGGCTGTGTC  CCCTGAATTA  CCAGCAGTGG  CCAAGCCATT  ACTCCTGCT   GCTCACTGTT   2504

GTGACGTCAG  ACCAGACCAG  ACGCTGTCTG  TCTGTGTTAG  TACACTACCC  TTAGGTGGC    2564

CTTTGGGCTT  GAGCACTGGC  CCAGGCTTAG  GACTTATGTC  TGCTTTTGCT  GCTAATCTCT   2624

AACTGCAGAC  CCAGAGAACA  GGGTGCTGGG  CTGACACCTC  CGTGTTCAGC  TGTGTGACCT   2684

CCGACCAGCA  GCTTCCTCAG  GGGACTAAAA  TAATGACTAG  GTCATTCAGA  AGTCCCTCAT   2744

GCTGAATGTT  AACCAAGGTG  CCCCTGGGGT  GATAGTTTAG  GTCCTGCAAC  CTCTGGGTTG   2804

GAAGGAAGTG  GACTACGGAA  GCCATCTGTC  CCCCTGGGGA  GCTTCCACCT  CATGCCAGTG   2864

TTTCAGAGAT  CTTGTGGGAG  CCTAGGGCCT  TGTGCCAAGG  GAGCTGCTAG  TCCCTGGGGT   2924

CTAGGGCTGG  TCCCTGCCTC  CCTATACTGC  GTTTGAGACC  TGTCTTCAAA  TGGAGGCAGT   2984

TTGCAGCCCC  TAAGCAAGGA  TGCTGAGAGA  AGCAGCAAGG  CTGCTGATCC  CTGAGCCCAG   3044

AGTTTCTCTG  AAGCTTTCCA  AATACAGACT  GTGTGACGGG  GTGAGGCCAG  CCATGAACTT   3104

TGGCATCCTG  CCGAGAAGGT  CATGACCCTA  ATCTGGTACG  AGAGCTCCTT  CTGGAACTGG   3164

GCAAGCTCTT  TGAGACCCCC  CTGGAACCTT  TATTTATTTA  TTTGCTCACT  TATTTATTGA   3224

GGAAGCAGCG  TGGCACAGGC  GCAAGGCTCT  GGGTCTCTCA  GGAGGTCTAG  ATTTGCCTGC   3284

CCTGTTTCTA  GCTGTGTGAC  CTTGGGCAAG  TCACGTTTCC  TCGTGGAGCC  TCAGTTTTCC   3344

TGTCTGTATG  CAAAGCTTGG  AAATTGAAAT  GTACCTGACG  TGCTCCATCC  CTAGGAGTGC   3404

TGAGTCCCAC  TGAGAAAGCG  GGCACAGACG  CCTCAAATGG  AACCACAAGT  GGTGTGTGTT   3464

TTCATCCTAA  TAAAAAGTCA  GGTGTTTTGT  GGAAAAAAAA  AAAAAAAAAA  AAAAAA       3520
```

(2) INFORMATION FOR SEQ ID NO:4:

(i) SEQUENCE CHARACTERISTICS:
        (A) LENGTH: 575 amino acids
        (B) TYPE: amino acid
        (D) TOPOLOGY: linear (ii) MOLECULE TYPE: protein (xi) SEQUENCE DESCRIPTION: SEQ ID NO:4:

```
Met  Leu  Ser  Arg  Leu  Leu  Pro  Phe  Leu  Val  Thr  Ile  Ser  Ser  Leu  Ser
 1                  5                   10                      15

Leu  Glu  Phe  Ile  Ala  Tyr  Gly  Thr  Glu  Leu  Pro  Ser  Pro  Ser  Tyr  Val
             20                      25                  30

Trp  Phe  Glu  Ala  Arg  Phe  Phe  Gln  His  Ile  Leu  His  Trp  Lys  Pro  Ile
         35                      40                      45

Pro  Asn  Gln  Ser  Glu  Ser  Thr  Tyr  Tyr  Glu  Val  Ala  Leu  Lys  Gln  Tyr
        50                      55                      60

Gly  Asn  Ser  Thr  Trp  Asn  Asp  Ile  His  Ile  Cys  Arg  Lys  Ala  Gln  Ala
65                       70                      75                       80
```

| | | | | | | | | | | | | | | |
|---|---|---|---|---|---|---|---|---|---|---|---|---|---|---|
| Leu | Ser | Cys | Asp | Leu<br>85 | Thr | Thr | Phe | Thr | Leu<br>90 | Asp | Leu | Tyr | His | Arg<br>95 | Ser |
| Tyr | Gly | Tyr | Arg<br>100 | Ala | Arg | Val | Arg | Ala<br>105 | Val | Asp | Asn | Ser | Gln<br>110 | Tyr | Ser |
| Asn | Trp | Thr<br>115 | Thr | Thr | Glu | Thr | Arg<br>120 | Phe | Thr | Val | Asp | Glu<br>125 | Val | Ile | Leu |
| Thr | Val<br>130 | Asp | Ser | Val | Thr | Leu<br>135 | Lys | Ala | Met | Asp | Gly<br>140 | Ile | Ile | Tyr | Gly |
| Thr<br>145 | Ile | His | Pro | Pro | Arg<br>150 | Pro | Thr | Ile | Thr | Pro<br>155 | Ala | Gly | Asp | Glu | Tyr<br>160 |
| Glu | Gln | Val | Phe | Lys<br>165 | Asp | Leu | Arg | Val | Tyr<br>170 | Lys | Ile | Ser | Ile | Arg<br>175 | Lys |
| Phe | Ser | Glu | Leu<br>180 | Lys | Asn | Ala | Thr | Lys<br>185 | Arg | Val | Lys | Gln | Glu<br>190 | Thr | Phe |
| Thr | Leu | Thr<br>195 | Val | Pro | Ile | Gly | Val<br>200 | Arg | Lys | Phe | Cys | Val<br>205 | Lys | Val | Leu |
| Pro | Arg<br>210 | Leu | Glu | Ser | Arg | Ile<br>215 | Asn | Lys | Ala | Glu | Trp<br>220 | Ser | Glu | Glu | Gln |
| Cys<br>225 | Leu | Leu | Ile | Thr | Thr<br>230 | Glu | Gln | Tyr | Phe | Thr<br>235 | Val | Thr | Asn | Leu | Ser<br>240 |
| Ile | Leu | Val | Ile | Ser<br>245 | Met | Leu | Leu | Phe | Cys<br>250 | Gly | Ile | Leu | Val | Cys<br>255 | Leu |
| Val | Leu | Gln | Trp | Tyr<br>260 | Ile | Arg | His | Pro | Gly<br>265 | Lys | Leu | Pro | Thr<br>270 | Val | Leu |
| Val | Phe | Lys<br>275 | Lys | Pro | His | Asp | Phe<br>280 | Phe | Pro | Ala | Asn | Pro<br>285 | Leu | Cys | Pro |
| Glu | Thr<br>290 | Pro | Asp | Ala | Ile | His<br>295 | Ile | Val | Asp | Leu | Glu<br>300 | Val | Phe | Pro | Lys |
| Val<br>305 | Ser | Leu | Glu | Leu | Arg<br>310 | Asp | Ser | Val | Leu | His<br>315 | Gly | Ser | Thr | Asp | Ser<br>320 |
| Gly | Phe | Gly | Ser | Gly<br>325 | Lys | Pro | Ser | Leu | Gln<br>330 | Thr | Glu | Glu | Ser | Gln<br>335 | Phe |
| Leu | Leu | Pro | Gly<br>340 | Ser | His | Pro | Gln | Ile<br>345 | Gln | Gly | Thr | Leu | Gly<br>350 | Lys | Glu |
| Glu | Ser | Pro<br>355 | Gly | Leu | Gln | Ala | Thr<br>360 | Cys | Gly | Asp | Asn | Thr<br>365 | Asp | Ser | Gly |
| Ile | Cys<br>370 | Leu | Gln | Glu | Pro | Gly<br>375 | Leu | His | Ser | Ser | Met<br>380 | Gly | Pro | Ala | Trp |
| Lys<br>385 | Gln | Gln | Leu | Gly | Tyr<br>390 | Thr | His | Gln | Asp | Gln<br>395 | Asp | Asp | Ser | Asp | Val<br>400 |
| Asn | Leu | Val | Gln | Asn<br>405 | Ser | Pro | Gly | Gln | Pro<br>410 | Lys | Tyr | Thr | Gln | Asp<br>415 | Ala |
| Ser | Ala | Leu | Gly<br>420 | His | Val | Cys | Leu | Leu<br>425 | Glu | Pro | Lys | Ala | Pro<br>430 | Glu | Glu |
| Lys | Asp | Gln<br>435 | Val | Met | Val | Thr | Phe<br>440 | Gln | Gly | Tyr | Gln | Lys<br>445 | Gln | Thr | Arg |
| Trp | Lys<br>450 | Ala | Glu | Ala | Ala | Gly<br>455 | Pro | Ala | Glu | Cys | Leu<br>460 | Asp | Glu | Glu | Ile |
| Pro<br>465 | Leu | Thr | Asp | Ala | Phe<br>470 | Asp | Pro | Glu | Leu | Gly<br>475 | Val | His | Leu | Gln | Asp<br>480 |
| Asp | Leu | Ala | Trp | Pro<br>485 | Pro | Pro | Ala | Leu | Ala<br>490 | Ala | Gly | Tyr | Leu | Lys<br>495 | Gln |
| Glu | Ser | Gln | Gly | Met | Ala | Ser | Ala | Pro | Pro | Gly | Thr | Pro | Ser | Arg | Gln |

-continued

|   |   |   | 500 |   |   |   | 505 |   |   |   | 510 |   |   |
|---|---|---|---|---|---|---|---|---|---|---|---|---|---|
| Trp | Asn | Gln | Leu | Thr | Glu | Glu | Trp | Ser | Leu | Leu | Gly | Val | Ser | Cys |
|   |   | 515 |   |   |   |   | 520 |   |   |   | 525 |   |   |
| Glu | Asp | Leu | Ser | Ile | Glu | Ser | Trp | Arg | Phe | Ala | His | Lys | Leu | Asp | Pro |
|   | 530 |   |   |   |   | 535 |   |   |   |   | 540 |   |   |   |
| Leu | Asp | Cys | Gly | Ala | Ala | Pro | Gly | Gly | Leu | Leu | Asp | Ser | Leu | Gly | Ser |
| 545 |   |   |   |   | 550 |   |   |   |   | 555 |   |   |   |   | 560 |
| Asn | Leu | Val | Thr | Leu | Pro | Leu | Ile | Ser | Ser | Leu | Gln | Val | Glu | Glu |
|   |   |   |   | 565 |   |   |   |   | 570 |   |   |   |   | 575 |

ANTIBODIES WHICH SPECIFICALLY BIND MAMMALIAN RECEPTORS FOR INTERLEUKIN-10 (IL-10)

This application is a divisional application of commonly assigned then copending patent application U.S. Ser. No. 08/110,683, filed Aug. 23, 1993, which was pending as of February, 1997; which was a continuation-in-part of commonly assigned patent application U.S. Ser. No. 08/011,066, filed on Jan. 29, 1993, since abandoned; which was a continuation-in-part of commonly assigned patent application U.S. Ser. No. 07/989,792, filed on Dec. 10, 1992, since abandoned; each or which is incorporated herein by reference.

FIELD OF THE INVENTION

The present invention relates generally to nucleic acids and polypeptides characteristic of receptors for mammalian interleukin-10, and more particularly to their uses in preparing reagents useful for diagnosing or treating various receptor-related medical conditions.

BACKGROUND OF THE INVENTION

Activated hemopoietic cells secrete numerous proteins. Cytokines are a subset of these proteins and play a variety of important roles in regulation of immune responses by controlling proliferation, differentiation, and the effector functions of immune cells. Most cytokines have more than one biological activity and which activity is the most important likely depends on the local context in which the cytokine is produced.

These cytokines are intercellular signaling molecules whose actions are typically mediated through specific receptor molecules found on target cells. The structure and mechanism of action of these receptors on target cells is not well understood, though many are composed of at least two separate proteins. These earlier described heterodimeric receptors are often composed of polypeptides which are related both to each other and to receptors for other cytokines. Components of receptors for other cytokines have been described. See, e.g., Gearing, et al. (1989) *EMBO J.* 8:3667–3676 (low affinity α chain of a human GM-CSF receptor); Itoh, et al. (1990) *Science* 247:324–327 (low affinity α chain of a mouse IL-3 receptor); and Hayashida, et al. (1990) *Proc. Nat'l Acad. Sci. USA* 87:9655–9659 (a β chain of a human GM-CSF receptor); and Tavernier, et al. (1991) *Cell* 66:1125 (IL-5 receptor, α and β chains). The various components of the earlier identified receptors appear to share properties useful in defining a receptor superfamily of related proteins. See, e.g., Bazan (1990) *Immunology Today* 11:350–354; and Bazan (1990) *Proc. Nat'l Acad. Sci. USA* 87:6934–6938. However, the structure and mechanism of action of a receptor for a mammalian interleukin-10 (IL-10) could not be predicted with reliability based merely upon speculated similarity to receptors for other cytokines.

As soluble intercellular messenger molecules, the cytokines likely bind to cellular receptors, e.g., cell surface receptors. Receptor molecules have been identified and isolated for G-CSF, GM-CSF, EPO, TNF, IFN-γ, IL-2, IL-3, IL-4, IL-5, IL-6, and IL-7. Many of these receptors have two chains, both of which are members of the hemopoietic receptor superfamily. In such cases, typically one chain, designated the α chain, can bind its ligand with low affinity. This interaction may or may not result in transduction to the cell of a signal. Another chain, designated the β chain, when associated with the α chain, confers higher affinity binding of the heterodimeric receptor to the cytokine. The β chain by itself usually lacks significant ligand binding affinity. The dimeric form of receptor is capable of transducing a signal into the cell as a consequence of ligand, e.g., cytokine, binding. However, any similarity between the structural and functional features of those receptors generally and a receptor for IL-10 is speculative. Additional subunits may also be associated with the receptors.

A cytokine synthesis inhibitory factor (CSIF) activity led to assays which allowed the isolation of a cytokine designated interleukin-10 (IL-10). See Fiorentino, et al. (1989) *J. Exptl. Med.* 170:2081–2095; and Mosmann, et al. (1991) *Immunol. Today* 12:A49–A53. Both mouse and human counterparts have been isolated. See Moore, et al. (1990) *Science* 248:1230–1234; and Vieira, et al. (1991) *Proc. Nat'l Acad. Sci. USA* 88:1172–1176. A human viral analog, known as either vIL-10 or BCRF1, has been described which shares many characteristic activities of the natural human form. See Hsu, et al. (1990) *Science* 250:830–832. Another viral homolog has been described from an equine herpes virus. See Rode, et al. (1993) *Viral Genes* 7:111.

Human IL-10 (hIL-10) has an N-terminal hydrophobic signal sequence of 18 amino acids, one potential N-linked glycosylation site, 4 cysteine residues, and seven methionine residues. It shares strong DNA and amino acid sequence homology with mouse IL-10 and an open reading frame in Eppstein-Barr virus, BCRF1, and an open reading frame in an equine herpes virus, type II. It inhibits cytokine synthesis by activated T cells, stimulates growth for thymocytes and mast cells, induces class II MHC expression, and sustains viability in culture of small dense resting mouse B cells. A mouse counterpart has also been described, and equivalent proteins would be found in other mammalian species. IL-10 binding to cell surface receptors is thought to be an initiating step for various specific cellular responses, as described below.

One means to modulate IL-10 effect upon binding to its receptor, and therefore potentially useful in treating inappropriate immune responses, e.g., autoimmune, inflammation, sepsis, and cancer situations, is to inhibit the receptor signal transduction. Unfortunately, finding reagents capable of serving as an antagonist or agonist has been severely hampered by the absence of large quantities of IL-10 receptor, preferably purified and in an active form. In order to characterize the structural properties of the IL-10 receptor in greater detail and to understand the mechanism of action at the molecular level, purified receptor will be very useful.

Moreover, similarities to other cytokine functions exist. In particular, the IL-10 receptor likely shares many functions and characteristics with other receptors, but also exhibits different structural and functional properties. The receptors provided herein, by comparison to other receptors or by combining structural components, will provide further understanding of signal transduction induced by ligand binding.

The isolated receptor gene should provide means to generate an economical source of the receptor, allow expression of more receptors on a cell leading to increased assay sensitivity, promote characterization of various receptor subtypes and variants, and allow correlation of activity with receptor structures. Moreover, fragments of the receptor may be useful as agonists or antagonists of ligand binding. See, e.g., Harada, et al. (1992) *J. Biol. Chem.* 267:22752–22758.

Thus, a need exists for the isolation and characterization of nucleic acids encoding components of receptors for IL-10. The present invention provides these and the means for preparing many other useful reagents.

SUMMARY OF THE INVENTION

The present invention provides nucleic acid and protein sequences of components of a receptor for IL-10. Both a human IL-10 receptor component and a mouse counterpart are exemplified, though equivalent components from other mammalian species will be found by similar methods or based upon other properties derived therefrom.

The present invention provides recombinant or isolated nucleic acids comprising a sequence exhibiting homology to a sequence encoding a mammalian receptor for IL-10, a fragment thereof, or a unique portion thereof. In preferred embodiments, the nucleic acids will comprise deoxyribonucleic acid, will be isolated, further comprise a regulatory sequence from the 5' or 3' sequence adjacent a gene encoding a receptor for IL-10, or are operably linked to a genetic control element. In alternative embodiments the receptors, fragments, or portions thereof have a biological activity, e.g., one characteristic of a receptor for IL-10, or are from a mammal, including a mouse or human.

In particular embodiments, the nucleic acids, are capable of hybridizing at high stringency to SEQ ID NO: 1 or 3, or are isolated using a probe which hybridizes at high stringency to a human receptor for IL-10. The invention also embraces nucleic acids capable of hybridizing to these sequences which contain mutations selected from the group consisting of nucleotide substitutions, nucleotide deletions, nucleotide insertions, and inversions of nucleotide stretches. Alternative embodiments include recombinant nucleic acids which are operably linked to a genetic control element, e.g., a prokaryotic promoter element or a eukaryotic expression control element, including a viral promoter.

Various embodiments include expression vectors for expressing DNA encoding a receptor for IL-10, or vectors comprising these sequences and a selection marker. The invention also embraces host cells comprising an expression vector which is capable of expressing these receptors. Preferred host cell embodiments include prokaryotes, including gram negative and gram positive bacteria, including *E. coli*; lower eukaryotes, including yeasts; and higher eukaryotes, including animal cells, including mammalian cells, including human. Preferably the receptor is selected from a human receptor for IL-10; or a mouse receptor for IL-10. Other embodiments include nucleic acids further encoding a second protein or polypeptide, e.g., where the second polypeptide is fused to the receptor. The invention further embraces subcellular structures, cells, or organisms comprising these nucleic acids.

The present invention also embraces proteins or polypeptides encoded by these DNA sequences, preferably which are substantially free of protein or cellular contaminants, other than those derived from a recombinant host. The receptor proteins or polypeptides will often be from a mammal, including a mouse or human, and can have an amino acid sequence as found in SEQ ID NO: 2 or 4, or an allelic or species variant thereof, or a unique portion thereof. The receptor proteins or polypeptides can be attached to a solid support, be substantially pure, or be in a pharmaceutically acceptable form, with or without additional carriers or excipients. The invention also conceives of fusion proteins or polypeptides, including those further comprising a sequence from a second receptor protein. Other embodiments include subcellular structures, cells, or organisms comprising such receptor proteins or polypeptides.

The invention also provides methods for producing receptor proteins or polypeptides comprising culturing a cell comprising a described nucleic acid in a nutrient medium; and expressing the receptor proteins or polypeptides in the cell. Various alternative embodiments further comprise a step of purifying the receptor proteins or polypeptides, where the receptor proteins or polypeptides are secreted into the medium and purified therefrom, and wherein the receptor is from a mammal, including a mouse or human. The invention also provides receptors made by these methods and exhibiting a post-translational modification pattern distinct from that in normal native receptor, e.g., glycosylation; alkylation; and carboxylation. The receptor can be made in a cell line expressing a receptor exhibiting a non-natural receptor glycosylation pattern. The invention also provides methods for diagnosing a medical condition characterized by inappropriate IL-10 response in a host comprising contacting a sample from the host with a specific binding reagent to a nucleic acid encoding a receptor for IL-10 or fragment thereof; or to a receptor for IL-10 or fragment thereof, and measuring the level of binding of the reagent to the sample. In various alternatives, the binding reagent is a nucleic acid probe for a gene encoding the receptor or fragment thereof, an antibody which recognizes a receptor for IL-10 or a fragment thereof; or a ligand, agonist, or antagonist for a receptor for IL-10. Preferably the receptor is from a mammal, including a mouse or human.

The invention also provides methods of screening for a compound having binding affinity to a receptor for IL-10, comprising producing an isolated or recombinant receptor by a method as described; and assaying for the binding of the compound to the receptor, thereby identifying compounds having defined binding affinity therefor. Preferably, the compound is a ligand, agonist, or antagonist for these receptors.

The present invention also provides proteins and polypeptides, e.g., free of proteins with which they are naturally associated and having an amino acid sequence homologous to a fragment of a receptor for IL-10. Typically, the receptor is from a mammal, including a mouse or human, and specific embodiments have sequence of SEQ ID NO: 2 or 4.

The invention encompasses a recombinant or substantially pure polypeptides comprising a region exhibiting substantial identity to an amino acid sequence of a receptor for IL-10. Particular embodiments include polypeptides having a sequence selected from SEQ ID NO: 2 or 4, or polypeptides attached to a solid support.

The present invention provides various antibodies having binding affinity to a recombinant receptor for IL-10, or a fragment thereof. Preferred embodiments are raised against the receptor for IL-10, and can be either neutralizing or non-neutralizing antibodies, fused to a toxic moiety, or conjugated to a marker moiety, including a radionuclide. Preferably, the antibody binds to a receptor from a mammal, including a mouse or human.

Additionally, the invention provides methods of treating a host having a medical condition characterized by inappropriate IL-10 response or exhibiting abnormal expression of a receptor for IL-10, comprising administering to the host a therapeutically effective amount of a composition comprising (a) an antibody which binds to a receptor for IL-10 or fragment thereof; (b) a ligand, agonist, or antagonist for a receptor for IL-10; or (c) a ligand binding receptor, or fragment thereof, for IL-10. In one embodiment, the antibody is a monoclonal antibody. In others, the agonist or antagonist is selected by a method of contacting a target compound with (a) isolated or recombinant receptor for IL-10, or (b) ligand binding fragment of the receptor; and identifying the target compound with isolated or recombinant receptor for IL-10, or ligand binding fragment of the receptor; and identifying the target compound based upon the effects of the contacting.

The invention also provides methods of evaluating binding affinity of a test compound to a receptor for IL-10, the method comprising contacting (a) a sample containing the receptor, or a fragment thereof, with a labeled compound having known affinity for the receptor; and (b) the test compound; and measuring the level of bound labeled compound, the amount being inversely proportional to the amount of test compound which bound to the receptor. Preferably, the receptor is from a mammal, including a mouse or human. An alternative embodiment is a method of modulating biological activity of a receptor for IL-10, comprising contacting the receptor with a composition selected from an antibody which binds to the receptor; a ligand, agonist, or antagonist for a receptor for IL-10; and a ligand binding fragment from a receptor for IL-10.

The invention also provides useful reagents in kit form. For example, it provides a kit useful for (a) quantifying a receptor for IL-10; or (b) for determining the bindings affinity of a test sample to a receptor for IL-10; the kit comprising a labeled compound having binding affinity for the receptor, and a means for measuring bound labeled compound. Various embodiments include kits further comprising recombinant receptor, wherein the labeled compound is a ligand for the receptor, including IL-10; wherein the compound is an antibody; wherein the means for measuring is a solid phase for immobilizing the receptor; or wherein the solid phase contains a capture molecule. The invention also provides a kit for assaying, in a sample, antibody against a receptor for IL-10, comprising the receptor and an antibody detection means. In one embodiment the receptor is attached to a solid support.

The invention also provides compounds known to modulate activity of a receptor for IL-10, selected by a method of: contacting the compound with isolated or recombinant receptor, or a fragment thereof, for IL-10; and evaluating the effect on biological activity by the contacting.

The invention also provides methods of modulating a biological effect of IL-10, comprising a step of interfering with biological mechanisms, e.g., signal transduction, of a class 2 cytokine receptor, e.g., an interferon receptor. It also provides methods of modulating a biological effect of a class 2 receptor, e.g., an interferon, comprising a step of interfering with biological mechanisms of an IL-10 receptor.

BRIEF DESCRIPTION OF THE FIGURES

In FIG. 7A, approximately 0.4 ml of lactoperoxidase-iodinated hIL-10 was passed through a 120 ml G75 Sepharose (Pharmacia LKB) column and collected in 1.1 ml fractions. Radioactivity was determined from fraction aliquots with a Clinigamma Counter (Pharmacia LKB). Blue Dextran (BD) and Bromophenol Blue (BPB) were used as markers for the void and total volumes, respectively. In FIG. 7B, low molecular weight markers (Pharmacia LKB) were applied to the G75 column, 1.1 ml fractions were collected, and protein concentrations of these fractions were determined using the BCA Protein Detection System (Pierce, Rockford, Ill.). The fractions of peak protein concentration were then plotted against the logarithms of the molecular weights. For FIG. 7C, approximately 20,000 cpm from the three peak fractions were partitioned in a 15% SDS-PAGE under non-reducing conditions. At the completion of the electrophoresis the gel was vacuum dried on Whatman paper followed by autoradiography using XAR film (Kodak). Molecular weight markers (BRL) were visualized by Coomassie blue staining.

In FIG. 11A, the two bars of each set indicate binding in the absence (left) or presence (right) of 1000-fold molar excess unlabeled hIL-10, respectively, in binding buffer with 500 pM labeled hIL-10. Triplicate binding assays were performed. Two binding experiments using the same preparation of labeled hIL-10 are presented in FIG. 11B.

In FIG. 12A, increasing concentrations of labeled hIL-10 were added to $5 \times 10^6$ MC/9 cells and tested for specific binding. FIG. 12B shows Scatchard analysis of the data obtained above using the EBDA program (Elsevier Biosoft, Cambridge, U.K.). The slope of the line obtained gives a Kd value of 49 pM while the Bmax is 4.0 pM.

In FIG. 13A, increasing concentrations of labeled hIL-10 were added to $5 \times 10^6$ JY cells and tested for specific binding. FIG. 13B shows Scatchard analysis of data obtained from above using the EBDA program. The slope of the line gives an estimated Kd value of 140 pM while the Bmax value is 7.5 pM.

In FIG. 14A, a 500-fold molar excess of unlabeled human IL-10 or 1500-fold excess mouse IL-10 was incubated in duplicate with 100 pM iodinated hIL-10 in a binding assay with the mouse mast cell line MC/9. FIG. 14B shows the same as A except that the human B lymphoma line JY was used.

FIG. 15A shows the human IL-10 receptor and FIG. 15B shows the mouse IL-10 receptor.

FIG. 16A shows the increasing specific binding obtained when increasing amounts of labeled human IL-10 are added to COS7 cells transfected with the human (SW8.1) IL-10 cDNA clone. FIG. 16B shows a Scatchard plot obtained from these data points, which provide a Kd value of 120 pM. This result indicates that the recombinant human receptor, when expressed in COS7 cells, is able to bind human IL-10 with an affinity comparable to that of the natural human IL-10 receptor, as shown previously.

FIG. 17A shows the increasing specific binding obtained when increasing amounts of labeled human IL-10 are added to COS7 cells transfected with the mouse (m3.14) IL-10 cDNA clone. FIG. 17B shows a Scatchard plot obtained from these data points, which provide a Kd value of 83 pM. This result indicates that the recombinant mouse receptor, when expressed in COS7 cells, is able to bind human IL-10 with an affinity comparable to that of the natural human IL-10 receptor.

DETAILED DESCRIPTION OF THE PREFERRED EMBODIMENTS

Contents

Figure 1:
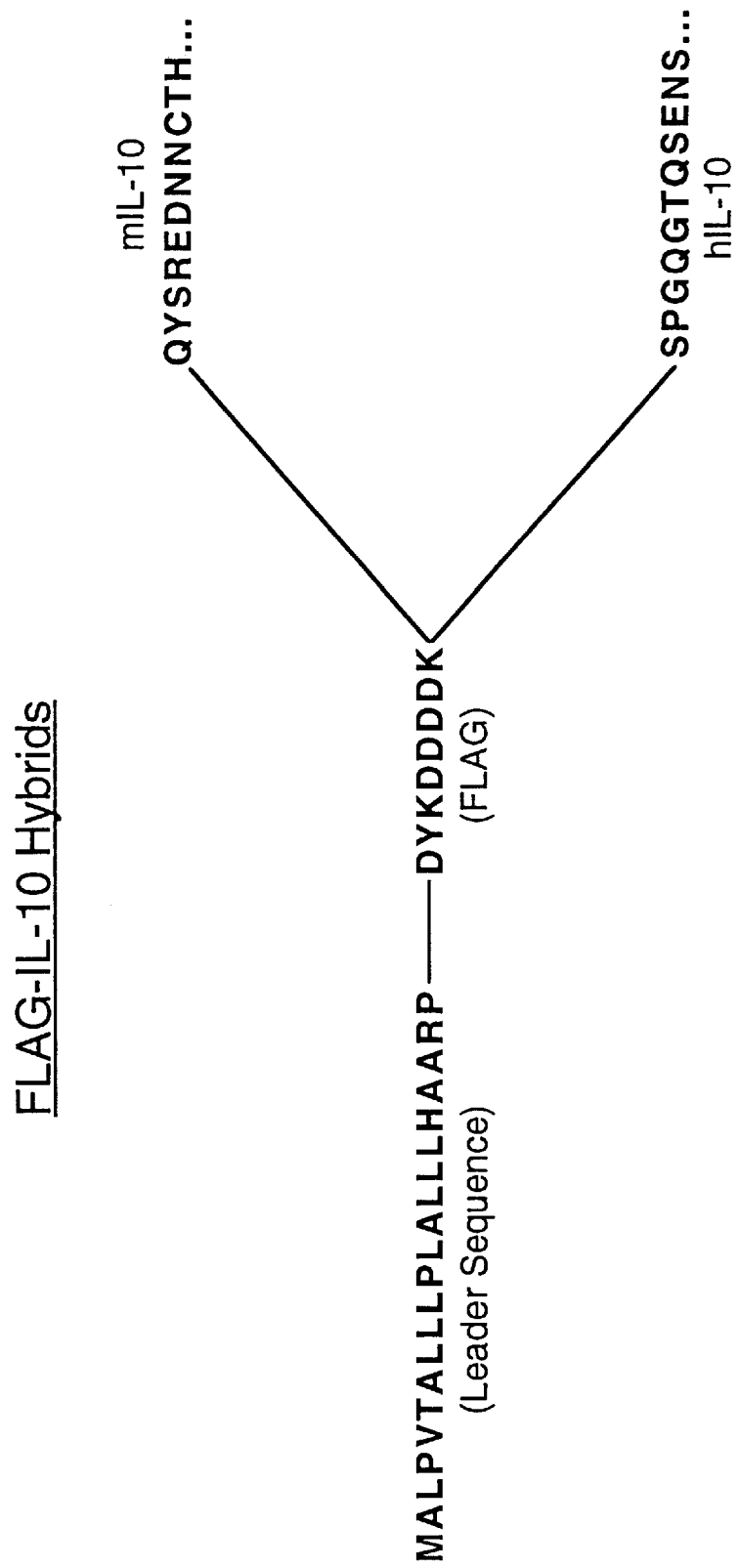
FIG. 1 shows the structure of the FLAG-mouse IL-10 (FLAG-mIL-10) and FLAG-human IL-10 (FLAG-hIL-10) hybrid cytokines. A leader sequence from the human CD8 gene was used to ensure processing and secretion of FLAG-IL-10.
Figure 2A:
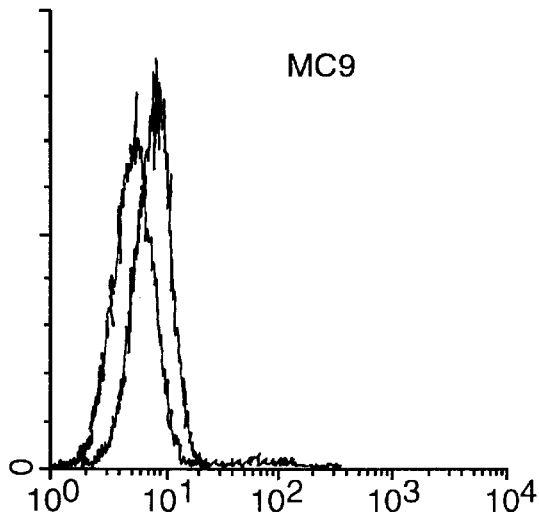
FIGS. 2A–2D show detection by Fluorescence Activated Cell Sorter (FACS) analysis and enhancement of IL-10 receptor expression. MC/9 is a mouse mast cell line. J774 is a mouse macrophage cell line. Panels labeled MC9 and J774 show FACS profiles from freshly cultured cells. Panels labeled MC9-b2 and J774-a2 show FACS profiles after three cycles of enrichment for the top 3%–5% of IL-10 receptor positive cells. In each panel, the right profile shows a profile of FLAG-mIL-10 bound to IL-10 receptor, while the left profile show the result of competition with a 30–100-fold excess of wild-type mIL-10, which reduces signal to background. For FIGS. 2, 3, 4, and 5, the horizontal axis is fluorescence intensity in arbitrary units, and the vertical axis is cell number, in arbitrary units.
Figure 2B:
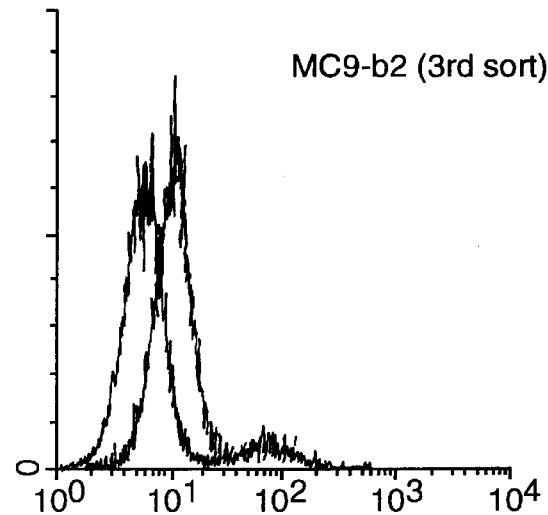
Figure 2C:
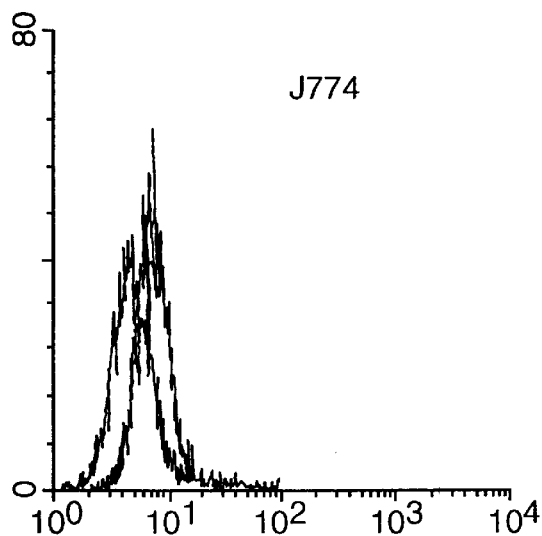
Figure 2D:
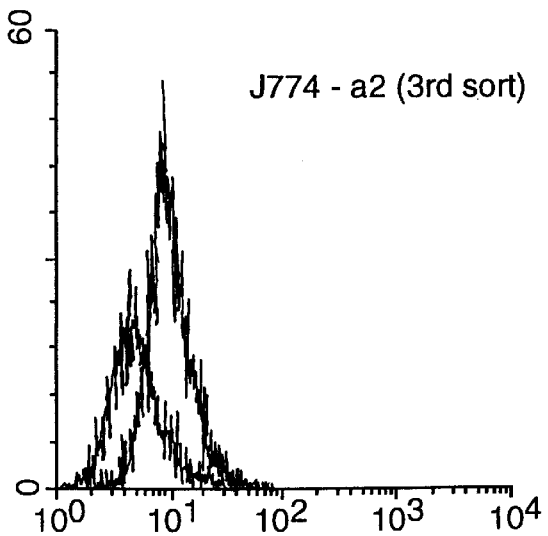

I. General
II. Nucleic Acids
III. Receptor Variants
IV. Making Receptor
V. Receptor Isolation
VI. Receptor Analogues
VII. Antibodies
VIII. Other Uses of Receptors
IX. Ligands: Agonists and Antagonists
X. Kits
XI. Therapeutic Applications
XII. Additional Receptor Subunits I. General The present invention provides amino acid sequence and DNA sequence for components of receptors for interleukin-10, e.g., both a human receptor subunit and a mouse receptor subunit. These sequences were obtained based upon the ability of the protein which they encode to bind IL-10. Pools of cells containing cDNA expression library products were screened for their ability to bind IL-10. The receptor-ligand complexes were chemically crosslinked and methods were applied to isolate nucleic acids encoding those binding proteins.

This invention provides recombinant nucleic acids, and isolated or substantially pure nucleic acids, which are substantially homologous to a sequence encoding a receptor, or a fragment thereof, for an IL-10 peptide. Nucleic acids encoding fusion polypeptides are contemplated, as are vectors, cells, and organisms comprising such nucleic acids. Recombinant polypeptides, and isolated or substantially pure polypeptides derived from these protein sequences are encompassed herein. Fusion polypeptides are provided, along with cells and organisms comprising the polypeptides. Compositions comprising these polypeptides are embraced herein. Exemplary embodiments are, again, full length human and mouse proteins, and fragments thereof, e.g., soluble ligand binding fragments consisting of the extracellular domain of the protein.

The invention provides antibodies specific for epitopes unique to, or characteristic of, these receptor components. These include antibodies which bind specifically to either epitopes which are shared by the different species counterparts of receptors for IL-10, or epitopes which distinguish between different species counterparts.

Kits comprising any of these compositions are included herein. Thus, various nucleic acid molecules, polypeptides, and antibodies will provide the bases of various diagnostic or therapeutic kits.

The various compositions also provide bases for methods for treating hosts, particularly those suffering from undesired receptor function, e.g., autoimmune diseases, inappropriate immune responses of the T helper 2 class, inappropriate function of class II MHC, suppressed monocyte or macrophage-related immune functions, septic or toxic shock responses, and intracellular pathogen-mediated diseases, by administering effective amounts of these reagents, directly or indirectly, or contacting biological samples with them.

The compositions, e.g., ligand-binding fragments of the receptor, also provide the means to select and screen for additional agonists and antagonists for the respective receptor subtypes. Selected compounds are made available, both ligands and molecules which interact at polypeptide regions separate from the ligand binding regions. Of particular utility are compounds affecting multiple receptor types, e.g., those exhibiting desired spectra of specificity for modulating various biological activities.

The group of receptor components is also very useful in providing a group of receptor polypeptides having both substantial similarities and critical differences. These different species counterparts, as a group, may allow dissecting of structure and function for the class in a manner impossible from characterization of a single species version.

The descriptions below are often directed to either a mouse IL-10 receptor or a human receptor, but most properties, both structural or biological, will be shared between them and other mammalian counterparts, e.g., rat, pig, sheep, goat, etc. In particular, analogous uses and reagents derived from other species counterparts will be developed. Identification of new bioactive ligands for new receptor variants will also result.

Expression cloning of an IL-10 binding protein yielded nucleic acids encoding IL-10 receptor components from both human and mouse. Some standard methods are described or referenced, e.g., in Maniatis, et al. (1982) *Molecular Cloning, A Laboratory Manual*, Cold Spring Harbor Laboratory, Cold Spring Harbor Press; Wu, et al. (eds) (1989) "Recombinant DNA Methodology" from *Methods in Enzymology*, Academic Press, NY; Sambrook, et al. (1989) *Molecular Cloning: A Laboratory Manual*, (2d ed.), vols 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; all of which are each incorporated herein by reference. These genes allow isolation of species variants of these genes encoding a component of a receptor for IL-10, beyond the herein described human and mouse embodiments. One procedure is broadly set forth below in Table 1.

TABLE 1

Detection of IL-10 Receptor

1. Cells + FLAG-IL-10 ± excess IL-10
2. Wash
3. Cross-linking
4. Wash
5. Biotinylated anti-FLAG antibody (M1 or M2)
6. Wash
7. Streptavidin-phycoerythrin conjugate (SA-PE)
8. Wash
9. Fluorescence activated cell sorting (FACS)

A cDNA library, constructed in an appropriate expression vector was prepared from RNA isolated from appropriate cells. These cells were responsive to IL-10. A B cell line BJAB was used to make the cDNA library from human, and a mast cell line MC/9 and a macrophage cell line J774 were used to make cDNA from mouse. Several modifications and unique techniques had to be utilized to overcome problems associated with isolating a cDNA clone by expression cloning. In particular, it was necessary to identify an appropriate cell line from which to prepare the cDNA library encoding the desired IL-10 binding activity. Next, it was very useful to establish that IL-10 could bind to clonally isolated expression products. A cell line for expression with low background binding was also useful.

The IL-10 used as a ligand was modified by addition of an N-terminal extension. This extension was useful in providing a means to detect a ligand-receptor crosslinked complex. In this case, the extension was the FLAG peptide, though others could have been equivalent. See Hopp, et al. (1988) *Bio/Technology* 6:1204–1210. At the outset, it was unclear that the extension would not interfere in ligand-receptor interaction. It was also unclear whether the IL-10 binding protein interaction was physiologically important.

The extension provided a means to attach a marker or signal for a crosslinked ligand-receptor complex. Thus, means were provided to detect cells expressing a receptor component, or to affinity immobilize cells possessing a crosslinked complex on their surface. Both of these methods were applied to enrich and verify the identity of the receptor component.

Once a cDNA for a receptor component was isolated from mouse, it was partially sequenced. The same was done for the human receptor. Both are now completely sequenced. The nucleotide sequence reveals partial amino acid sequence of the primary translation product of an IL-10 receptor component, i.e., the amino acid sequence before any post-translational modification. The present invention encompasses both allelic variants of the protein and various metabolic variants, e.g., post-translational modifications, produced by different cell types, including recombinant proteins. Various glycosylation variants and post-translational modification variants are available by choosing appropriate cells for expression of recombinant nucleic acids.

Complete human IL-10R nucleotide and amino acid sequences are shown in Table 2. SEQ ID NO: 1 corresponds to a human nucleotide sequence; SEQ ID NO: 2 corresponds to a human amino acid sequence. Table 3 discloses nucleotide and amino acid sequences of the mouse receptor component, which binds IL-10. SEQ ID NO: 3 corresponds to a mouse nucleic acid sequence; SEQ ID NO: 4 corresponds to a mouse amino acid sequence; see Table 3. The human sequence was derived from the clone SW8.1, which was deposited with the ATCC on Dec. 4, 1992, and assigned accession number 69146. The nucleotide sequence has been verified in both directions, and the presumptive open reading frame would begin in the appropriate position corresponding to that indicated in Table 3 for the mouse sequence. A hydrophobic membrane spanning segment appears to correspond to amino acids 217–243 of the human receptor component. Thus, a soluble binding fragment would correspond to one extending from about residues 1–216, or shorter.

TABLE 2

Nucleotide and derived amino acid sequences from
a human cDNA encoding an IL-10 receptor component. Lower case
indicates the nucleotide has been sequence in only one of the
opposing strand directions.

nucleotide sequence:

AAAGA GCTGG AGGCG CGCAG GCCGG CTCCG CTCCG GCCCC GGACG ATGCG

GCGCG CCCAG GATGC TGCCG TGCCT CGTAG TGCTG CTGGC gGCGC TCCTC

AGCCT CCGTC TTGGC TCAGA CGCTC ATGGG ACAGA GCTGC CCAGC CCTCC

GTCTG TGTGG TTTGA AGCAG AATTT TTCCA CCACA TCCTC CACTG GACAC

CCATC CCAAA TCAGT CTGAA ATGAA GTGGC GCTCC TGAGG TATGG AATAG

TABLE 2-continued

Nucleotide and derived amino acid sequences from
a human cDNA encoding an IL-10 receptor component. Lower case
indicates the nucleotide has been sequence in only one of the
opposing strand directions.

```
AGTCC TGGAA CTCCA TCTCC AACTG TAGCC AGACC CTGTC CTATG ACCTT
ACCGC AGTGA CCTTG GACCT GTACC ACAGC AATGG CTACC GGGCC AGAGT
GCGGG CTGTG GACGG CAGCC GGCAC TCCAA CTGGA CCGTC ACCAA CACCC
GCTTC TCTGT GGATG AAGTG ACTCT GACAG TTGGC AGTGT GAACC TAGAG
ATCCA CAATG GCTTC ATCCT CGGGA AGATT CAGCT ACCCA GGCCC AAGAT
GGCCC CCGCG AATGA CACAT ATGAA AGCAT CTTCA GTCAC TTCCG AGAGT
ATGAG ATTGC CATTC GCAAG GTGCC GGGAA ACTTC ACGTT CACAC ACAAG
AAAGT AAAAC ATGAA AACTT CAGCC TCCTA ACCTC TGGAG AaGTG GGAGA
GTTCT GTGTC CAGGT GAAAC CATCT GTCGC TTCCC GAAGT AACAA GGGGA
TGTGG TCTAA AGAGG AGTGC ATCTC CCTCA CCAGG CAGTA TTTCA CCGTG
ACCAA CGTCA TCATC TTCTT TGCCT TTGTC CTGCT GCTCT CCGGA GCCCT
CGCCT ACTGC CTGGC CCTCC AGCTG TATGT GCGGC GCCGA AAGAA GCTAC
CCAGT GTCCT GCTCT TCAAG AAGCC CAGCC CCTTC ATCTT CATCA GCCAG
CGTCC CTCCC CAGAG ACCCA AGACA CCATC CACCC GCTTG ATGAG GAGGC
CTTTT TGAAG GTGTC CCCAG AGCTG AAGAA CTTGG ACCTG CACGG CAGCA
CAGAC AGTGG CTTTG GCAGC ACCAA GCCAT CCCTG CAGAC TGAAG AGCCC
CAGTT CCTCC TCCCT GACCC TCACC CCCAG GCTGA CAGAA CGCTG GGAAA
CGGGG AGCCC CCTGT GCTGG GGGAC AGCTG CAGTA GTGGC AGCAG CAATA
GCACA GACAG CGGGA TCTGC CTGCA GGAGC CCAGC CTGAG CCCCA GCACA
GGGCc CACCT GGGAG CAACA GGTGG GGAGC AACAG CAGGG GCCAG GATGA
CAGTG GCATT GACTT AGTTC AAAAC TCTGA GGGCC GGGCT GGGGA CACAC
AGGGT GGCTC GGCCT TGGGC CACCA CAGTC CCCCG GAGCC TGAGG TGCCT
GGGGA AGAAG ACCCA GCTGC TGTGG CATTC CAGGG TTACC TGAGG CAGAC
CAGAT GTGCT GAAGA GAAGG CAACC AAGAC AGGCT GCCTG GAGGA AGAAT
CGCCC TTGAC AGATG GCCTT GGCCC CAAAT TCGGG AGATG CCTGG TTGAT
GAGGC AGGCT TGCAT CCACC AGCCC TGGCC AAGGG CTATT TGAAA CAGGA
TCCTC TAGAA ATGAC TCTGG CTTCC TCAGG GGCCC CAACG GGACA GTGGA
ACCAG CCCAC TGAGG AATGG TCACT CCTGG CCTTG AGCAG CTGCA GTGAC
CTGGG AATAT CTGAC TGGAG CTTTG CCCAT GACCT TGCCC CTCTA GGCTG
TGTGG CAGCC CCAGG TGGTC TCCTG GGCAG CTTTA ACTCA GACCT GGTCA
CCCTG CCCCT CATCT CTAGC CTGCA GTCAA GTGAG TGACT CGGGC TGAGA
GGCTG CTTTT GATTT TAGCC ATGCC TGCTC CTCTG CCTGG ACCAG GAGGA
GGGCC CTGGG GCAGA AGTTA GGCAC GAGGC AGTCT GGGCA CTTTT CTGCA
AGTCC ACTGG GGCTG GCCCA GCCAG GCTGC AGGGC TGGTC AGGGT GTCTG
GGGCA GGAGG AGGCC AACTC ACTGA ACTAG TGCAG GGTAT GTGGG TGGCA
CTGAC CTGTT CTGTT GACTG GGGCC CTGCA GACTC TGGCA GAGCT GAGAA
GGGCA GGGAC CTTCT CCCTC CTAGG AACTC TTTCC TGTAT CATAA AGGAT
TATTT GCTCA GGGGA ACCAT GGGGC TTTCT GGAGT TGTGG TGAGG CCACC
AGGCT GAAGT CAGCT CAGAC CCAGA CCTCC CTGCT TAGGC CACTC GAGCA
TCAGA GCTTC CAGCA GGAGG AAGGG CTGTA GGAAT GGAAG CTTCA GGGCC
```

TABLE 2-continued

Nucleotide and derived amino acid sequences from
a human cDNA encoding an IL-10 receptor component. Lower case
indicates the nucleotide has been sequence in only one of the
opposing strand directions.

TTGCT GCTGG GGTCA TTTTT AGGGG AAAAA GGAGG ATATG ATGGT CACAT
GGGGA ACCTC CCCTC ATCGG GCCTC TGGGG CAGGA AGCTT GTCAC TGGAA
GATCT TAAGG TATAT ATTTT CTGGA CACTC AAACA CATCA TAATG GATTC
ACTGA GGGGA GACAA AGGGA GCCGA GACCC TGGAT GGGGc TTCCA GCTCA
GAACC CATCC CTCTG gTGGg TACCT CTGGC ACCCA TCTGC AAATA TCTCC
CTCTC TCCAA CAAAT GGAGT AGCAT cCCCC TGGGG CACTT GCTGA GGCCA
AGCCA CTCAC ATCCT CACTT TGCTG CCCCA CCATC TTGCT GACAA CTTCC
AGAGA AGCCA TGGTT TTTTG TATTG GTCAT AACTC AGCCc TTTGG GCGGC
CTCTG GGCTT GGGCA CCAGC TCATG CCAGC CCCAG AGGGT CAGGG TTGGA
GGCCT GTGCT TGTGT TTGCT GCTAA TGTCC AGCTA CAGAC CCAGA GGATA
AGCCA CTGGG CACTG GGCTG GGGTC CCTGC CTTGT TGGTG TTCAG CTGTG
TGATT TTGGA CTAGC CACTT GTCAG AGGGC CTCAA TCTCC CATCT GTGAA
ATAAG GACTC CACCT TTAGG GGACC CTCCA TGTTT GCTGG GTATT AGCCA
AGCTG GTCCT GGGAG AATGC AGATA CTGTC CGTGG ACTAC CAAGC TGGCT
TGTTT CTTAT GCCAG AGGCT AACAG ATCCA ATGGG AGTCC ATGGT GTCAT
GCCAA GACAG TATCA GACAC AGCCC CAGAA GGGGG CATTA TGGGC CCTGC
CTCCC CATAG GCCAT TTGGA CTCTG CCTTC AAACA AAGGC AGTTC AGTCC
ACAGG CATGG AAGCT GTGAG GGGAC AGGCC TGTGC GTGCC ATCCA GAGTC
ATCTC AGCCC TGCCT TTCTC TGGAG CATTC TGAAA ACAGA TATTC TGGCC
CAGGG AATCC AGCCA TGACC CCCAC CCCTC TGCCA AAGTA CTCTT AGGTG
CCAGT CTGGT AACTG AACTC CCTCT GGAGG CAGGC TTGAG GGAGG ATTCC
TCAGG GTTCC CTTGA AAGCT TTATT TATTT ATTTT GTTCA TTTAT TTATT
GGAGA GGCAG CATTG CACAG TGAAA GAATT CTGGA TATCT CAGGA GCCCC
GAAAT TCTAG CTCTG ACTTT GCTGT TTCCA GTGGT ATGAC CTTGG AGAAG
TCACT TATCC TCTTG GAGCC TCAGT TTCCT CATCT GCAGA ATAAT GACTG
ACTTG TCTAA TTCAT AGGGA TGTGA GGTTC TGCTG AGGAA ATGGG TATGA
ATGTG CCTTG AACAC AAAGC TCTGT CAATA AGTGA TACAT GTTTT TTATT
CCAAT AAATT GTCAA GACCA CA1 amino acid sequence:

MLPCL VVLLA ALLSL RLGSD AHGTE LPSPP SVWFE AEFFH HILHW TPIPN
QSEST CYEVA LLRYG IESWN SISNC SQTLS YDLTA VTLDL YHSNG YRARV
RAVDG SRHSN WTVTN TRFSV DEVTL TVGSV NLEIH NGFIL GKIQL PRPKM
APAND TYESI FSHFR EYEIA IRKVP GNFTF THKKV KHENF SLLTS GEVGE
FCVQV KPSVA SRSNK GMWSK EECIS LTRQY FTVTN VIIFF AFVLL LSGAL
AYCLA LQLYV RRRKK LPSVL LFKKP SPFIF ISQRP SPETQ DTIHP LDEEA
FLKVS PELKN LDLHG STDSG FGSTK PSLQT EEPQF LLPDP HPQAD RTLGN
GEPPV LGDSC SSGSS NSTDS GICLQ EPSLS PSTGP TWEQQ VGSNS RGQDD
SGIDL VQNSE GRAGD TQGGS ALGHH SPPEP EVPGE EDPAA VAFQG YLRQT

TABLE 2-continued

Nucleotide and derived amino acid sequences from
a human cDNA encoding an IL-10 receptor component. Lower case
indicates the nucleotide has been sequence in only one of the
opposing strand directions.

RCAEE KATKT GCLEE ESPLT DGLGP KFGRC LVDEA GLHPP ALAKG YLKQD

PLEMT LASSG APTGQ WNQPT EEWSL LALSS CSDLG ISDWS FAHDL APLGC

VAAPG GLLGS FNSDL VTLPL ISSLQ SSE1

As used herein, the term "IL-10 receptor" shall include a protein or peptide comprising amino acid sequences described in Tables 2 or 3 or encoded by nucleic acid sequences shown therein, or a fragment of either entity. It also refers to a polypeptide which functionally and similarly binds to an IL-10 protein, e.g., human or mouse, with high affinity, e.g., at least about 10 nM, usually better than about 3 nM, preferably better than about 1 nM, and more preferably at better than about 0.5 nM. It is expected that the binding affinity of a multiprotein complex to the ligand will be higher when additional protein components associate with the component disclosed herein, e.g., an α-like chain. The term shall also be used herein to refer, when appropriate, to a receptor gene, alleles of the human or mouse receptor component, or other species counterparts, e.g., mammals other than humans or mice. The term does not encompass natural antibodies which bind the ligand, since the structural features, e.g., complementarity determining regions (CDRs) of an antibody binding site, are different from a receptor's ligand binding site. Nucleic acid sequence from a mouse counterpart receptor component is provided in Table 3. This nucleic acid sequence corresponds to SEQ ID NO: 3 and a predicted corresponding amino acid sequence is designated SEQ ID NO: 4. This mouse sequence was derived from the clone pMR29, which was deposited with the ATCC on Dec. 4, 1992, and has been assigned accession number 69147. Table 4 compares the human and mouse receptors at both the nucleotide and amino acid levels.

TABLE 3

Nucleotide and predicted amino acid sequence
derived from a mouse cDNA encoding an IL-10 receptor component.
Lower case positions have not been verified in both directions
of the double stranded nuceic acid. The initiation codon starts
at nucleotide 61.

nucleotide sequence:
ccatt   gtgct   ggAAA   GCAGG   ACGCG   CCGGC   CGGAG   GCGTA   AAGGC   CGGCT

CCAGT   GGACG   ATGCC   GCTGT   GCGCC   CAGGA   TGTTG   TCGCG   TTTGC   TCCCA

TTCCT   CGTCA   CGATC   TCCAG   CCTGA   GCCTA   GAATT   CATTG   CATAC   GGGAC

AGAAC   TGCCA   AGCCC   TTCCT   ATGTG   TGGTT   TGAAG   CCAGA   TTTTT   CCAGC

ACATC   CTCCA   CTGGA   AACCT   ATCCC   AAACC   AGTCT   GAGAG   CACCT   ACTAT

GAAGT   GGCCC   TCAAA   CAGTA   CGGAA   ACTCA   ACCTG   GAATG   ACATC   CATAT

CTGTA   GAAAG   GCTCA   GGCAT   TGTCC   TGTGA   TCTCA   CAACG   TTCAC   CCTGG

ATCTG   TATCA   CCGAA   GCTAT   GGCTA   CCGGG   CCAGA   GTCCG   GGCAG   TGGAC

AACAG   TCAGT   ACTCC   AACTG   GACCA   CCACT   GAGAC   TCGCT   TCACA   GTGGA

TGAAG   TGATT   CTGAC   AGTGG   ATAGC   GTGAC   TCTGA   AAGCA   ATGGA   CGGCA

TCATC   TATGG   GACAA   TCCAT   CCCCC   CAGGC   CCACG   ATAAC   CCCTG   CAGGG

GATGA   GTACG   AACAA   GTCTT   CAAGG   ATCTC   CGAGT   TTACA   AGATT   TCCAT

CCGGA   AGTTC   TCAGA   ACTAA   AGAAT   GCAAC   CAAGA   GAGTG   AAACA   GGAAA

CCTTC   ACCCT   CACGG   TCCCC   ATAGG   GGTGA   GAAAG   TTTTG   TGTCA   AGGTG

CTGCC   CCGCT   TGGAA   TCCCG   AATTA   ACAAG   GCAGA   GTGGT   CGGAG   GAGCA

GTGTT   TACTT   ATCAC   GACGG   AGCAG   TATTT   CACTG   TGACC   AACCT   GAGCA

TCTTA   GTCAT   ATCTA   TGCTG   CTATT   CTGTG   GAATC   CTGGT   CTGTC   TGGTT

CTCCA   GTGGT   ACATC   CGGCA   CCCGG   GGAAG   TTGCC   TACAG   TCCTG   GTCTT

CAAGA   AGCCT   CACGA   CTTCT   TCCCA   GCCAA   CCCTC   TCTGC   CCAGA   AACTC

CCGAT   GCCAT   TCACA   TCGTG   GACCT   GGAGG   TTTTC   CCAAA   GGTGT   CACTA

TABLE 3-continued

Nucleotide and predicted amino acid sequence
derived from a mouse cDNA encoding an IL-10 receptor component.
Lower case positions have not been verified in both directions
of the double stranded nuceic acid. The initiation codon starts
at nucleotide 61.

GAGCT GAGAG ACTCA GTCCT GCATG GCAGC ACCGA CAGTG GCTTT GGCAG
TGGTA AACCA TCACT TCAGA CTGAA GAGTC CCAAT TCCTC CTCCC TGGCT
CCCAC CCCCA GATAC AGGGG ACTCT GGGAA AAGAA GAGTC TCCAG GGCTA
CAGGC CACCT GTGGG GACAA CACGG ACAGT GGGAT CTGCC TGCAG GAGCC
CGGCT TACAC TCCAG CATGG GGCCC GCCTG GAAGC AGCAG CTTGG ATATA
CCCAT CAGGA CCAGG ATGAC AGTGA CGTTA ACCTA GTCCA GAACT CTCCA
GGGCA GCCTA AGTAC ACACA GGATG CATCT GCCTT GGGCC ATGTC TGTCT
CCTAG AACCT AAAGC CCCTG AGGAG AAAGA CCAAG TCATG GTGAC ATTCC
AGGGC TACCA GAAAC AGACC AGATG GAAGG CAGAG GCAGC AGGCC CAGCA
GAATG CTTGG ACGAA GAGAT TCCCT TGACA GATGC CTTTG ATCCT GAACT
TGGGG TACAC CTGCA GGATG ATTTG GCTTG GCCTC CACCA GCTCT GGCCG
CAGGT TATTT GAAAC AGGAG TCTCA AGGGA TGGCT TCTGC TCCAC CAGGG
ACACC AAGTA GACAG TGGAA TCAAC TGACC GAAGA GTGGT CACTC CTGGG
TGTGG TTAGC TGTGA AGATC TAAGC ATAGA AAGTT GGAGG TTTGC CCATA
AACTT GACCC TCTGG ACTGT GGGGC AGCCC CTGGT GGCCT CCTGG ATAGC
CTTGG CTCTA ACCTG GTCAC CCTGC CGTTG ATCTC CAGCC TGCAG GTAGA
AGAAT GACAG CGGCT AAGAG TTATT TGTAT TCCAG CCATG CCTGC TCCCC
TCCCT GTACC TGGGA GGCTC AGGAG TCAAA GAAAT ATGTG GGTCC TTTTC
TGCAG ACCTA CTGTG ACCAG CTAGC CAGGC TCCAC GGGGC AAGGA AAGGC
CATCT TGATA CACGA GTGTC AGGTA CATGA GAGGT TGTGG CTAGT CTGCT
GAGTG AGGGT CTGTA GATAC CAGCA GAGCT GAGCA GGATT GACAG AGACC
TCCTC ATGCC TCAGG GCTGG CTCCT ACACT GGAAG GACCT GTGTT TGGGT
GTAAC CTCAG GGCTT TCTGG ATGTG GTAAG ACTGT AGGTC TGAAG TCAGC
TGAGC CTGGA TGTCT GCGGA GGTGT TGGAG TGGCT AGCCT GCTAC AGGAT
AAAGG GAAGG CTCAA GAGAT AGAAG GGCAG AGCAT GAGCC AGGTT TAATT
TTGTC CTGTA GAGAT GGTCC CCAGC CAGGA TGGGT TACTT GTGGC TGGGA
GATCT TGGGG TATAC ACCAC CCTGA ATGAT CAGCC AGTCA ATTCA GAGCT
GTGTG GCAAA AGGGA CTGAG ACCCA GAATT TCTGT TCCTC TTGTG AGGTG
TCTCT GCTAC CCATC TGCAG ACAGA CATCT TCATC TTTTT ACTAT GGCTG
TGTCC CCTGA ATTAC CAGCA GTGGC CAAGC CATTA CTCCC TGCTG CTCAC
TGTTG TGACG TCAGA CCAGA CCAGA CGCTG TCTGT CTGTG TTAGT ACACT
ACCCT TTAGG TGGCC TTTGG GCTTG AGCAC TGGCC CAGGC TTAGG ACTTA
TGTCT GCTTT TGCTG CTAAT CTCTA ACTGC AGACC CAGAG AACAG GGTGC
TGGGC TGACA CCTCC GTGTT CAGCT GTGTG ACCTC CGACC AGCAG CTTCC
TCAGG GGACT AAAAT AATGA CTAGG TCATT CAGAA GTCCC TCATG CTGAA
TGTTA ACCAA GGTGC CCCTG GGGTG ATAGT TTAGG TCCTG CAACC TCTGG
GTTGg AAGGA AGTGG ACTAC GGAAG CCATC TGTCC CCCTg GGGAG CTTCC
ACCTC ATGCC AGTGT TTCAG AGATC TTGTG GGAGC CTAGG GCCTT GTGCC
AAGGG AGCTG CTAGT CCCTG GGGTC TAGGG CTGGT CCCTG CCTCC CTATA

TABLE 3-continued

Nucleotide and predicted amino acid sequence
derived from a mouse cDNA encoding an IL-10 receptor component.
Lower case positions have not been verified in both directions
of the double stranded nuceic acid. The initiation codon starts
at nucleotide 61.

CTGCG TTTGA GACCT GTCTT CAAAT GGAGG CAGTT TGCAG CCCCT AAGCA
AGGAT GCTGA GAGAa gCAGC AAGGC TGCTG ATCCC TGAGC CCAGA GTTTC
TCTGA AGCTT TCCAA ATACA GACTG TGTGA CGGGG TGAGG CCAGC CATGA
ACTTT GGCAT CCTGC CGAGA AGGTC ATGAC CCTAA TCTGG TACGA GAGCT
CCTTC TGGAA CTGGG CAAGC TCTTT GAGAC CCCCC TGGAA CCTTT ATTTA
TTTAT TTGCT CACTT ATTTA TTGAG GAAGC AGCGT GGCAC AGGCG GAAGG
CTCTG GGTCT CTCAG GAGGT CTAGA TTTGC CTGCC CTGTT TCTAG CTGTG
TGACC TTGGG CAAGT CACGT TTCCT CGTGG AGCCT CAGTT TTCCT GTCTG
TATGC AAAGC TTGGA AATTG AAATG TACCT GACGT GCTCC ATCCC TAGGA
GTGCT GAGTC CCACT GAGAA AGCGG GCACA GACGC CTCAA ATGGA ACCAC
AAGTG GTGTG TGTTT TCATC CTAAT AAAAa gtcag gtgtt ttgcg gaaaa
aaaaa aaaaa aaaaa aaaaa amino acid sequence:
MLSRL LPFLV TISSL SLEFI AYGTE LPSPS YVWFE ARFFQ HILHW KPIPN
QSEST YYEVA LKQYG NSTWN DIHIC RKAQA LSCDL TTFTL DLYHR SYGYR
ARVRA VDNSQ YSNWT TTETR FTVDE VILTV DSVTL KAMDG IIYGT IHPPR
PTITP AGDEY EQVFK DLRVY KISIR RFSEL KNATK RVKQE TFTLT VPIGV
RKFCV KVLPR LESRI NKAEW SEEQC LLITT EQYFT VTNLS ILVIS MLLFC
GILVC LVLQW YIRHP GKLPT VLVFK KPHDF FPANP LCPET PDAIH IVDLE
VFPKV SLELR DSVLH GSTDS GFGSG KPSLQ TEESQ FLLPG SHPQI QGTLG
KEESP GLQAT CGDNT DSGIC LQEPG LHSSM GPAWK QQLGY THQDQ DDSDV
NLVQN SPGQP KYTQD ASALG HVCLL EPKAP EEKDQ VMVTF QGYQK QTRWK
AEAAG PAECL DEEIP LTDAF DPELG VHLQD DLAWP PPALA AGYLK QESQG
MASAP PGTPS RQWNQ LTEEW SLLGV VSCED LSIES WRFAH KLDPL DCGAA
PGGLL DSLGS NLVTL PLISS LQVEE

TABLE 4

Comparison of the human and mouse IL-10 receptor
subunits at the nucleotide and amino acid levels.

nucleotide; mouse above, human below

```
  1  C C A T T G T G C T G G A A A G C A G G A C G C G C C G G C C G G A G G C G T A A A G G C C G . . .   47
                          | |   | | | | | | |         | | | | | |
  1  . . . . . . . . . . . . . . . . . . . . . . . . A A A G A G C T G G A G G C G C G C A G G C C G G C T   27

48  . . G C T C C A G T G G A C G A T G C C G C T G T G C G C C C A G G A T G T T G T C G C G T T T G C   95
        | | | | | |   |       | |     | |     | |   | | | | | | | | | | | |   | |     | |         |
 28  C C G C T C C G G C C C C G G A C G A T G C G G C G C G C C C A G G A T G C T G C C G T G C C T C G   77

96  T C C C A T T C C T C G T C A C G A T C T C C A G C C T G A G C C T A G A A T T C A T T G C A T A C  145
     |         | | |   |       | |   | |     | | | | | |     | | |     |         | |   |
 78  T A G T G C T G C T G G C G G C G C T C C T C A G C C T C C G T C T T G G C T C A G A C G C T C A T  127
```

TABLE 4-continued

Comparison of the human and mouse IL-10 receptor subunits at the nucleotide and amino acid levels.

```
146  GGGACAGAACTGCCAAGCCCTTCCTATGTGTGGTTTGAAGCCAGATTTTT  195
     ||||||||  |||||  ||||||  ||  |  |||||||||||     ||||||
128  GGGACAGAGCTGCCCAGCCCTCCGTCTGTGTGGTTTGAAGCAGAATTTTT  177

196  CCAGCACATCCTCCACTGGAAACCTATCCCAAACCAGTCTGAGAGCACCT  245
     |||  |||||||||||||||||  |||  ||||||||  ||||||||  ||  ||||
178  CCACCACATCCTCCACTGGACACCCATCCCAAATCAGTCTGAAAGTACCT  227

246  ACTATGAAGTGGCCCTCAAACAGTACGGAAACTCAACCTGGAATGACATC  295
     ||||||||||||  |||     |||  ||||          |||||||     ||||
228  GCTATGAAGTGGCGCTCCTGAGGTATGGAATAGAGTCCTGGAACTCCATC  277

296  CATATCTGTAGAAAGGCTCAGGCATTGTCCTGTGATCTCACAACGTTCAC  345
     |  |||||||         |||  |   ||||||||  |||   ||   ||    |   ||
278  TCCAACTGTAG......CCAGACCCTGTCCTATGACCTTACCGCAGTGAC  321

346  CCTGGATCTGTATCACCGAAGCTATGGCTACCGGGCCAGAGTCCGGGCAG  395
     |  ||||  |||||   |||      |||  |||||||||||||||||||||  ||||||  |
322  CTTGGACCTGTACCAC...AGCAATGGCTACCGGGCCAGAGTGCGGGCTG  368

396  TGGACAACAGTCAGTACTCCAACTGGACCACCACTGAGACTCGCTTCACA  445
     |||||     |||  |  |  |  |||||||||||||||     |||     |  ||  |||||||  |
369  TGGACGGCAGCCGGCACTCCAACTGGACCGTCACCAACACCCGCTTCTCT  418

446  GTGGATGAAGTGATTCTGACAGTGGATAGCGTGACTCTGAAAGCAATGGA  495
     ||||||||||||  |||||||||||||||     |||     ||     |    |
419  GTGGATGAAGTGACTCTGACAGTTGGCAGTGTGAACCTAGAGATCCACAA  468

496  CGGCATCATCTATGGACAATCCATCCCCCCAGGCCCACGATAACCCCTG   545
     |||  ||||||     ||||     ||  ||  |    |||||||||||  |||    |||||  |
469  TGGCTTCATCCTCGGGAAGATTCAGCTACCCAGGCCCAAGATGGCCCCG   518

546  CAGGGGATGAGTACGAACAAGTCTTCAAGGATCTCCGAGTTTACAAGATT  595
     |     ||     ||  |||       ||||||     |     ||||||     ||     |||||
519  CGAATGACACATATGAAAGCATCTTCAGTCACTTCCGAGAGTATGAGATT  568

596  TCCATCCGGAAGTTCTC...AGAACTAAAGAATGCAACCAAGAGAGTGAA  642
     ||||  ||  |||  |  |     |     |  |  |     |  |     ||  |||||  |||  ||
569  GCCATTCGCAAGGTGCCGGGAAACTTCACGTTCACACACAAGAAAGTAAA  618

643  ACAGGAAACCTTCACCCTCACGGTCCCCATAGGGGTGAGAAAGTTTTGTG  692
     |||  ||||  |||||  ||||     |  |    ||  |||  ||  ||||  ||||
619  ACATGAAAACTTCAGCCTCCTAACCTCTGGAGAAGTGGGAGAGTTCTGTG  668

693  TCAAGGTGCTGCCCCGCTTGGAATCCCGAATTAACAAGGCAGAGTGGTCG  742
     ||  ||||||     ||     |  |  ||||||||  ||||||||     ||||||
669  TCCAGGTGAAACCATCTGTCGCTTCCCGAAGTAACAAGGGGATGTGGTCT  718

743  GAGGAGCAGTGTTTACTTATCACGACGGAGCAGTATTTCACTGTGACCAA  792
     |  |||  ||||     |     |||||  |     |||||||||||||  ||||||||
719  AAAGAGGAGTGCATCTCCCTCACCA...GGCAGTATTTCACCGTGACCAA  765

793  CCTGAGCATCTTAGTCATATCTATGCTGCTATTCTGTGGAATCCTGG...  839
     |  |  |  |||||||     |||     |  |||||||  |||     |||     |
766  CGTCATCATCTTCTTTGCCTTTGTCCTGCTGCTCTCCGGAGCCCTCGCCT  815

840  TCTGTCTGGTTCTCCAGTGGTACATCCGGCACCCGGGGAAGTTGCCTACA  889
     |||  ||||     ||||||     |||     |  ||||  ||     ||||     |  |||  |
816  ACTGCCTGGCCCTCCAGCTGTATGTGCGGCGCCGAAAGAAGCTACCCAGT  865

890  GTCCTGGTCTTCAAGAAGCC...TCACGACTTCTTCCCAGCCAACCCTCT  936
     ||||||  |||||||||||||     |  |  |  ||||||     |  |  |  ||
866  GTCCTGCTCTTCAAGAAGCCCAGCCCCTTCATCTTCATCAGCCAGCGTCC  915

937  CTGCCCAGAAACTCCCGATGCCATTCACATCGTGGACCTGGAGGTTTTCC  986
     ||  |||||||||  ||  |  ||  ||||  |||  |  ||  ||||||  ||
916  CTCCCCAGAGACCCAAGACACCATCCACCCGCTTGATGAGGAGGCCTTTT  965
```

TABLE 4-continued

Comparison of the human and mouse IL-10 receptor subunits at the nucleotide and amino acid levels.

```
 987  CAAAGGTGTCACTAGAGCTGAGAGACTCAGTCCTGCATGGCAGCACCGAC  1036
      ||||||||  |  |||||||||   |||  |  ||||||  ||||||||  |||
 966  TGAAGGTGTCCCCAGAGCTGAAGAACTTGGACCTGCACGGCAGCACAGAC  1015

1037  AGTGGCTTTGGCAGTGGTAAACCATCACTTCAGACTGAAGAGTCCCAATT  1086
      |||||||||||||||   ||  ||||||  ||  ||||||||||||||||  ||||  ||
1016  AGTGGCTTTGGCAGCACCAAGCCATCCCTGCAGACTGAAGAGCCCCAGTT  1065

1087  CCTCCTCCCTGGCTCCCACCCCCAGATACAGGGGACTCTGGGAAAAGAAG  1136
      ||||||||||||  ||  |||||||||    |   |  ||  ||||||||  |   |
1066  CCTCCTCCCTGACCCTCACCCCCAGGCTGACAGAACGCTGGGAAACGGGG  1115

1137  AGTCTCCAGGGCTACAGGCCACCT............GTGGGGACAACACG  1174
      ||  |  |||  |||    ||  ||  ||                |  |   |   |||
1116  AGCCCCCTGTGCTGGGGGACAGCTGCAGTAGTGGCAGCAGCAATAGCACA  1165

1175  GACAGTGGGATCTGCCTGCAGGAGCCCGGCTTACACTCCAGCATGGGGCC  1224
      |||||  |||||||||||||||||||||||||||  ||   |  |||||||  |||||
1166  GACAGCGGGATCTGCCTGCAGGAGCCCAGCCTGAGCCCCAGCACAGGGCC  1215

1225  CGCCTGGAAGCAGCAGCTTGGATATACCCATCAGGACCAGGATGACAGTG  1274
      |  |||||  ||||   |||   |  ||    |  |    ||  ||||||||||||||||
1216  CACCTGGGAGCAACAGGTGGGGAGCAACAGCAGGGGCCAGGATGACAGTG  1265

1275  ACGTTAACCTAGTCCAGAACTCTCCAGGGCAGCCTAAGTACACACAGGAT  1324
      |  ||  ||  ||||  ||  ||||||   |   |   ||||||||  |
1266  GCATTGACTTAGTTCAAAACTCTGAGGGCCGGGCTGGGGACACACAGGGT  1315

1325  GCATCTGCCTTGGGCCATGTCTGTCTCCTAGAACCTAAAGCCCCTGAGGA  1374
      |  ||  |||||||||||||     |  |||  ||    ||  |||  ||      ||||  |||
1316  GGCTCGGCCTTGGGCCACCACAGTCCCCCGGAGCCTGAGGTGCCTGGGGA  1365

1375  GAAAGACCAAGTCATGGTGACATTCCAGGGCTACCAGAAACAGACCAGAT  1424
      ||||||  ||     |||  ||||||||||  ||||  ||   ||||||||||
1366  AGAAGACCCAGCTGCTGTGGCATTCCAGGGTTACCTGAGGCAGACCAGAT  1415

1425  GGAAGGCAGAGGCAGCAGGCCCAGCAGAATGCTTGGACGAAGAGATTCCC  1474
      |    |  ||||      |||    |   |||  |||  ||||| |||||        |||
1416  GTGCTGAAGAGAAGGCAACCAAGACAGGCTGCCTGGAGGAAGAATCGCCC  1465

1475  TTGACAGATGCCTTTGATCCTGAACTTGGGGTACACCTGCAGGATGATTT  1524
      ||||||||| | |||  ||    ||   |  |||   |    ||||      |||||
1466  TTGACAGATGGCCTTGGCCCCAAATTCGGGAGATGCCTGGTTGATGAGGC  1515

1525  GGCTTGGCCTCCACCAGCTCTGGCCGCAGGTTATTTGAAACAGGAGTCTC  1574
      |   ||  |||||||||||  ||||||  ||  ||||||||||||||  |||
1516  AGGCTTGCATCCACCAGCCCTGGCCAAGGGCTATTTGAAACAGGATCCTC  1565

1575  AAGGGATGGCTTCTGCTCCACCAGGGACACCAAGTAGACAGTGGAATCAA  1624
      ||   |||  ||    |||  |   |||||  |   ||||       |||||||||||  ||
1566  TAGAAATGACTCTGGCTTCCTCAGGGGCCCCAACGGGACAGTGGAACCAG  1615

1625  CTGACCGAAGAGTGGTCACTCCTGGGTGTGGTTAGCTGTGAAGATCTAAG  1674
      |   ||  ||  ||||||||||||||   ||  |||||     ||  |  |
1616  CCCACTGAGGAATGGTCACTCCTGGCCTTGAGCAGCTGCAGTGACCTGGG  1665

1675  CATAGAAAGTTGGAGGTTTGCCCATAAACTTGACCCTCTGGACTGTGGGG  1724
      |||          |||||  |||||||||  |  ||||  ||||||  |  ||||||  ||
1666  AATATCTGACTGGAGCTTTGCCCATGACCTTGCCCCTCTAGGCTGTGTGG  1715

1725  CAGCCCCTGGTGGCCTCCTGGATAGCCTTGGCTCTAACCTGGTCACCCTG  1774
      |||||||  |||||  |||||||   |||  ||  |||  ||||||||||||||||
1716  CAGCCCCAGGTGGTCTCCTGGGCAGCTTTAACTCAGACCTGGTCACCCTG  1765

1775  CCGTTGATCTCCAGCCTGCAGGTAGAAGAATGACAGCGGCTAAGAG..TT  1822
      ||  |  ||||||  ||||||||||     |  ||  ||||     ||||  ||||    |
1766  CCCCTCATCTCTAGCCTGCAGTCAAGTGAGTGACTCGGGCTGAGAGGCTG  1815
```

TABLE 4-continued

Comparison of the human and mouse IL-10 receptor
subunits at the nucleotide and amino acid levels.

```
1823  A T T T G T A T T C C A G C C A T G C C T G C T C C C C T C C C T G T A C C T G G G A G G C T C A G  1872
      | | |       | | |     | | | | | | | | | | | | | | | |     | |     | | | |     | | |     | |     | |
1816  C T T T T G A T T T T A G C C A T G C C T G C T C C T C T G C C T G G A C C A G G A G G A G G G C C  1865

1873  G A G T C A A A G A A A T . . . . . . . . . . . . . . . A T G T G G G T C C T T T T C T G C A G A C C T  1909
      |         | | | | |                                     |   | | | |     | | | | | | | | | | |         |
1866  C T G G G G C A G A A G T T A G G C A C G A G G C A G T C T G G G C A C T T T T C T G C A A G T C C  1915

1910  A C T G . . . . . . . . . . . . . . . . . . T G A C C A G C T A G C C A G G C T C C A C G G G G C A  1941
      | | | |                                     | |         | | |   |   | | | |   |           | | | | | |
1916  A C T G G G G C T G G C C C A G C C A G G C T G C A G G G C T G G T C A G G G T G T C T G G G G C A  1965

1942  A G G A A A G G C C A T C T T G A T A C A C G A G T G T C A G G T A C A T G A G A G G T T G T G . G  1990
      |         | | | | | | | | |     |         | |   | | | |       | | | |       | |       | |           |
1966  G G A G G A G G C C A A C T C A C T G A A C T A G T G C A G G G T A T G T G G G T G G C A C T G A C  2015

1991  C T A G T C T G C T G A G T G A G G G T C T G T A G A T A C C A G C A G A G C T G A G C A G G A T T  2040
      | |         | | | |     | | |       | |   | |       | | |     | | |         |       | | | | | | | | | | |     | |
2016  C T G T T C T G T T G A C T G G G G C C C T G C A G A C T C T G G C A G A G C T G A G A A G . . . .  2061

2041  G A C A G A G A C C T C C T C A T G C C T C A G G G C T G G C T C C T A C A . C T G G A A G G A C C  2089
      |   | | |     | | | | |     | | |             | | |     |     | |         | | | |     | |           | | | | |
2062  G G C A G G G A C C T T C T C C C T C C T A G G A A C T C T T T C C T G T A T C A T A A A G G A T T  2111

2090  T G T G T T T G G G T G T A A C C T C A G G G C T T T C T G G A . . T G T G G T A A G A C T G T A G  2137
      |     |       | | | |               | | | | | | | | | | | | |         | | | | | | |     | | |           |
2112  A T T T G C T C A G G G G A A C C A T G G G G C T T T C T G G A G T T G T G G T G A G G C C A C C A  2161

2138  G T C T G A A G T C A G C T G A G . C C T G G A T G T C T G C G G A G G T G T T G G A G T G G C T A  2186
      |   | | | | | | | | | | | | |     | |     | |       | |       | |       |                 |                 | |
2162  G G C T G A A G T C A G C T C A G A C C C A G A C C T C C C T G C T T A G G C C A C T C G A G C A T  2211

2187  G C C T G C T A C A G G A T A A A G G G A A G G C T C A A G A G A T A G A A G . . G G C A G A G C A  2234
            | | |   |     |             | | |   |     | | | |       | |       | |   | | | |         |     |
2212  C A G A G C T T C C A G C A G G A G G A A G G G C T G T A G G A A T G G A A G C T T C A G G G C C T  2261

2235  T G A G C C A G G T T T A A T T T T . . . . . . . . . . . . . . . . . . . . . . . . G T C C T G T A  2260
      | |         | | |         | | | | | |                                                                     | | |         |
2262  T G C T G C T G G G G T C A T T T T T A G G G G A A A A A G G A G G A T A T G A T G G T C A C A T G  2311

2261  G A G A T G G T C C C . . . . . . . . . C A G C C A G G A T G G G T T A C T T G T G G C T G G G A G  2301
      |     | |         | | | |                   |       |   | |         | |     | | | | |     | | | |     | |
2312  G G G A A C C T C C C C T C A T C G G G C C T C T G G G G C A G G A A G C T T G T C A C T G G A A G  2361

2302  A T C T T G G G G T A T A . . . . . . C A C C A C C C T G A A T G A T C A G C C A G T C A A T T C A  2345
      | | | | |       | | | | | |               |       | |   | |   | |         |     | |       | | | | |
2362  A T C T T A A G G T A T A T A T T T T C T G G A C A C T C A A A C A C A T C A T A A T G G A T T C A  2411

2346  G A G C T G T G T G G C A A A A G G G A C T G A G A C C C A G A A T T T C T G T T C C T C T T G T G  2395
            |     | |     |     | | | |     | |       |     | | | | | | | |   | |         | | | |       |     |
2412  C T G A G G G G A G A C A A A G G G A G C C G A G A C C C T G G A T G G G G C T T C C A G C T C A G  2461

2396  A . . . . . . . . . . . . . . . . G G T G T C T C T G C T A C C C A T C T G C A G A C A G A C A T C  2429
      |                                 | | |         | | | | |       | | | | | | | | | | |   |     |         |
2462  A A C C C A T C C C T C T G G T G G G T A C C T C T G G C A C C C A T C T G C A A A T A T C T C C C  2511

2430  T T C A T C T T T T T A C T A T G G C T G T G T . C C C C T G A A T T A C C A G C A G T G G C C A A  2478
      |   | |             |   |     |   |       | | | | | |             | |     | |   | | | | | |
2512  T C T C T C C A A C A A A T G G A G T A G C A T C C C C C T G G G G C A C T T G C T G A G G C C A A  2561

2479  G C C A T T . . . . . . . . . . A C T C C C T G C T G C T C A C T G T T G T G A C G T C A G A C C A  2518
      | | | |   |                         |       | | | |     | |     | | | |                 | | |
2562  G C C A C T C A C A T C C T C A C T T T G C T G C C C C A C C A T C T T G C T G A C A A C T T C C A  2611

2519  G A C C A G A C . . . G C T G T C T G T C T G T G T T A G T A C A C T A C C C T T T A G G T G G C C  2565
      |   | | |   |         |   |   | | |   |   | |   |       | |     | |     | | | | | |     | |   | | | |
2612  G A G A A G C C A T G G T T T T T T G T A T T G G T C A T A A C T C A G C C C T T T G G G C G G C C  2661
```

TABLE 4-continued

Comparison of the human and mouse IL-10 receptor
subunits at the nucleotide and amino acid levels.

```
2566  T T T G G G C T T G A G C A C T G G C C C A . . . . . . . . . . . . . . . . . . . . . G G C T T A G G  2595
      | | | | | | | | |   | | | |     | |   | |                                             | |   | |
2662  T C T G G G C T T G G G C A C C A G C T C A T G C C A G C C C C A G A G G G T C A G G G T T G G A G  2711

2596  A C T T A T G T C T G C T T T T G C T G C T A A T C T C T A A C T G C A G A C C C A G A G A A C A G  2645
        |   |   | |     | |       | | | | | | | | | | | | |   | |   |   | |   | | | | | | | | | | |   |   |
2712  G C C T G T G C T T G T G T T T G C T G C T A A T G T C C A G C T A C A G A C C C A G A G G A T A A  2761

2646  G G T G C T G G G . . . . . . . . . . . . . . . . . C T G A C A C C T C C G T G T T C A G C T G T G T  2679
           | | | | |                                       | | |   |       |   | | | | | | | | | | | | | | |
2762  G C C A C T G G G C A C T G G G C T G G G G T C C C T G C C T T G T T G G T G T T C A G C T G T G T  2811

2680  G A C C T C C G A C C A G C A G C T T C C T C A G G G G A C T A A A A T A A T G A C T A G G T C A T  2729
      | |   |   | | |   | | |       | | |             | | |   | |   | |                     |     |
2812  G A T T T G G A C T A G C C A C T T G T C A G A G G G C C T C A A T C T C C C A T C T G T G A A A  2861

2730  T C A G A A G T C C C T C A T G C T G A A T G T T A A C C A A G G T G C C C C T G G G G T G A T A G  2779
      | | | |         | | |       | |   | |   |   |     | | |       | |               | | | |     | | |
2862  T A A G G A . . . . C T C C A C C T T T A G G G G A C C C T C C A T G T T T G C T G G G T A T T A G  2907

2780  T T T A G G T C C T G C A A C C T C T G G G T T G G A A G G A A G T G G A C T A C G G A A G C C A T  2829
            | |   |     | |   |                             | |   | |             |                 | |
2908  C C A A G C T G G T C C . . . . . . . . . . . . . . . . T G G G A G A A T G C A G A T A C T G T C C G  2942

2830  C T G T C C C C C T G G G G A G C T T C C A C C T C A T G C C A G T G T T T C A G A G A T C T T G T  2879
            |     | |       | | | |           | |   | |       |   |   | | | | |   |
2943  T G G A C T A C C A A G C T G G C T T G T T T C T T A T G C C A G A G G C T A A C A G A T C C A A T  2992

2880  G G G A G C C T A G G G C C T T G T G C C A A G G G A G C T G C T A G T C C C T G G G G T C T A G G  2929
      | | | | |   |   |   | |     |     | | | | | | | |     | |     |           |                 | | |
2993  G G G A G T C C A T G G T G T C A T G C C A A G A C A G T A T C A G A C A C A G C C C C A G A A G G  3042

2930  G . . . . . . C T G G T C C C T G C C T C C C T A T A C T G C G T T T G A G A C C T G T C T T C A A  2973
      |             | | |   | | | | | | | | | | |   | | |         |   | | | |         | | |   | | | | | |
3043  G G G C A T T A T G G G C C C T G C C T C C C C A T A G G C C A T T T G G A C T C T G C C T T C A A  3092

2974  A T G G A G G C A G T T T G C A G C C C C T A A G C A A G G A T G C T G A G A G A A G C A G C A A G  3023
      |       | | | | | | | | |         | | |   | |     |   | | |     | | |     | | | |     | | |     |
3093  A C A A A G G C A G T T . . C A G T C C A C A G G C A T G G A A G C T G T G A G G G G A C A G G C C  3140

3024  G C T G C . . . . . . . . . . . T G A T C C C T G A G C C C A G A G T T T C T C T G A A G C T T T C  3062
        | | |                         |         | |   | | | | | |   |       | | | | | | | | |   | | |     | | |
3141  T G T G C G T G C C A T C C A G A G T C A T C T C A G C C C T G C C T T T C T C T G G A G C A T T C  3190

3063  C A A A T A C A G A C T G T G T G A C G G G G T G A G G C C A G C C A T G A A C T T T G G C A T C C  3112
            | |   | | | | | |         |       | | |       |   | | |   | | | | | | | | | | |         |         |
3191  T G A A A A C A G A T A T T C T G G C C C A G G G A A T C C A G C C A T G A C C C C C A C C C C T C  3240

3113  T G C C G A G A A G G T C A T . G A C C C T A A T C T G G T A C G A G A G C T C C T T C T G G A A C  3161
      | | | |   |             | | |   |       |   |         | |   | | | | | | | |       | |   | | | |   | | | | | |
3241  T G C C A A A G T A C T C T T A G G T G C C A G T C T G G T A A C T G A A C T C C C T C T G G A G G  3290

3162  T G G G C A A G . . . . . . . . C T C T T T G A G A C C C C C C T G G A A C C T T T A T T T A T T T  3203
            | | |                             | | |         | |   | |     | |       | |   | | | | | | | | | | |
3291  C A G G C T T G A G G G A G G A T T C C T C A G G G T T C C C T T G A A A G C T T T A T T T A T T T  3340

3204  A . T T T G C T C A C T T A T T T A T T G A G G A A G C A G C G T G G C A C A G G C G C A A G G C T  3252
          | | | |   | | |   | | | | | | | | | | |         | |   | | | | |   |   | | | | | | |             |         |
3341  A T T T T G T T C A T T T A T T T A T T G G A G A G G C A G C A T T G C A C A G T G A A A G A A T T  3390

3253  C T G G G T C T C T C A G G A G . . . . . . . . G T C T A G A T T T G C C T G C C C T G T T T C T A  3294
      | | | |   |   | | | | | | | | |                 | | | | |   |     | |   | |     | | | | | | | |       |
3391  C T G G A T A T C T C A G G A G C C C C G A A A T T C T A G C T C T G A C T T T G C T G T T T C C A  3440

3295  G C T G T G T G A C C T T G G G C A A G T C A C G T T T C C T C G T G G A G C C T C A G T T T T C C  3344
      |   | |   | | | | | | | | | |     | | | | | | | |   |   | | | | |   | | | | | | | | | | | | | | | |       |
3441  G T G G T A T G A C C T T G G A G A A G T C A C T T A T C C T C T T G G A G C C T C A G T T T C C T  3490
```

TABLE 4-continued

Comparison of the human and mouse IL-10 receptor subunits at the nucleotide and amino acid levels.

```
3345  T G T C T G T A T G C A A A G C T T G G A A A T T G A A A T G T A C C T G A C G T G C T C C A T C C  3394
      | | | |   |           | |         | |   |             |       |           | |               | |
3491  C A T C T G C A G A A T A A T G A C T G A C T T G T C T A A T T C A T A G G G A T G T G A G G T T C  3540

3395  C T A G G A G T G C T G A G T C C C A C T G A G A A A G C G G G C A C A G A C G C C T C A A A T G G  3444
      | | | | | | |                         |           |   | |             | |         |   | |   |
3541  . . . . . . . T G C T G A G G A A A T G G G T A T G A A T G T G C C T T G A A C A C A A A G C T C T  3583

3445  A A C C A C A A G T G G T G T G T G . T T T T C A T C C T A A T A A A A A G T C A G G T G T T T T G  3493
      |   |   | | | | | |   |       | |   | | | |   | |   |   | | | | | | |       | | | |   |
3584  G T C A A T A A G T G A T A C A T G T T T T T T A T T C C A A T A A A T T G T C A A G A C C A C A .  3632
``` nucleotide; coding region; mouse above, human below

```
 80   A T G T T G T C G C G T T T G C T C C C A T T C C T C G T C A C G A T C T C C A G C C T G A G C C T  129
      | | |     | |   | |     |       |             |   | | |       | |   | |   | | | | | |     |   | |
 62   A T G C T G C C G T G C C T C G T A G T G C T G C T G G C G G C G C T C C T C A G C C T C C G T C T  111

130   A G A A T T C A T T G C A T A C G G G A C A G A A C T G C C A A G C C C T T C C T A T G T G T G G T  179
      |     |             | |       |   | | | | | | | | |   | | | | |   | | | | | | |     |   | | | | | | | |
112   T G G C T C A G A C G C T C A T G G G A C A G A G C T G C C C A G C C C T C C G T C T G T G T G G T  161

180   T T G A A G C C A G A T T T T T C C A G C A C A T C C T C C A C T G G A A A C C T A T C C C A A A C  229
      | | | | | | |                 | | | | | | | | |   | | | | | | | | | | | | | | | | | | |   | | |   | | | | | | | |
162   T T G A A G C A G A A T T T T T C C A C C A C A T C C T C C A C T G G A C A C C C A T C C C A A A T  211

230   C A G T C T G A G A G C A C C T A C T A T G A A G T G G C C C T C A A A C A G T A C G G A A A C T C  279
      | | | | | | | |     | |     | | | |     | | | | | | | | | | | | |   | | |             | | |     | | | |
212   C A G T C T G A A A G T A C C T G C T A T G A A G T G G C G C T C C T G A G G T A T G G A A T A G A  261

280   A A C C T G G A A T G A C A T C C A T A T C T G T A G A A A G G C T C A G G C A T T G T C C T G T G  329
      |   | | | | | |         | | | |           |   | | | | | |                       | | |   |       | | | | | |     | |
262   G T C C T G G A A C T C C A T C T C C A A C T G T A G . . . . . . C C A G A C C C T G T C C T A T G  305

330   A T C T C A C A A C G T T C A C C C T G G A T C T G T A T C A C C G A A G C T A T G G C T A C C G G  379
      |     | |     | |       |         | | |       | | | |         | | | | |       | | |         | | |   | | | | | | | | | | |
306   A C C T T A C C G C A G T G A C C T T G G A C C T G T A C C A C . . . A G C A A T G G C T A C C G G  352

380   G C C A G A G T C C G G G C A G T G G A C A A C A G T C A G T A C T C C A A C T G G A C C A C C A C  429
      | | | | | | | |           | | | | |         | | | | | |         | | |   |     |     | | | | | | | | | | | | |           | | |
353   G C C A G A G T G C G G G C T G T G G A C G G C A G C C G G C A C T C C A A C T G G A C C G T C A C  402

430   T G A G A C T C G C T T C A C A G T G G A T G A A G T G A T T C T G A C A G T G G A T A G C G T G A  479
      |     | |   | | | | | |     | | | | | | | | | | | | | |     | | | | | | | | | |           | |     | | | |
403   C A A C A C C C G C T T C T C T G T G G A T G A A G T G A C T C T G A C A G T T G G C A G T G T G A  452

480   C T C T G A A A G C A A T G G A C G G C A T C A T C T A T G G G A C A A T C C A T C C C C C C A G G  529
      |   |   |                     |   | | |     | | | | |         | | | |     | |     | |     |         | | | | | |
453   A C C T A G A G A T C C A C A A T G G C T T C A T C C T C G G G A A G A T T C A G C T A C C C A G G  502

530   C C C A C G A T A A C C C C T G C A G G G G A T G A G T A C G A A C A A G T C T T C A A G G A T C T  579
      | | | |   | | |         | | | |     | |             | |         | |   | | |         | | | | | |     |   |
503   C C C A A G A T G G C C C C C G C G A A T G A C A C A T A T G A A A G C A T C T T C A G T C A C T T  552

580   C C G A G T T T A C A A G A T T T C C A T C C G G A A G T T C T C . . . A G A A C T A A A G A A T G  626
      | | | | |       | |               | | | | |     | | | |     | |   | | |           | |           | |
553   C C G A G A G T A T G A G A T T G C C A T T C G C A A G G T G C C G G G A A A C T T C A C G T T C A  602

627   C A A C C A A G A G A G T G A A A C A G G A A A C C T T C A C C C T C A C G G T C C C C A T A G G G  676
      | |       | | | | |     | | |     | | | | |     | | | |     | | | | |     | | | |             | |         | |
603   C A C A C A A G A A A G T A A A A C A T G A A A C T T C A G C C T C C T A A C C T C T G G A G A A  652

677   G T G A G A A A G T T T T G T G T C A A G G T G C T G C C C C G C T T G G A A T C C C G A A T T A A  726
      | | |     | |     | | | |   | | | | | |   | | | | |       | |                   |   |   | | | | | | | |   | | |
653   G T G G G A G A G T T C T G T G T C C A G G T G A A A C C A T C T G T C G C T T C C C G A A G T A A  702

727   C A A G G C A G A G T G G T C G G A G G A G C A G T G T T T A C T T A T C A C G A C G G A G C A G T  776
      | | | | |                 | | | | | |     | |   | | | | | | | | | |     |             | | | | |     |                 | | | | |
703   C A A G G G G A T G T G G T C T A A A G A G G A G T G C A T C T C C C T C A C C A . . . G G C A G T  749
```

TABLE 4-continued

Comparison of the human and mouse IL-10 receptor subunits at the nucleotide and amino acid levels.

```
777   ATTTCACTGTGACCAACCTGAGCATCTTAGTCATATCTATGCTGCTATTC   826
      |||||||  ||||||||| |  |  ||||||  |     |  |  ||||||  ||
750   ATTTCACCGTGACCAACGTCATCATCTTCTTTGCCTTTGTCCTGCTGCTC   799

827   TGTGGAATCCTGG...TCTGTCTGGTTCTCCAGTGGTACATCCGGCACCC   873
      |    |||   |||  ||||  ||||   ||||||||   |||  |  |||||||
800   TCCGGAGCCCTCGCCTACTGCCTGGCCCTCCAGCTGTATGTGCGGCGCCG   849

874   GGGGAAGTTGCCTACAGTCCTGGTCTTCAAGAAGCC...TCACGACTTCT   920
      ||||  |  || |  ||||||| |||||||||||||  |  |   |  |||
850   AAAGAAGCTACCCAGTGTCCTGCTCTTCAAGAAGCCCAGCCCCTTCATCT   899

921   TCCCAGCCAACCCTCTCTGCCCAGAAACTCCCGATGCCATTCACATCGTG   970
      ||     |  |  || ||  ||||||  ||   ||  ||||  |||  |        |
900   TCATCAGCCAGCGTCCCTCCCCAGAGACCCAAGACACCATCCACCCGCTT   949

971   GACCTGGAGGTTTTCCCAAAGGTGTCACTAGAGCTGAGAGACTCAGTCCT   1020
      ||    |||||   ||   ||||||||| |||||||||   |||   |  ||||
950   GATGAGGAGGCCTTTTTGAAGGTGTCCCCAGAGCTGAAGAACTTGGACCT   999

1021  GCATGGCAGCACCGACAGTGGCTTTGGCAGTGGTAAACCATCACTTCAGA   1070
      |||  |||||||||  ||||||||||||||||||||    ||  |||||  ||  ||||
1000  GCACGGCAGCACAGACAGTGGCTTTGGCAGCACCAAGCCATCCCTGCAGA   1049

1071  CTGAAGAGTCCCAATTCCTCCTCCCTGGCTCCCACCCCCAGATACAGGGG   1120
      ||||||||  ||||   ||||||||||||  |  |  |||||||||    |  |
1050  CTGAAGAGCCCCAGTTCCTCCTCCCTGACCCTCACCCCCAGGCTGACAGA   1099

1121  ACTCTGGGAAAAGAAGAGTCTCCAGGGCTACAGGCCACCT..........  1160
      ||  |||||||||  |   |||  |  |  |||   ||  ||  ||
1100  ACGCTGGGAAACGGGGAGCCCCCTGTGCTGGGGGACAGCTGCAGTAGTGG   1149

1161  ..GTGGGGACAACACGGACAGTGGGATCTGCCTGCAGGAGCCCGGCTTAC   1208
        |    |    |   |||   |||||  ||||||||||||||||||||||||  ||  |
1150  CAGCAGCAATAGCACAGACAGCGGGATCTGCCTGCAGGAGCCCAGCCTGA   1199

1209  ACTCCAGCATGGGGCCCGCCTGGAAGCAGCAGCTTGGATATACCCATCAG   1258
         |  ||||||    ||||||  ||||||   ||||   |||  |  ||      |   |                |
1200  GCCCCAGCACAGGGCCCACCTGGGAGCAACAGGTGGGGAGCAACAGCAGG   1249

1259  GACCAGGATGACAGTGACGTTAACCTAGTCCAGAACTCTCCAGGGCAGCC   1308
      |  |||||||||||||||||  |  ||  ||  ||||   ||   ||||||   ||  | | |
1250  GGCCAGGATGACAGTGGCATTGACTTAGTTCAAAACTCTGAGGGCCGGGC   1299

1309  TAAGTACACACAGGATGCATCTGCCTTGGGCCATGTCTGTCTCCTAGAAC   1358
      |   |  ||||||||||  ||   ||  ||||||||||||     |  |||  ||   ||  |
1300  TGGGGACACACAGGGTGGCTCGGCCTTGGGCCACCACAGTCCCCCGGAGC   1349

1359  CTAAAGCCCCTGAGGAGAAAGACCAAGTCATGGTGACATTCCAGGGCTAC   1408
      ||  |    ||||   |||    |||||| ||     |||  ||||||||||| |||
1350  CTGAGGTGCCTGGGGAAGAAGACCCAGCTGCTGTGGCATTCCAGGGTTAC   1399

1409  CAGAAACAGACCAGATGGAAGGCAGAGGCAGCAGGCCCAGCAGAATGCTT   1458
      |  ||  |||||||||||||   |  ||||   |||  |        |||   |||  |
1400  CTGAGGCAGACCAGATGTGCTGAAGAGAAGGCAACCAAGACAGGCTGCCT   1449

1459  GGACGAAGAGATTCCCTTGACAGATGCCTTTGATCCTGAACTTGGGGTAC   1508
      |||  |||||     ||||||||||||||  |||   ||   |  |  |||    |
1450  GGAGGAAGAATCGCCCTTGACAGATGGCCTTGGCCCCAAATTCGGGAGAT   1499

1509  ACCTGCAGGATGATTTGGCTTGGCCTCCACCAGCTCTGGCCGCAGGTTAT   1558
      ||||    |||||  |     ||  ||  ||||||  ||||||     ||  |
1500  GCCTGGTTGATGAGGCAGGCTTGCATCCACCAGCCCTGGCCAAGGGCTAT   1549

1559  TTGAAACAGGAGTCTCAAGGGATGGCTTCTGCTCCACCAGGGACACCAAG   1608
      ||||||||||   |||  ||   |||  ||   |||  |   ||||||  |  ||||
1550  TTGAAACAGGATCCTCTAGAAATGACTCTGGCTTCCTCAGGGGCCCCAAC   1599
```

TABLE 4-continued

Comparison of the human and mouse IL-10 receptor subunits at the nucleotide and amino acid levels.

```
1609  TAGACAGTGGAATCAACTGACCGAAGAGTGGTCACTCCTGGGTGTGGTTA  1658
      ||||||||||  ||  |    ||  ||  ||  |||||||||||    ||
1600  GGGACAGTGGAACCAGCCCACTGAGGAATGGTCACTCCTGGCCTTGAGCA  1649

1659  GCTGTGAAGATCTAAGCATAGAAAGTTGGAGGTTTGCCCATAAACTTGAC  1708
      ||||    ||  ||    |  |||        |||||  |||||||||||  |  ||||  |
1650  GCTGCAGTGACCTGGGAATATCTGACTGGAGCTTTGCCCATGACCTTGCC  1699

1709  CCTCTGGACTGTGGGGCAGCCCTGGTGGCCTCCTGGATAGCCTTGGCTC  1758
      |||||  |  |||||  |||||||||  |||||  |||||||    |||  ||    |||
1700  CCTCTAGGCTGTGTGGCAGCCCCAGGTGGTCTCCTGGGCAGCTTTAACTC  1749

1759  TAACCTGGTCACCCTGCCGTTGATCTCCAGCCTGCAGGTAGAAGAA      1804
      ||||||||||||||||||  |  |||||  |||||||||||          ||
1750  AGACCTGGTCACCCTGCCCCTCATCTCTAGCCTGCAGTCAAGTGAG      1795
``` amino acid sequence comparison; mouse above, human below

```
  1  MLSRLLPFLVTI SSLSLEFI AYGTELPSPS YVWFEARFFQHI LHWKPIPN    50
     || . |::|..: ||.|:    |.|||||||. |||||  ||:|||||.||||
  1  MLPCLVVLLAALLSLRLGS DAHGTELPSPPS VWFEAEFFHHI LHWTPIPN    50

51  QSESTYYEVALKQYGNSTWNDI HI CRKAQALSCDLTTFTLDLYHRSYGYR   100
     |||||:|||||  .||  ..||.|  |   .|.|||:|||..|||||| | |||
 51  QSESTCYEVALLRYGI ESWNSI SNC..SQTLSYDLTAVTLDLYH.SNGYR    97

101  ARVRAVDNSQYSNWTTTETRFTVDEVI LTVDSVLTKAMDGI I YGTI HPPR   150
     |||||||.|...||:|||.|||||.|||.|||:||.|    :|:|.|.|:  ||
 98  ARVRAVDGSRHSNWTVTNTRFSVDEVTLTVGSVNLEI HNGFI LGKI QLPR   147

151  PTI TPAGDEYEQVFKDLRVYKI SI RKF.SELKNATKRVKQETFTLTVPI G   199
     |.:.||.|.|| :|..:| |.|.|||. :::: . |:||:|.|.|  ..:
148  PKMAPANDTYESI FSHFREYEI AI RKVPGNFTFTHKKVKHENFSLLTSGE   197

200  VRKFCVKVLPRLESRI NKAEWSEEQCLLI TTEQYFTVTNLSI LVI SMLLF   249
     |.|||.|  |.::|| ||:  ||.|:|: :  |||||||:  |:.  :||
198  VGEFCVQVKPSVASRSNKGMWSKEECI SL.TRQYFTVTNVI I FFAFVLLL   246

250  CGI LV.CLVLQWYI RHPGKLPTVLVFKKPHDF.FPANPLCPETPDAI HI V   297
     :| |. ||.||:|:|:. |||.||:|||| .| | ... :|||.|.|| :
247  SGALATCLALQLYVRRRKKLPSVLLFKKPSPFI FI SQRPSPETQDTI HPL   296

298  DLEVFPKVSLELRDSVLHGSTDSGFGSGKPSLQTEESQFLLPGSHPQI QG   347
     | |.| ||| ||::   |||||||||||.|||||||.|||||:.|||   :
297  DEEAFLKVSPELKNLDLHGSTDSGFGSTKPSLQTEEPQFLLPDPHPQADR   346

348  TLGKEESPGLQATC....GDNTDSGI CLQEPGLHSSMGPAWKQQLGYTHQ   393
     |||.:|.|.|...|      ::|||||||||:  .| ||.|.||:|:   .
347  TLGNGEPPVLGDSCSSGSSNSTDSGI CLQEPSLSPSTGPTWEQQVGSNSR   396

394  DQDDSDVNLVQNSPGQPKYTDASALGHVCLLEPKAPEEKDQVMVTFQGY    443
     :||||:::|||||.|.:  ||::|||||  : ||..|:|.|.. |.||||
397  GQDDSGI DVVQNSEGRAGDTQGGSALGHHSPPEPEVPGEEDPAAVAFQGY    446

444  QKQTRWKAEAAGPAECLDEEI PLTDAFDPELGVHLQDDLAWPPPALAAGY   493
     :|||   .|  |...:||:|| ||||::::|.:|   | |:  ::.|||| ||
447  LRQTRCAEEKATKTGCLEEESPLTDGLGPKFGRCLVDEAGLHPPALAKGY   496

494  LKQESQGMASAPPGTPSRQWNQLTEEWSLLGVVSCEDLSI ESWRFAHKLD   543
     |||:.  :|. |.|.|  |||| ||:|||||||||||  ||:|||..|.||||.
497  LKQDPLEMTLASSGAPTGQWNQPTEEWSLLALSSCSDLGI SDWSFAHDLA   546

544  PLDCGAAPGGLLDSLGSNLVTLPLI SSLQVEE                    575
     ||:|.||||||||:|:.|:||||||||||| .|
547  PLGCVAAPGGLLGSFNSDLVTLPLI SSLQSSE                    578
```

The present invention also encompasses proteins or peptides having substantial amino acid sequence homology with the amino acid sequences in Tables 2 or 3, but excluding any protein or peptide which exhibits substantially the same or lesser amino acid sequence homology than do known G-CSF, GM-CSF, EPO, TNF, IFN-γ, IL-2, IL-3, IL-4, IL-5, IL-6, or IL-7 receptor component sequences.

A polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Typically, fragments of homologous receptor components will exhibit substantial identity.

Amino acid sequence homology, or sequence identity, is determined by optimizing residue matches, if necessary, by introducing gaps as required. This changes when considering conservative substitutions as matches. Conservative substitutions typically include substitutions within the following groups: [glycine, alanine]; [valine, isoleucine, leucine]; [aspartic acid, glutamic acid]; [asparagine, glutamine]; [serine, threonine]; [lysine, arginine]; and [phenylalanine, tyrosine]. Homologous amino acid sequences are intended to include natural allelic and interspecies variations in each respective receptor sequence. Typical homologous proteins or peptides will have from 25–100% homology (if gaps can be introduced), to 50–100% homology (if conservative substitutions are included) with the amino acid sequence of Tables 2 or 3. Homology measures will be at least about 50%, generally at least 56%, more generally at least 62%, often at least 67%, more often at least 72%, typically at least 77%, more typically at least 82%, usually at least 86%, more usually at least 90%, preferably at least 93%, and more preferably at least 96%, and in particularly preferred embodiments, at least 98% or more. Some homologous proteins or peptides, such as the various receptor subtypes, will share various biological activities with the components of a receptor for IL-10, e.g., the embodiments provided in Tables 2 or 3. As used herein, the term "biological activity" is defined as including, without limitation, ligand (e.g., IL-10-like protein) binding, cross-reactivity with antibodies raised against each respective receptor component, and ligand dependent signal transduction. A "ligand-related activity" refers either to ligand binding itself, or to biological activities which are mediated by ligand binding, including, e.g., second messenger modulation, Ca$^{++}$ sequestration, phosphorylation, protein associations, etc.

The term "ligand" refers to molecules, usually members of the family of cytokine-like peptides, that bind to the receptor via the segments involved in peptide ligand binding. Also, a ligand is a molecule which serves either as a natural ligand to which the receptor, or an analog thereof, binds, or a molecule which is a functional analog of a natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds) (1990) *Goodman & Gilman's: The Pharmacological Bases of Therapeutics* (8th ed), Pergamon Press.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates its natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS.

One crude measure of solubility is based upon sedimentation rates, e.g., Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco; each of which is hereby incorporated herein by reference. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

Particularly useful soluble fragments of the receptor component will be ligand binding fragments. As the protein appears to contain extracellular domains with which the ligand should bind, a protein comprising the extracellular segments amino proximal to the transmembrane helix segment running from residues 217–243 would exhibit such binding activity. Fusions of the extracellular domain with other proteins, and shorter segments can be easily tested for ligand binding activity. Alternatively, fragments consisting of the intracellular domain should also be of interest.

Figure 18:
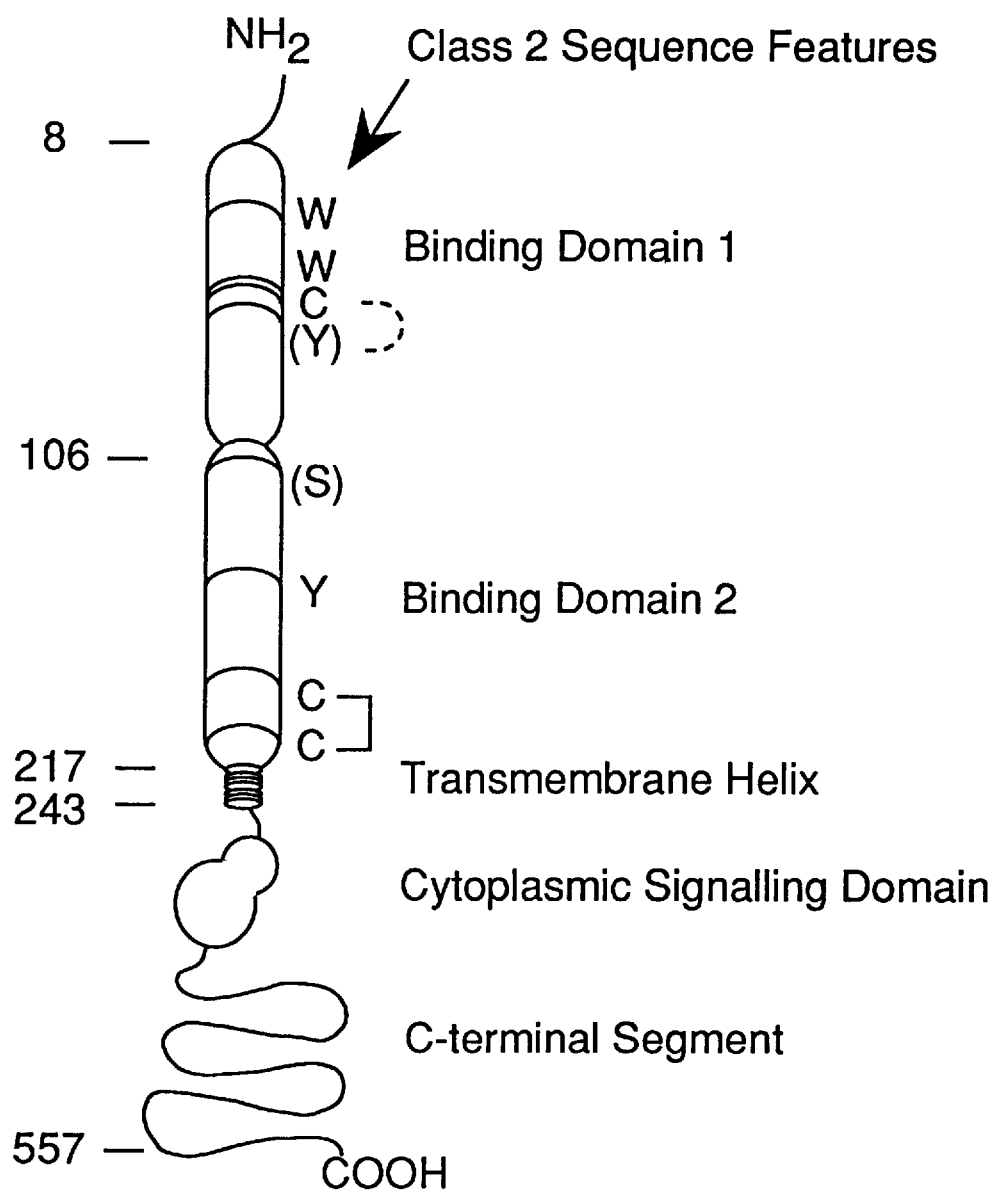
FIG. 18 shows a cartoon of the structure of the IL-10 receptor, its domain structure, and structural features which suggest a class 2 cytokine receptor classification.
Figure 19:
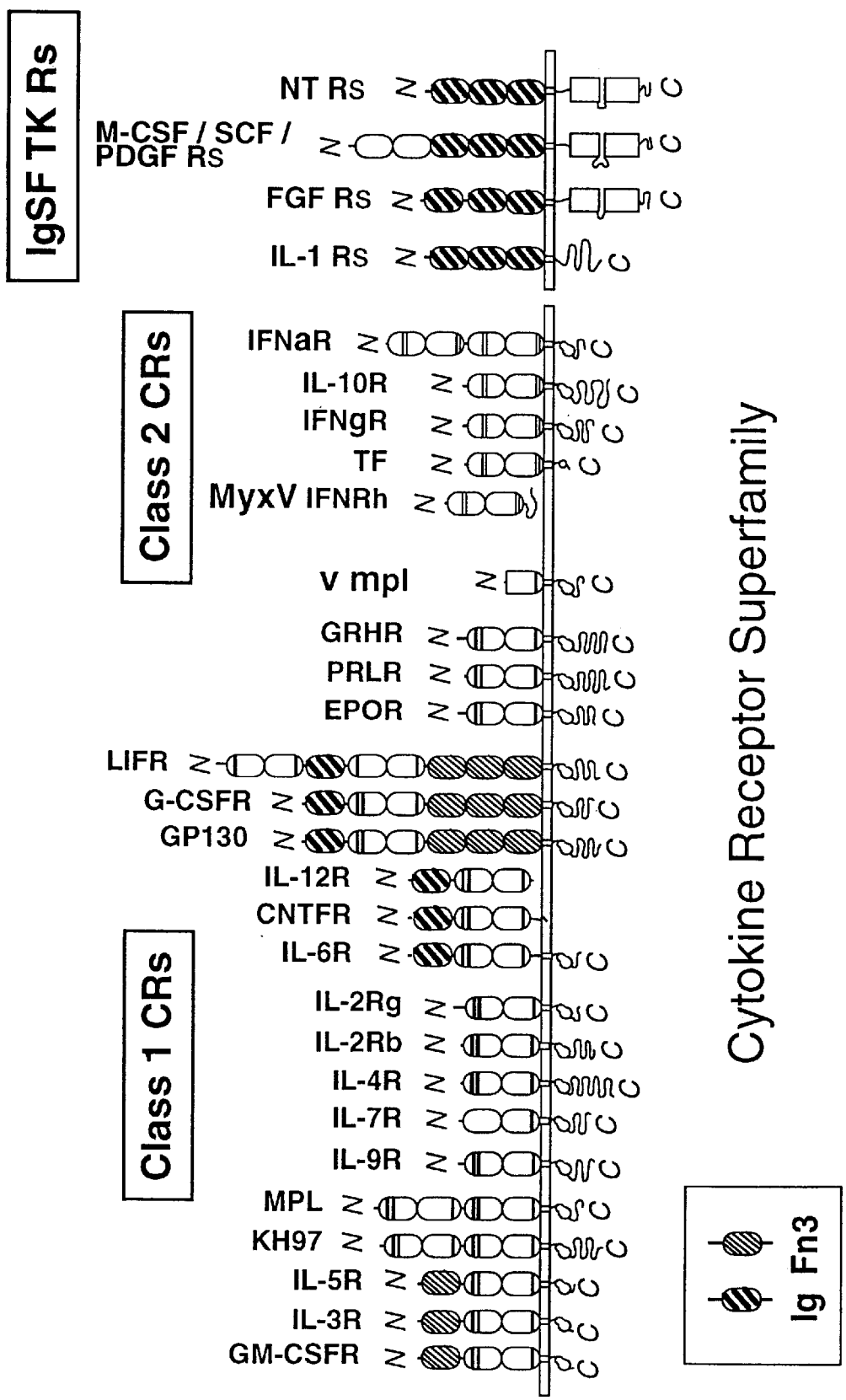
FIG. 19 shows a cartoon of members of the cytokine receptor superfamily.

In analysis of the polypeptide sequences of the human and mouse IL-10 receptors, the sequences exhibit 70–75% homology at the DNA and protein sequence levels. See, e.g., Table 4. On the basis of distinctive structural motifs, it is recognized that the IL-10 receptor polypeptides encoded herein are members of the class 2 group of the cytokine receptor superfamily. See, e.g., Bazan (1990) *Immunology Today* 11:350–354; and Bazan (1990) *Proc. Nat'l Acad. Sci. USA* 87:6934–6938; and FIGS. 18 and 19.

The characteristic motifs of the class 1 receptors include an amino-terminal set of four conserved cystines and one tryptophan residue, and a carboxy-terminal (membrane-proximal) collection of spaced aromatic residues. The motifs characteristic of the class 2 receptors are a conserved tryptophan and the second cysteine pair in the amino-terminal half, a WSxWS box analog in the carboxy-terminal half, and a second conserved cysteine pair.

The other members of the Class 2 are the receptors for interferon-α (IFN-α), for interferon-γ (IFN-γ), and for tissue factor, and for a second soluble viral IFN receptor homolog. The IL-10 receptor components described herein are particularly closely related to the interferon-γ receptor. These domain structure similarities suggest that the mechanisms of action of the IL-10 on its receptor may be related to similar mechanisms in the interaction of IFN-γ with its receptor. See, e.g., Levy, et al. (1990) *New Biologist* 2:923–928; Sen, et al. (1992) *J. Biol. Chem.* 267:5017–5020; and Uze, et al. (1992) *Proc. Nat'l Acad. Sci. USA* 89:4774–4778.

For example, the antagonistic effect of IL-10 on macrophage activation by IFN-γ may directly intervene in the signal cascade of IFN response. This may be effected by interaction of a component in the IFN signal pathway with a component in the IL-10 pathway. Sharing of components in the two pathways is a real possibility, including direct structural overlap of one or more components in active receptor complexes, e.g., shared β-like subunits. Alternatively, the structural similarities of the IFN and IL-10 receptor components will predict that regions of receptor structure critical in one pathway and conserved in the other will have like importance. This predictability extends to both ligand molecular surface shapes and to intracellular features likely to interact with downstream signal pathway components. This suggests methods of modulating a biological effect of IL-10, comprising a step of interfering with signal transduction of an interferon receptor, including, e.g., agonists or antagonists of an IFN, or homologous IL-10 receptor variants to IFN receptor mutants.

II. Nucleic Acids

This invention contemplates use of isolated nucleic acids, e.g., DNA, or fragments which encode these receptor components for IL-10 -like peptides, e.g., each respective species variant of these receptors, or any fragment thereof, to encode a biologically active counterpart receptor polypeptide. In addition, this invention covers isolated or recombinant DNA which encodes a biologically active protein or polypeptide having receptor activity and which is capable of hybridizing under appropriate conditions with the DNA sequences shown in Tables 2 or 3. Said biologically active protein or polypeptide can be a receptor itself, or fragment, and comprise an amino acid sequence shown in Tables 2 or 3. Further, this invention covers the use of isolated or recombinant DNA, or fragments thereof, which encode proteins which are homologous to each respective species variant or receptor or which was isolated using cDNA encoding a receptor for IL-10 as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode similar polypeptides to fragments of these receptors, and fusions of sequences from various different receptors or proteins.

A "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

A DNA which codes for a receptor for IL-10 will be particularly useful to identify genes, mRNA, and cDNA species which code for related or homologous receptors, as well as nucleic acids which code for species variants of these receptor components.

Preferred probes for screens are those regions of the receptors which are conserved between different species variants. Conserved regions will be identified by comparisons of completed sequences to one another.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Genomic sequences containing introns are also made available, along with methodologies to isolate them.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below, but are further limited by the homology to other known receptors for cytokines, e.g., the above described receptor components. Homology measures will be limited, in addition to any stated parameters, to exceed any such similarity to these receptors, e.g., GM-CSF, IL-3, IL-4, and IL-5 receptor components.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence derived from Tables 2 or 3. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213, which is incorporated herein by reference. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370, which is hereby incorporated herein by reference.

Isolation and characterization of these nucleic acids allow use thereof to make variants and mutants. It will also allow production of vector constructs useful, e.g., for making transgenic cells, including homologous recombination, e.g., gene "knock-out" animals, and for gene therapy. See, e.g., Goodnow, (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987) (ed.) *Teratocarcinomas and Embryonic Stem Cells: A Practical Approach* IRL Press, Oxford; and Rosenberg (1992) *J. Clinical Oncolocy* 10:180–199; which are each incorporated herein by reference.

III. Receptor Variants

The isolated receptor DNAs can be readily modified by nucleotide substitutions, nucleotide deletions, nucleotide insertions, and inversions of nucleotide stretches. These modifications result in novel DNA sequences which encode these receptors, their derivatives, or proteins having IL-10 receptor activity. These modified sequences can be used to produce mutant receptors or to enhance the expression of receptor species. Enhanced expression may involve gene amplification, increased transcription, increased translation, and other mechanisms. Such mutant receptor derivatives include predetermined or site-specific mutations of the respective receptor or its fragments. A "mutant IL-10 receptor" encompasses a polypeptide otherwise falling within the homology definition of the IL-10 receptor as set forth above, but having an amino acid sequence which differs from that IL-10 receptor most commonly as found in nature, whether by way of an amino acid deletion, substitution, or insertion. In particular, "site specific mutant IL-10 receptor" is a protein having homology with a receptor of Tables 2 or 3, and as sharing various biological activities with those receptor components. Similar proteins and nucleic acids should be available from other warm blooded animals, e.g., mammals and birds. As stated before, it is emphasized that descriptions are generally meant to encompass species and allelic variants of these receptor components, not limited to the IL-10 receptor examples specifically discussed.

Although site specific mutation sites are predetermined, mutants need not be site specific. IL-10 receptor mutagenesis can be conducted by making amino acid insertions or deletions. Substitutions, deletions, insertions, or any combinations may be generated to arrive at a final construct. Insertions include but are not limited to amino- or carboxy-terminal fusions. Random mutagenesis can be conducted at a target codon and the expressed IL-10 receptor mutants can then be screened for the desired activity. Methods for making substitution mutations at predetermined sites in DNA having a known sequence are well known in the art, e.g., by M13 primer mutagenesis. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these receptor components. A heterologous fusion protein is a fusion of proteins or segments which are naturally not normally fused in the same manner. Thus, the fusion product of an immunoglobulin with a receptor polypeptide is a continuous protein molecule having sequences fused in a typical peptide linkage, e.g., typically made as a single translation product and exhibiting properties derived from each source peptide. A similar concept applies to heterologous nucleic acid sequences.

In addition, new constructs may be made from combining similar functional domains from other proteins. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992, each of which is incorporated herein by reference. Thus, new chimeric polypeptides exhibiting new combinations of specificities will result from the functional linkage of ligand-binding specificities and intracellular regions. For example, the ligand binding domains from other related receptors may be added or substituted for other binding domains of these receptors. The resulting protein will often have hybrid function and properties.

The phosphoramidite method described by Beaucage and Caruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

The present invention provides means to produce fusion proteins. Various receptor variants may have slightly different functions or biological activities, even though they share significant structural similarities. Dissection of structural elements which effect the various physiological functions or biological activities provided by the receptors is possible using standard techniques of modern molecular biology, particularly in comparing variants within the related family of cytokine receptors. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390; each of which is incorporated herein by reference.

In particular, ligand binding segments can be substituted between receptors to determine what structural features are important in both ligand binding affinity and specificity. The segments of receptor accessible to an extracellular ligand would be primary targets of such analysis. An array of different receptor variants, e.g., allelic, will be used to screen for ligands exhibiting combined properties of interaction with them. Intracellular functions would probably involve segments of the receptor which are normally accessible to the cytosol. However, receptor internalization may occur under certain circumstances, and interaction between intracellular components and the designated "extracellular" segments may occur. These intracellular functions usually involve signal transduction from ligand binding. The specific segments of interaction of receptor with other proteins may be identified by mutagenesis or direct biochemical means, e.g., cross-linking or affinity methods. Structural analysis by crystallographic or other physical methods will also be applicable. Identification of the similarities and differences between receptor variants exhibiting distinct functions will lead to new diagnostic and therapeutic reagents or treatments.

Further study of the expression and control of receptor variants will be useful. The controlling elements associated with the receptors could exhibit differential developmental, tissue specific, or other expression patterns. Upstream or downstream genetic regions, e.g., control elements, are of interest.

Structural studies of the receptor variants will lead to design of new ligands, particularly analogues exhibiting agonist or antagonist properties. This can be combined with previously described screening methods to isolate ligands exhibiting desired spectra of activities.

Expression in other cell types will often result in glycosylation differences in a particular receptor. Various receptor variants may exhibit distinct biological activities based upon structural differences other than amino acid sequence. Differential modifications may be responsible for differential function, and elucidation of the effects are now made possible.

Thus, the present invention provides various receptors, e.g., species variants and fusion proteins, for IL-10, and reagents developed from them. Although the foregoing description has focused primarily upon the human and mouse IL-10 receptors, those of skill in the art will immediately recognize that the invention encompasses receptors from various different mammalian species.

IV. Making Receptor

A nucleic acid which encodes the IL-10 receptor or fragments thereof is available in the pMR29 and pSW8.1 clones, or can be obtained by chemical synthesis, screening cDNA libraries, or by screening genomic libraries prepared from a wide variety of cell lines or tissue samples.

This DNA can be expressed in a wide variety of host cells for the synthesis of a full-length receptor or fragments of a receptor which can in turn, for example, be used to generate polyclonal or monoclonal antibodies; for binding studies; for construction and expression of modified receptor molecules; and for structure/function studies. Each receptor or its fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The receptor, or portions thereof, may be expressed as fusions with other proteins.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes a receptor for an IL-10-like peptide, or a fragment thereof encoding a biologically active receptor polypeptide. The DNA can be under the control of a viral promoter and can encode a selection marker. This invention further contemplates use of such expression vectors which are capable of expressing eukaryotic cDNA coding for a receptor in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the IL-10 receptor or its fragments in various hosts using vectors that do not contain a replication origin that is recognized by the host cell. It is also possible to use vectors that cause integration of IL-10 receptor or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (eds) *Vectors: A Survey of Molecular Cloning Vectors and Their Uses*, Buttersworth, Boston, 1988, which are incorporated herein by reference.

Transformed cells are cells, preferably mammalian, that have been transformed or transfected with receptor vectors constructed using recombinant DNA techniques. Transformed host cells usually express the receptor or its fragments, but for purposes of cloning, amplifying, and manipulating its DNA, do not need to express the receptor. This invention further contemplates culturing transformed cells in a nutrient medium, thus permitting the receptor or fragments, e.g., a soluble protein, to accumulate in the culture. The receptor proteins can be recovered from the cells or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in *Vectors: A Survey of Molecular Cloning Vectors and Their Uses*, (eds. Rodriguez and Denhardt), Buttersworth, Boston, Chapter 10, pp. 205–236, which is incorporated herein by reference.

Lower eukaryotes, e.g., yeasts and Dictyostelium, may be transformed with IL-10 receptor sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic cells grown in tissue culture are often the preferred host cells for expression of the functionally active IL-10 receptor protein. In principle, any higher eukaryotic tissue culture cell line is workable, e.g., insect baculovirus expression systems, whether from an invertebrate or vertebrate source. However, mammalian cells are often preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1 (Invitrogen, San Diego, Calif.); pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610, see e.g., O'Reilly, et al. (1992) *Baculovirus Expression Vectors: A Laboratory Manual* Freeman & Co., N.Y.

It will often be desired to express a receptor polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the receptor gene may be co-transformed with one or more genes encoding mammalian or other glycosylating enzymes. Using this approach, certain mammalian glycosylation patterns will be achievable in prokaryote or other cells.

V. Receptor Isolation

The described nucleic acids will provide useful source materials possessing high levels of receptor proteins. Cells expressing these proteins can be sources for protein purification, of the natural receptor forms, or variants thereof. In addition, purification segments can be fused to appropriate portions of the receptor to assist in isolation and production. For example, the FLAG sequence, or a functional equivalent, can be fused to the protein via a protease-removable sequence, allowing the FLAG sequence to be recognized by an affinity reagent, and the purified protein subjected to protease digestion to remove the extension. Many other equivalent segments exist, e.g., poly-histidine segments possessing affinity for heavy metal column reagents. See, e.g., Hochuli (1989) *Chemische Industrie*

12:69–70; Hochuli (1990) "Purification of Recombinant Proteins with Metal Chelate Adsorbent" in Setlow (ed) *Genetic Engineering, Principle and Methods* 12:87–98, Plenum Press, N.Y.; and Crowe, et al. (1992) *OIAexpress: The High Level Expression & Protein Purification System* QUIAGEN, Inc. Chatsworth, Calif.; which are incorporated herein by reference.

Moreover, appropriate host cells may be used to express the receptor proteins at high levels and under physiological conditions which may allow for desirable post-translational processing, e.g., glycosylation variants.

Having produced high level expression sources, standard protein purification techniques are applied to purify the IL-10 receptor components to near homogeneity. These will include such methods as ammonium sulfate precipitation, column chromatography, electrophoresis, centrifugation, crystallization, and others. See, e.g., Ausubel, et al. (1987 and periodic supplements) *Current Protocols in Molecular Biology*; Deutscher (1990) "Guide to Protein Purification" in *Methods in Enzymology* vol 182, and other volumes in this series; and manufacturers' literature on use of protein purification products, e.g., Pharmacia, Piscataway, N.J., or Bio-Rad, Richmond, Calif.; which are incorporated herein by reference.

VI. Receptor Analogues

"Derivatives" of the IL-10 receptor include amino acid sequence mutants, glycosylation variants, and covalent or aggregative conjugates with other chemical moieties. Covalent derivatives can be prepared by linkage of functionalities to groups which are found in the IL-10 receptor amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the IL-10 receptor or fragments thereof with other proteins or polypeptides. These derivatives can be synthesized in recombinant culture such as N- or C-terminal fusions or by the use of agents known in the art for their utility in cross-linking proteins through reactive side groups. Preferred IL-10 derivatization sites with cross-linking agents are at free amino groups, carbohydrate moieties, and cysteine residues.

Fusion polypeptides between the receptors and other homologous or heterologous proteins are also provided. Homologous polypeptides may be fusions between different growth factor or cytokine receptors, resulting in, for instance, a hybrid protein exhibiting ligand specificity of one receptor and the intracellular region of another, or a receptor which may have broadened or weakened specificity of binding. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Caruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory, which are incorporated herein by reference. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; each of which is incorporated herein by reference.

This invention also contemplates the use of derivatives of the IL-10 receptor other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of IL-10 or other binding ligands. For example, the IL-10 receptor can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-IL-10 receptor antibodies or IL-10. The IL-10 receptor can also be labeled with a detectable group, for example radioiodinated by the chloramine T procedure, covalently bound to rare earth chelates, or conjugated to another fluorescent moiety for use in diagnostic assays.

The solubilized IL-10 receptor of this invention can be used as an immunogen for the production of antisera or antibodies specific for the receptor or any fragments thereof. The purified receptor can be used to screen monoclonal antibodies or antigen-binding fragments prepared by immunization with various forms of impure preparations containing the IL-10 receptor. In particular, the term "antibodies" also encompasses antigen binding fragments of natural antibodies. The purified receptor can also be used as a reagent to detect any antibodies generated in response to the presence of elevated levels of IL-10 receptor or cell fragments containing the IL-10 receptor. Additionally, IL-10 receptor fragments may also serve as immunogens to produce the antibodies of the present invention, as described immediately below. For example, this invention contemplates antibodies having binding affinity to or being raised against the amino acid sequence shown in Tables 2, or 3, or fragments thereof. In particular, this invention contemplates antibodies having binding affinity to or being raised against specific fragments which are predicted to lie outside of the lipid bilayer. These fragments should become readily apparent upon completion of the sequence of the human or mouse receptors. In addition, this invention covers fragments of the IL-10 receptor which are predicted to reside on the extracellular side of the membrane. Analysis of protein structure to identify membrane associated regions is described, e.g., in von Heijne (1992) *J. Mol. Biol.* 225:487–494; and Fasman, et al. (1990) *Trends in Biochemical Sciences* 15:89–92.

VII. Antibodies

Antibodies can be raised to the various species variants of these receptor components, and fragments thereof, both in their naturally occurring forms and in their recombinant forms. Additionally, antibodies can be raised to IL-10 receptors in either their active forms or in their inactive forms, the difference being that antibodies to the active receptor are more likely to recognize epitopes which are only present in the active receptor. Anti-idiotypic antibodies are also contemplated.

Antibodies, including binding fragments and single chain versions, against predetermined fragments of the IL-10 receptor can be raised by immunization of animals with conjugates of the fragments with immunogenic proteins. Monoclonal antibodies are prepared from cells secreting the desired antibody. These antibodies can be screened for binding to normal or defective IL-10 receptors, or screened for agonistic or antagonistic IL-10 receptor activity. These monoclonal antibodies will normally bind with at least a Kd of about 1 mM, more normally at least 300 $\mu$M, generally at least 100 $\mu$M, more generally at least 30 $\mu$M, ordinarily at least 10 $\mu$M, more ordinarily at least 3 $\mu$M, often at least 1 $\mu$M, more often at least 300 nM, typically at least 100 nM, more typically at least 30 nM, usually at least 10 nM, more usually at least 3 nM, preferably at least 1 nM, more preferably at least 300 pM, and in especially preferred embodiments at least 100 to 10 pM or better. Antibodies will be raised against species or other variants of these receptor components.

The antibodies, including antigen binding fragments, of this invention can have significant diagnostic or therapeutic value. They can be potent antagonists that bind to the IL-10 receptor and inhibit ligand binding to the receptor or inhibit the ability of an IL-10-like peptide to elicit a biological response. They also can be useful as non-neutralizing antibodies and can be coupled to toxins or radionuclides so that when the antibody binds to the receptor, the cell itself is killed. Further, these antibodies can be conjugated to drugs or other therapeutic agents, either directly or indirectly by means of a linker.

The antibodies of this invention can also be useful in diagnostic applications. As capture or non-neutralizing antibodies, they can bind to the IL-10 receptor without inhibiting ligand binding. As neutralizing antibodies, they can be useful in competitive binding assays. They will also be useful in detecting or quantifying IL-10 or IL-10 receptors.

Receptor fragments may be joined to other materials, particularly polypeptides, as fused or covalently joined polypeptides to be used as immunogens. The IL-10 receptor and its fragments may be fused or covalently linked to a variety of immunogens, such as keyhole limpet hemocyanin, bovine serum albumin, tetanus toxoid, etc. For descriptions of methods of preparing polyclonal antisera, see *Microbiology*, Hoeber Medical Division, Harper and Row, 1969; Landsteiner (1962) *Specificity of Serological Reactions*, Dover Publications, New York, and Williams, et al. (1967) *Methods in Immunology and Immunochemistry*, Vol. 1, Academic Press, New York, each of which is incorporated herein by reference. A typical method involves hyperimmunization of an animal with an antigen. Blood from the animal is then collected shortly after repeated immunizations and gamma globulin is isolated.

In some instances, it is desirable to prepare monoclonal antibodies from various mammalian hosts, such as mice, rodents, cows, sheep, goats, donkeys, primates, humans, etc. Description of techniques for preparing such monoclonal antibodies may be found in, e.g., Stites, et al. (eds) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed) Academic Press, New York; and particularly in Kohler and Milstein (1975) in *Nature* 256: 495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277, 437; 4,275,149; and 4,366,241. Also, recombinant immunoglobulins may be produced, see Cabilly, U.S. Pat. No. 4,816,567. These patents are incorporated herein by reference.

The antibodies of this invention can also be used for affinity chromatography in isolating the receptor. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified receptor protein will be released.

The antibodies may also be used to screen expression libraries for particular expression products. Usually the antibodies used in such a procedure will be labeled with a moiety allowing easy detection of presence of antigen by antibody binding.

Antibodies raised against each receptor will also be used to raise anti-idiotypic antibodies. These will be useful in detecting or diagnosing various immunological conditions related to expression of the respective receptors.

VIII. Other Uses of Receptors

Soluble receptor fragments will also find use as carriers for IL-10, e.g., to protect the cytokine from various degradative or other activities. The complex may be useful in certain situations as a slow release composition, allowing slow functional release of the cytokine or antagonist. Moreover, as an antagonist of IL-10, soluble forms of the receptor, e.g., a fragment containing the cytokine binding portions without membrane associated segments, will be useful diagnostic or therapeutic compositions. As a diagnostic reagent, such fragment may be used as a substitute for antibodies against IL-10, but will likely be equivalent to a neutralizing antibody.

In addition, it is likely that the isolated component described herein is analogous to a subunits of other cytokine receptors. This suggests that a unique β component for the IL-10 receptor may exist, and could, in association with these components, modulate the activity from IL-10 binding. This will provide a convenient means to isolate this putative β subunit. See, e.g., Hayashida, et al. (1990) *Proc. Nat'l Acad. Sci. USA* 87:9655–9659. Alternatively, species or tissue specific accessory molecules, e.g., proteins, may provide a context for modification of the receptor protein properties or activities.

Both the naturally occurring and the recombinant form of the IL-10 receptor components of this invention are particularly useful in kits and assay methods which are capable of screening compounds for binding activity to the receptors. Several methods of automating assays have been developed in recent years so as to permit screening of tens of thousands of compounds per year. See, e.g., Fodor, et al. (1991) *Science* 251:767–773, which is incorporated herein by reference and which describes means for testing of binding affinity by a plurality of defined polymers synthesized on a solid substrate. Phage or other libraries of various random polypeptide sequences would also be useful. The development of suitable assays can be greatly facilitated by the availability of large amounts of purified, soluble receptor such as is provided by this invention.

For example, antagonists can normally be found once the receptor has been characterized. Testing of potential receptor antagonists is now possible upon the development of highly automated assay methods using a purified receptor. In particular, new agonists and antagonists will be discovered using screening techniques made available by the reagents provided herein.

This invention is particularly useful for screening compounds by using the recombinant receptors in any of a variety of drug screening techniques. The advantages of using a recombinant receptor in screening for receptor reactive drugs include: (a) improved renewable source of the receptor from a specific source; (b) potentially greater number of receptors per cell giving better signal-to-noise ratio in assays; and (c) species variant specificity (theoretically giving greater biological and disease specificity).

One method of drug screening utilizes eukaryotic or prokaryotic host cells which are stably transformed with recombinant DNA molecules expressing the receptor. Cells may be isolated which express a receptor in isolation from any others. Such cells, either in viable or fixed form, can be used for standard receptor/ligand binding assays. See also, Parce, et al. (1989) *Science* 246:243–247; and Owicki, et al. (1990) *Proc. Nat'l Acad. Sci. USA* 87:4007–4011, which are incorporated herein by reference and describe sensitive methods to detect cellular responses. Competitive assays are particularly useful, where the cells (a source of IL-10 receptor) are contacted and incubated with a labeled ligand having known binding affinity to the receptor, such as $^{125}$I-IL-10, and a test compound whose binding affinity to the IL-10 receptor is being measured. The bound ligand and free ligand are then separated to assess the degree of ligand binding. The amount of test compound bound is inversely proportional to the amount of labeled ligand binding measured. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on IL-10 receptor mediated functions, e.g., second messenger levels, i.e., $Ca^{++}$; cell proliferation; inositol phosphate pool changes; levels of phosphorylation; nitrous oxide levels; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus. See also, Lowenstein, et al. (1992) *Cell* 70:705–707.

Another method utilizes membranes from transformed eukaryotic or prokaryotic host cells as the source of the IL-10 receptor. These cells are stably transformed with DNA vectors directing the expression of the IL-10 receptor. Essentially, the membranes would be prepared from the cells and used in an appropriate receptor/ligand binding assay, e.g., the competitive assay set forth above.

Still another approach is to use solubilized, unpurified or solubilized, purified receptors from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to the IL-10 receptor and is described in detail in Geysen, European Patent Application 84/03564, published on Sep. 13, 1984, which is incorporated herein by reference. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified IL-10 receptor, and washed. The next step involves detecting bound IL-10 receptor.

Rational drug design may also be based upon structural studies of the molecular shapes of the receptor and other effectors or ligands. Effectors may be other proteins which mediate other functions in response to ligand binding, or other proteins which normally interact with the receptor. One means for determining which sites interact with specific other proteins is a physical structure determination, e.g., x-ray crystallography or NMR techniques (2 or 3 dimensional). These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

Purified receptor can be coated directly onto plates for use in the aforementioned drug screening techniques. However, non-neutralizing antibodies to these receptors can be used as capture antibodies to immobilize the respective receptor on the solid phase.

IX. Ligands: Agonists and Antagonists

The blocking of physiological response to IL-10-like peptides may result from the inhibition of binding of the ligand to the receptor, likely through competitive inhibition. Thus, in vitro assays of the present invention will often use isolated membranes from cells expressing a recombinant receptor, soluble fragments comprising the ligand binding segments of these receptors, or fragments attached to solid phase substrates. These assays will also allow for the diagnostic determination of the effects of either binding segment mutations and modifications, or ligand mutations and modifications, e.g., ligand analogues.

This invention also contemplates the use of competitive drug screening assays, e.g., where neutralizing antibodies to the receptor or receptor fragments compete with a test compound for binding to the receptor. In this manner, the antibodies can be used to detect the presence of any polypeptide which shares one or more binding sites of the receptor and can also be used to occupy binding sites on the receptor that might otherwise be occupied by IL-10.

Additionally, neutralizing antibodies against the receptor and soluble fragments of the receptor which contain the ligand binding site can be used to inhibit IL-10 receptor function in, e.g., macrophages, B cells, T cells, or related cell types.

X. Kits

This invention also contemplates use of the IL-10 receptor, fragments thereof, peptides, and their fusion products in a variety of diagnostic kits and methods for detecting the presence of the IL-10 receptor. Typically the kit will have a compartment containing either a defined receptor peptide or gene segment or a reagent which recognizes one or the other.

A kit for determining the binding affinity of a test compound to IL-10 receptor would typically comprise a test compound; a labeled compound, for example a ligand or antibody having known binding affinity for IL-10 receptor; a source of IL-10 receptor (naturally occurring or recombinant); and a means for separating bound from free labeled compound, such as a solid phase for immobilizing IL-10 receptor. Once compounds are screened, those having suitable binding affinity to the IL-10 receptor can be evaluated in suitable biological assays, as are well known in the art, to determine whether they act as agonists or antagonists. The availability of recombinant receptor polypeptides also provide well defined standards for calibrating such assays.

A preferred kit for determining the concentration of, for example, IL-10 receptor in a sample would typically comprise a labeled compound, e.g., ligand or antibody, having known binding affinity for the receptor, a source of IL-10 receptor (naturally occurring or recombinant) and a means for separating the bound from free labeled compound, for example a solid phase for immobilizing the IL-10 receptor. Compartments containing reagents, and instructions, will normally be provided.

One method for determining the concentration of IL-10 receptor in a sample would typically comprise the steps of: (1) preparing membranes from a sample comprised of a IL-10 receptor source; (2) washing the membranes and suspending them in a buffer; (3) solubilizing the IL-10 receptor by incubating the membranes in a culture medium to which appropriate detergents have been added; (4) adjusting the detergent concentration of the solubilized receptor; (5) contacting and incubating said dilution with radiolabeled IL-10 to form IL-10:IL-10 receptor complexes; (6) recovering the complexes such as by filtration through polyethyleneimine treated filters; and (7) measuring the radioactivity of the recovered complexes.

Antibodies, including antigen binding fragments, specific for the receptor or receptor fragments are useful in diagnostic applications to detect the presence of elevated levels of the receptor and/or its fragments. Such diagnostic assays can employ lysates, live cells, fixed cells, immunofluorescence, cell cultures, body fluids, and further can involve the detection of antigens related to the IL-10 receptor in serum, or the like. Diagnostic assays may be homogeneous (without a separation step between free reagent and receptor-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to the IL-10 receptor or to a particular fragment thereof. These assays have also been extensively discussed in the literature. See, e.g., Harlow and Lane (1988) *Antibodies: A Laboratory Manual*, CSH.

Anti-idiotypic antibodies may have similar use to diagnose presence of antibodies against a receptor, as such may be diagnostic of various abnormal states. For example, over- or inappropriate production of IL-10 receptor may result in various immunological reactions which may be diagnostic of abnormal receptor expression, particularly in proliferative cell conditions such as cancer.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium having appropriate concentrations for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the ligand, test compound, IL-10 receptor, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The receptor can be immobilized on various matrices followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of receptor/ligand complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30(9):1457–1461, and the double antibody magnetic particle separation as described in U.S. Pat. No. 4,659,678, each of which is incorporated herein by reference.

The methods for linking protein receptors or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a receptor for IL-10. These sequences can be used as probes for detecting abnormal levels of the receptor in defined cells of patients suspected of having, e.g., an autoimmune condition, inability to properly respond to infections or inflammation, or a proliferative cell condition like cancer. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using photoreactive or biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein complexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

XI. Therapeutic Applications

This invention provides reagents with significant therapeutic value. The IL-10 receptor (naturally occurring or recombinant), fragments thereof and antibodies thereto, along with compounds identified as having binding affinity to the IL-10 receptor, should be useful in the treatment of various conditions, e.g., autoimmune conditions, septic and toxic shock conditions, and infectious conditions. See, e.g., Hsu et al (1992) *Intn'l Immunol.* 4:563–569; de Waal Malefyt, et al. (1991) *J. Expt'l Med.* 174:1209–1220; Fiorentino, et al. (1991) *J. Immunol.* 147:3815–3822; and Ishida, et al. (1992) *J. Expt'l Med.* 175:1213–1220. Additionally, this invention should have therapeutic value in any disease or disorder associated with abnormal expression or abnormal triggering of receptors for IL-10. For example, it is believed that the IL-10 receptor likely plays a role in many basic regulatory processes in immune function. Agonists and antagonists of the cytokine will be developed using the present invention. See also, e.g., Harada, et al. (1992) *J. Biol. Chem.* 267:22752–22758, which identifies receptor segments which are useful in antagonizing receptor function.

Recombinant IL-10 receptor, including soluble fragments thereof, or IL-10 receptor antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, e.g., which are soluble, which are not complement-binding.

Drug screening using the IL-10 receptor or fragments thereof can be performed to identify compounds having binding affinity to the IL-10 receptor. Subsequent biological assays can then be utilized to determine if the compound has intrinsic stimulating activity and is therefore a blocker or antagonist in that it blocks the activity of IL-10. Likewise, a compound having intrinsic stimulating activity can activate the receptor and is thus an agonist in that it simulates the activity of IL-10. This invention further contemplates the therapeutic use of antibodies to the IL-10 receptor as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Because of the high affinity binding between IL-10 and its receptors, low dosages of these reagents would be initially expected to be effective. Thus, dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 100 fM (femtomolar), with an appropriate carrier. Slow release formulations, or slow release apparatus will often be utilized for continuous administration. The intracellular segments of the receptors, both the IL-10 receptor and related receptors will find additional uses as described in detail below.

The IL-10 receptor, fragments thereof, and antibodies to the receptor or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; each of which is hereby incorporated herein by reference. The therapy of this invention may be combined with or used in association with other chemotherapeutic or chemopreventive agents.

XII. Additional Receptor Subunits

It is quite likely that additional subunits of the IL-10 receptor exist. IL-10 exhibits different specific activities (units per mg of protein) in different biological assays. For example, the specfic activity of IL-10 in cytokine synthesis inhibitory factor assays, where IL-10 acts on macrophages, is higher than that observed in costimulation of mouse thymocyte or mouse mast cell proliferation. See Table 5.

TABLE 5

Activities of recombinant mouse or human IL-10, in units/ml.

| Sample | CSIF ASSAYS | | |
|---|---|---|---|
| | IFN-$\gamma$ | $^3$H cpm | thymocyte $^3$H cpm |
| mouse IL-10 | $10^6$ | $2 \times 10^6$ | $\sim 2 \times 10^5$ |
| E. coli (~0.2 mg/ml) | | | |
| Baculovirus (~5 $\mu$g/ml) | $5 \times 10^4$ | $6 \times 10^4$ | 6000 |

TABLE 5-continued

Activities of recombinant mouse or human IL-10, in units/ml.

| Sample | CSIF ASSAYS | | |
|---|---|---|---|
| | IFN-$\gamma$ | $^3$H cpm | thymocyte $^3$H cpm |
| COS7 (~0.6 $\mu$g/ml) human IL-10 | 9000 | 9000 | ~500 |
| COS7 (~0.15 $\mu$g/ml) | 1400 | 1100 | ~90 |
| CHO (~1 mg/ml) | $10^7$ | $10^7$ | $\sim 8 \times 10^5$ |

The human and mouse IL-10 receptors provided herein bind IL-10 on their own. However, the ability of each component by itself to bind vIL-10 has not yet been demonstrated. In addition, the apparent Kd of the recombinant IL-10 receptor (100–400 pM) is considerably higher than the $EC_{50}$ of IL-10 on macrophages and monocytes (5–20 pM). By analogy to related class 2 cytokine receptors, e.g., IFN-$\alpha$, IFN-$\beta$, or IFN-$\gamma$, whose structural motifs are similar, an accessory molecule might be required for signal transduction upon IL-10 binding.

If so, various approaches would be useful for screening for accessory components. These approaches include both physical affinity methods, and activity screening. Similar affinity methods as used herein with human IL-10 can be used with vIL-10. See, e.g., Table 1. Since binding of these components to vIL-10, which has activity, has not been demonstrated some modified form of the receptor would be expected to exist. A FLAG-vIL-10 fusion construct should be useful in selective purification of cells containing such a receptor form.

One approach is to transfect libraries made from appropriate cells, e.g., cells capable of responding to vIL-10, to screen transfected cells which otherwise are non-responsive to v-IL-10; or fail to bind to vIL-10 (or the FLAG-vIL-10 fusion). Such a library of transfected cells could be screened using a FLAG-vIL-10 marker at a concentration too low to bind effectively to the receptor component described in Tables 2 or 3. See, e.g., Kitamura, et al. (1991) *Cell* 66:1165–1174; and Hara, et al. (1992) 11:1875–1884. Alternatively, a FLAG-vIL-10 fusion construct can be used for panning or FACS separation, e.g., as described in Table 1 and Example 4. These techniques may be combined with cotransfection with the IL-10 component already isolated, e.g., to isolate accessory components which modify the binding properties. Components which increase ligand binding affinity upon association are particularly desired. cDNA clones isolated in this manner are characterized, e.g., by sequencing, and compared structurally to other subunits or accessory proteins identified in other receptors.

The broad scope of this invention is best understood with reference to the following examples, which are not intended to limit the inventions in any manner.

EXPERIMENTAL

The following experimental results show that high specific activity iodinated hIL-10 can be enzymatically prepared and that this labeled ligand can bind in a specific and saturable manner to its receptor in several mouse and human cell lines. MC/9 proliferation assays showed that this labeled protein retains greater than 50% biological activity. Molecular weight sizing of the purified, iodinated protein indicated that the protein exists predominantly as a dimer and in this form is capable of binding specifically to its receptor. A 37 kDa dimer of human IL-10, when examined under reducing conditions, may be dissociated by detergents to a single 18 kDa species. This is consistent with the 37 kDa species representing a non-covalently linked dimer of the cytokine. Moreover, this suggests that active hIL-10 is a non-covalently linked dimer.

Screening for specific binding with several cell lines of mouse and human origin indicates that murine mast cell line MC/9 and human B lymphoma line JY have the highest number of accessible, e.g., unoccupied, receptors per cell. Human B cell lines Ramos and BH5, as well as erythroleukemia line TF-1, bind at a reduced level relative to MC/9 and JY, followed by human T-cell and macrophage lines. These cell lines were chosen based on the reported observations that mast cells, macrophage/monocytes, B cells, and T cells respond to IL-10. The TF-1 cell line, originally derived from an erythroleukemic patient, is dependent on IL-3, erythropoietin, or GM-CSF for long term growth. The cell line is also responsive to IL-4, IL-5 and IL-6 in proliferation assays. Despite the responsiveness of the TF-1 cell line to a variety of cytokines, no proliferative effects on TF-1 cells in response to hIL-10 either alone or in combination with other cytokines could be detected.

The Kd values obtained from Scatchard analysis indicate that hIL-10 binds with relatively high affinity to its receptor on both mouse and human cells, and that the receptor is present at the numbers between 100 and 300 unoccupied receptors per cell. Competition binding assays with human and murine IL-10 on the mouse mast cell line MC/9 and the human cell line JY demonstrated that while the mouse ligand is able to compete with binding of iodinated hIL-10 to the mouse cell line, it cannot do so with the human cell line. One explanation is that under the binding conditions employed, hIL-10 can recognize and bind to both the mouse and the human receptor, while the mouse IL-10 can only recognize the mouse receptor. Supporting this notion of species-specificity of the mouse ligand in binding site-recognition is the absence of any significant biological cross-reactivity of murine IL-10 on human cells.

Chemical cross-linking of radiolabeled hIL-10 to JY and MC/9 cells yielded a similar pattern of complexes. The intensities of observable signals were very weak even after a long exposure. In MC/9, two major and a few minor bands were detected, representing hIL-10 specific binding complexes. The apparent Mr of the minor bands was estimated to be about 110–180 kDa and the two more visible bands were estimated to be about 98 kDa and 83 kDa, respectively. The 98 kDa and 83 kDa bands were also observed with JY cells although the signals were relatively weaker. The presence of these common bands indicated that the molecular sizes of the observed human and mouse IL-10 receptors are similar. The approximated size difference between the 117 kDa and the 98 kDa complex, i.e., 19 kDa, is consistent with the molecular weight of an hIL-10 monomer. One explanation of the these observations is that the 117 kDa band might represent receptor/hIL-10 dimer complex and the 98 kDa might represent a dissociation product. However, there are other explanations such as differential glycosylation of the receptor(s), multimeric receptor(s), or protein degradation of ligand-receptor complexes.

Upon reevaluation of the molecular weight standards, the major bands have been assigned molecular weights in the range of 90–110 kD.

Several cytokines and growth factors, for example, G-CSF and IL-5, possess both high and low affinity binding sites on cell lines. Under the conditions used to examine the binding of human IL-10 to cells, it has not been possible to detect more than one class of binding site with the JY and MC/9 cell lines. There is a possibility of low affinity binding sites on these cell lines which are not detectable under the binding and washing regimen employed, or the presence of low affinity binding sites on other cell lines not included in this study. There is also a possibility of higher affinity binding sites present in numbers too small to be detected.

EXAMPLE 1

General Methods

Cell Lines and tissue culture.

MC/9 cells (ATCC# CRL1649) were routinely grown in Dulbecco's modified essential medium (DMEM) with 10% fetal bovine serum containing 3–5% mitogen-stimulated spleen-conditioned media, 100 U/ml mIL-4, 10 U/ml Penicillin/Streptomycin, 2 mM glutamine, 1 mM sodium pyruvate, 1×MEM essential and non-essential amino acids, 1×MEM vitamins, 50 μM β-mercaptoethanol, 6 mg/liter folic acid, 116 mg/liter L-arginine, and 36 mg/liter L-asparagine. TF-1 cells (see Kitamura, et al. (1989) *J. Cell. Physiol.* 140:323–334) were grown in RPMI1640 with 10% FBS and 1 μg/liter mouse GM-CSF. JY cells (provided by J. de Vries, DNAX, Palo Alto, Calif.) were grown in DMEM with 10% FBS, 6 mM glutamine, and antibiotics. The other cell lines [Ramos (ATCC# CRL1596), WEHI 265.1 (TIB204), U937 (CRL1593), HL-60 (CCL240), JD (CRL8163), Jijoye (CCL87), THP-1 (TIB202), B-JAB (provided by J. Banchereau, Schering-Plough France), and BH-5 (provided by W. Tadmori, Schering-Plough Research Institute, SPRI)] were grown in RPMI with 10% FBS, 6 mM glutamine, and antibiotics. In addition, culture media for BH-5 and THP-1 cells were supplemented with 50 μM β-mercaptoethanol. All tissue culture reagents were from GIBCO (Gaithersburg, Md.).

Fluorescence activated cell sorting (FACS)

Fluorescent activated cell sorting was performed using standard methods on a Becton-Dickinson FACStar PLUS. See, e.g., Shapiro (1988) *Practical Flow Cytometry* (2d ed.) Alan Liss, New York, which is incorporated herein by reference.

Cytokines and antibodies.

Recombinant CHO-derived human IL-10 and IL-5, as well as *E. coli*-derived human GM-CSF, IFN-γ, and mouse IL-10 were supplied by Schering-Plough Research Institute (SPRI), New Jersey. The specific biological activity of these preparations were $2.3 \times 10^7$ units/mg for hIL-10 and $1.6 \times 10^7$ units/mg for mIL-10 as measured by the MC/9 proliferation assay (see below). Recombinant hIL-6 was purchased from Genzyme (Cambridge, Mass.), though other commercial suppliers include, e.g., PeproTech, Inc., Rocky Hill, N.J. Monoclonal antibodies to IL-10 and IL-5 were provided by J. Abrams (DNAX, Palo Alto, Calif.), see Abrams, et al. (1992) *Immunol. Rev.* 127:5–24.

Iodination of hIL-10.

Purified hIL-10 protein was labeled using the Enzymobead radioiodination reagent (Bio-Rad, Richmond, Calif.), which is an immobilized preparation of lactoperoxidase and glucose oxidase, following the manufacturer's protocols. The purified protein was passed through a PD-10 column (Pharmacia LKB Biotechnology, Piscataway, N.J.) to remove free label. Additional samples were also custom-iodinated following the lactoperoxidase method (NEN Research Products, Boston, Mass.). Specific radioactivity obtained was in the range of 100–180 μCi/μg hIL-10. The iodinated material was then passed through a 120 ml Sephadex G-75 column (Pharmacia LKB) with 1.1 ml fractions collected in phosphate-buffered saline (PBS). TCA precipitation was performed by incubating aliquots of the fractions in 10% trichloroacetic acid for 1 hour at 4° C. Pellets formed after centrifugation were then counted in Clinigamma counter (Pharmacia LKB).

MC/9 Proliferation Assay.

Biological activity of hIL-10 was determined using a calorimetric MTT dye-reduction assay. See, e.g., Tada, et al. (1986) *J. Immun. Meth.* 93:157–165; and Mosmann (1983) *J. Immun. Meth.* 65:55–63, which are incorporated herein by reference. Briefly, five thousand MC/9 cells per well in 100 μl media containing 100 U mIL-4/ml in a 96 microtiter well were treated for 48 hours with varying amounts of human IL-10. The hIL-10 standard was used at a maximum of 200 units/100 μl and two-fold serially diluted. Twenty-five microliters of 5 mg/ml MTT was added and incubated for 3 to 5 hours. The cells were then detergent-lysed in 10% SDS with 10 mM HCl and the plates were read for absorbance at 570 nm.

Binding Assays and Scatchard Analysis.

Approximately $5 \times 10^6$ cells for each cell line tested were pelleted by centrifugation at 200×g for 10 min., washed in PBS, and resuspended in 200 μl binding buffer (PBS, 10% fetal calf serum, 0.1% $NaN_3$) containing iodinated hIL-10 at a concentration of 100–500 pM. After incubation at 4° C. for two hours in a rotary mixer, the cells were centrifuged at 200×g for 10 minutes, resuspended in 100 μl binding buffer without labeled hIL-10, layered over 200 μl of a 1:1 mixture of dibutyl- and dioctyl-phthalate oils in elongated microcentrifuge tubes, centrifuged at 400×g for 5 minutes at 4° C., and quick frozen in liquid nitrogen. The cell pellets were then cut and counted in a Clinigamma 1272 counter (Pharmacia LKB). Non-specific binding was determined by performing the binding in the presence of 500 to 1000-fold molar excess unlabeled hIL-10. For saturation binding experiments, two-fold serial dilutions of approximately 600 pM solution of iodinated hIL-10 were used, with a parallel series done to determine non-specific binding.

Scatchard analysis was performed on the data points obtained using the EBDA Program (Elsevier-Biosoft, Cambridge, U.K.). Antibody inhibition was performed under the above binding conditions but with the addition of a 100-fold molar excess of each of the indicated monoclonal antibodies. Cytokine specificity was determined under similar conditions but with the addition of 500-fold molar excess of the cytokines indicated.

Chemical cross-linking.

Cross-linking may be done using BS3, Sulfo-EGS, or EDC following manufacturer's instructions, Pierce, Rockford, Ill.

Alternatively, about $5 \times 10^6$ cells were incubated for 4 hours at 4° C. in 400 μl of binding medium consisting of RPMI-1640, 50 mM HEPES, 0.02% $NaN_3$, 0.5% BSA, and 1 nM $^{125}$I-hIL-10 with or without 1000 nM unlabeled hIL-10. The cells were washed 2 times with RPMI-1640 and then resuspended in 1 ml of RPMI-1640. To the cell suspension, 6 μl of dimethyl sulfoxide containing 10 μg/ml disuccinimidyl suberate (DSS) was added and the cells were incubated for 20 minutes on ice. The reaction was stopped by addition of 50 μl 1M Tris-HCl (pH 7.5). The cells were collected by centrifugation and were then lysed by adding 30 μl of the lysis buffer containing the following: Tris-HCl (pH 7.5), 140 mM NaCl, 2 mM EDTA, 10 mg/ml leupeptin, 2 mM iodoacetamide, 2 mM O-phenanthroline, and 1% Triton X-100. The lysates were centrifuged at 10,000×g for 10 min at 4° C., and 10 μl of the supernatants were electrophoresed on a 7.5% gradient polyacrylamide gel (Daiichi Chemicals Co., Tokyo) in the presence of SDS according to Laemmli (1970) *Nature* 227:680–685, under reducing conditions.

COS7 transfections.

5 μg of the indicated plasmid DNA was mixed with $5 \times 10^6$ COS7 cells in 250 μl of Dulbecco's Modified Eagle Media with 10% Fetal Bovine Serum and antibiotics in an electroporation cuvette (Bio-Rad, Richmond, Calif.). The cells were elctroporated using a Bio-Rad Gene Pulser using 0.20 kV with the capacitance set at 960 μF and the resistance at 200 ohms. After 10 min at room temperature, the cells were put in 10 cm dishes with 10 ml complete media, and allowed to attach. After an overnight incubation at 37° C., the media was replaced with the same media but without serum. Two days later, the cells were detached from the plates by incubating in a phosphate buffered saline with 4 mM EDTA and 0.03% $NaN_3$, harvested, and used for binding assays. Approximately $1 \times 10^6$ cells were used for each binding determination.

EXAMPLE 2

Preparation of Human and Mouse Fusion Proteins of IL-10 with FLAG Sequences

Nucleic acid constructs encoding fusion proteins as described in FIG. 1 were prepared by standard molecular biology techniques. The FLAG sequence is recognized by commercially available antibodies (IBI-Kodak, Rochester, N.Y.) and does not interfere significantly with the association of the IL-10 fusion protein with the binding protein, as measured in biological assays for IL-10 activity.

EXAMPLE 3

Preparation of a cDNA Library from Appropriate Cell Sources cDNA libraries were constructed using standard techniques from cell lines which are sensitive to IL-10. See SuperScript Plasmid System for cDNA Systems and Plasmid Cloning, Life Technologies, BRL, Gaithersburg, Md. The BJAB B cell line from human was used, and the mouse MC/9 mast cell or J774 macrophage cell lines were used.

EXAMPLE 4

Figure 3:
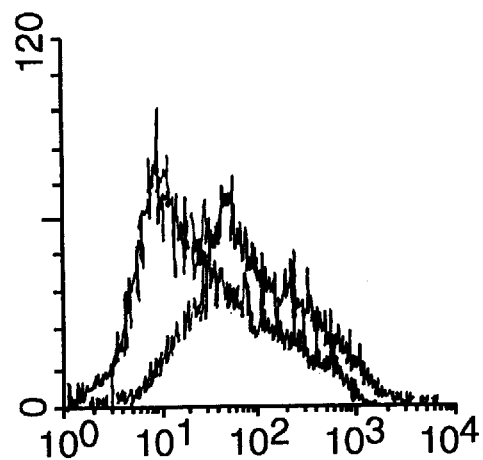
FIG. 3 shows FACS analysis of mIL-10 receptor expression on COS7 cells transfected with an mIL-10 receptor cDNA clone (m3.14). Binding of FLAG-mIL-10 (dark) is competed by a 30–100-fold excess of mIL-10 (light), which is equivalent to background.

Enrichment of Transformed Cells Expressing Elevated Amounts of IL-10 Binding Protein Cells transfected with the cDNA libraries were subjected to FACS sorting using biotinylated fluorescent FLAG antibodies as markers. After exposing transformed cells to the antibodies, phycoerythrin-streptavidin (PE-streptavidin) was added. The marked cells were then analyzed by FACS to collect the 3–5% of cells expressing the greatest amount of IL-10 binding. See FIG. 2. Selected cells were then used to make cDNA libraries. Cells were subjected to three cycles of enrichment. FIGS. 2 and 3 show that IL-10 can compete with the FLAG-IL-10 binding.

Alternatively, cells which expressed IL-10 binding were selected by affinity purification, i.e., panning, on plates coated with anti-FLAG antibodies. Cells were subjected to multiple cycles of the panning procedure, and those cells isolated and their exogenous vector inserts isolated and characterized.

EXAMPLE 5

Characterization of the IL-10 Binding Protein Encoding Nucleic Acid

The isolated inserts from both the human and mouse cDNA sources were further characterized by sequencing by standard methods.

Figure 4:
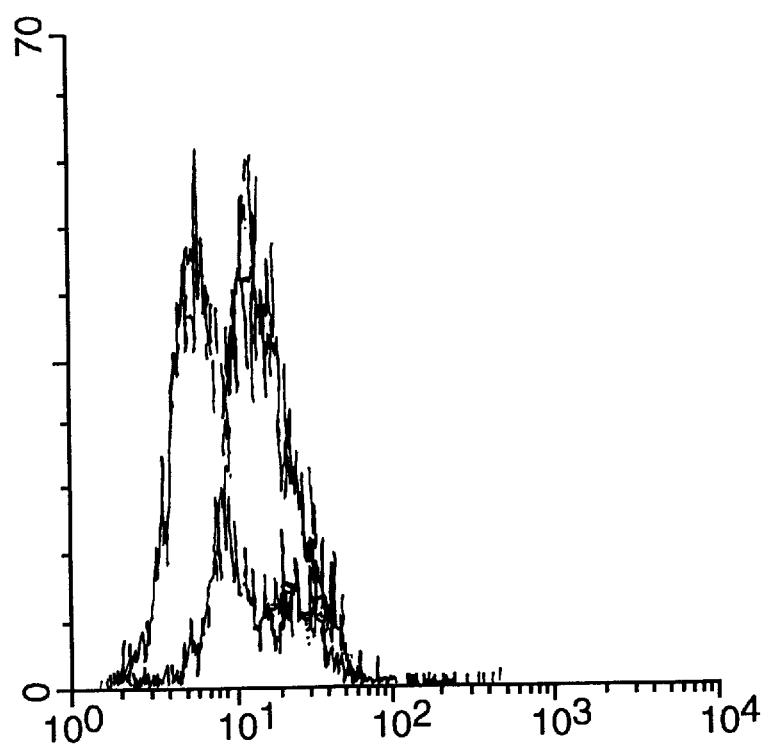
FIG. 4 shows FACS analysis of hIL-10 receptor expressed on a human B cell line BJAB. Cells in late log phase were diluted in fresh medium and assessed for hIL-10 receptor expression 12–16 hr later. Binding of FLAG-mIL-10 (right profile) is competed by a 30–100-fold excess of mIL-10 (left profile), which is equivalent to background.
Figure 5A:
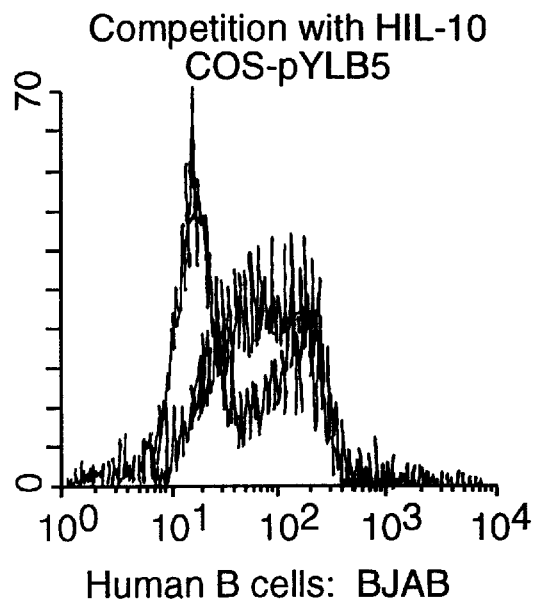
FIGS. 5A–5B show FACS analysis of hIL-10 receptor expression on COS7 cells transfected with an hIL-10 receptor cDNA clone (YLB5). Panel labeled "COMPETITION WITH HIL-10" shows binding of FLAG-hIL-10 (dark), or with a 30–100-fold excess of hIL-10 (light), which competes the signal to background levels. Panel labeled "COMPETITION WITH mIL-10" shows binding of FLAG-hIL-10 is not competed by a 30–100-fold excess of mIL-10.
Figure 5B:
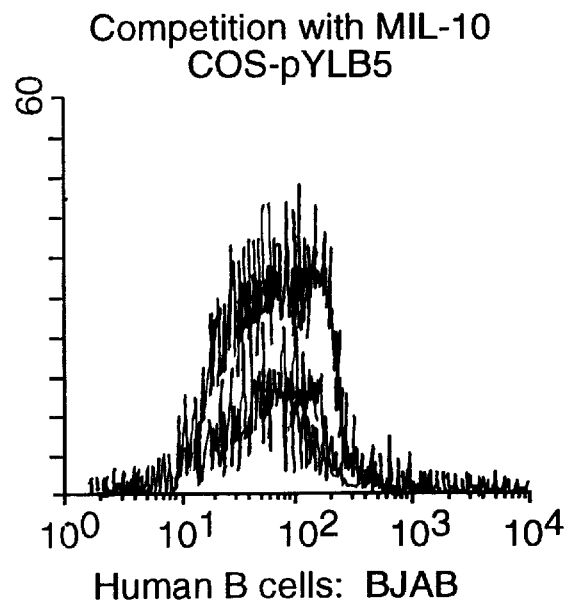

FIGS. 2, 3, 4, and 5 show that most of the cells after selection have a higher fluorescence intensity. Moreover, the binding signal is competed by a 50× excess of IL-10. FIG. 3 shows mouse cells. FIG. 4 shows cells transfected with the m3.14 mouse clone and expressing the resulting receptor. These cells exhibit fluorescence intensity which is competed by a 50× excess of IL-10 (left profile). FIG. 5 shows cells transfected with pYLB5 which was the original isolate of the human cDNA clone obtained through multiple cycles of enrichment. This clone was used to isolate the pSW8.1 clone from the original BJAB human cell cDNA library.

EXAMPLE 6

Lactoperoxidase Labeling Method Retains the Biological Activity of hIL-10

Purified CHO-derived hIL-10 was iodinated to high specific activity (100 to 200 $\mu$Ci/$\mu$g protein) using the lactoperoxidase method. Initial attempts to label CHO-derived hIL-10 with the IODO-GEN reagent (Pierce, Rockford, Ill.) resulted in protein of insufficient specific activity to be used in receptor characterization. The lactoperoxidase method yielded iodinated hIL-10 with a specific activity approximately five-fold higher than that obtained with IODO-GEN.

Figure 6:
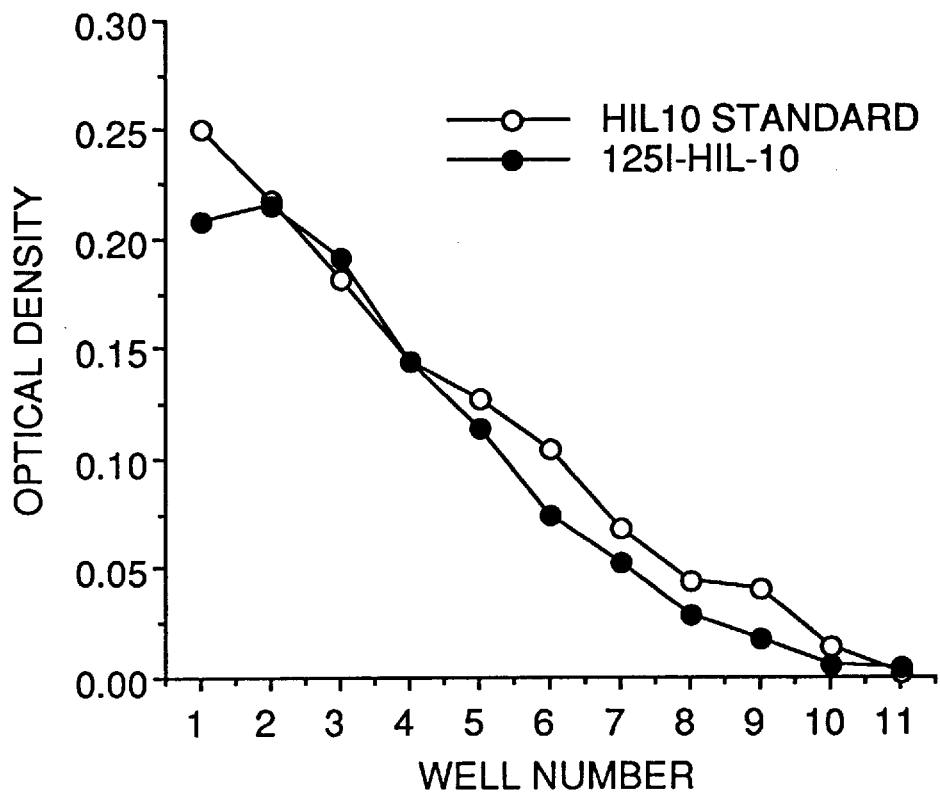
FIG. 6 shows an MC/9 proliferation assay of radioiodinated hIL-10. Unfractionated hIL-10 at a concentration of 50 ng/ml was tested for its proliferative effect on MC/9 cells using a colorimetric MTT assay. Unlabelled hIL-10, used also at 50 ng/ml at the highest concentration, was examined in parallel. The samples were two-fold serially diluted for assay.

In order to determine if the high specific activity labeled hIL-10 was biologically active, samples were examined for their ability to induce MC/9 cell proliferation by the method of Thompson-Snipes, et al. (1991) *J. Exp. Med.* 173:507–510. FIG. 6 shows the assay result with 50 ng/ml of iodinated hIL-10 in comparison with the same concentration of unlabeled protein. The estimated activity for the sample was $7.48 \times 10^2$ units/ml compared to $1.16 \times 10^3$ units/ml for the standard, giving a retention of 64% biological activity for this sample. Repetition of biological assay results with other samples of iodinated hIL-10 indicated routinely greater than 50% biological activity retention.

EXAMPLE 7

The Active Form of Radiolabeled hIL-10 Appears to be a Dimer

Figure 7A:
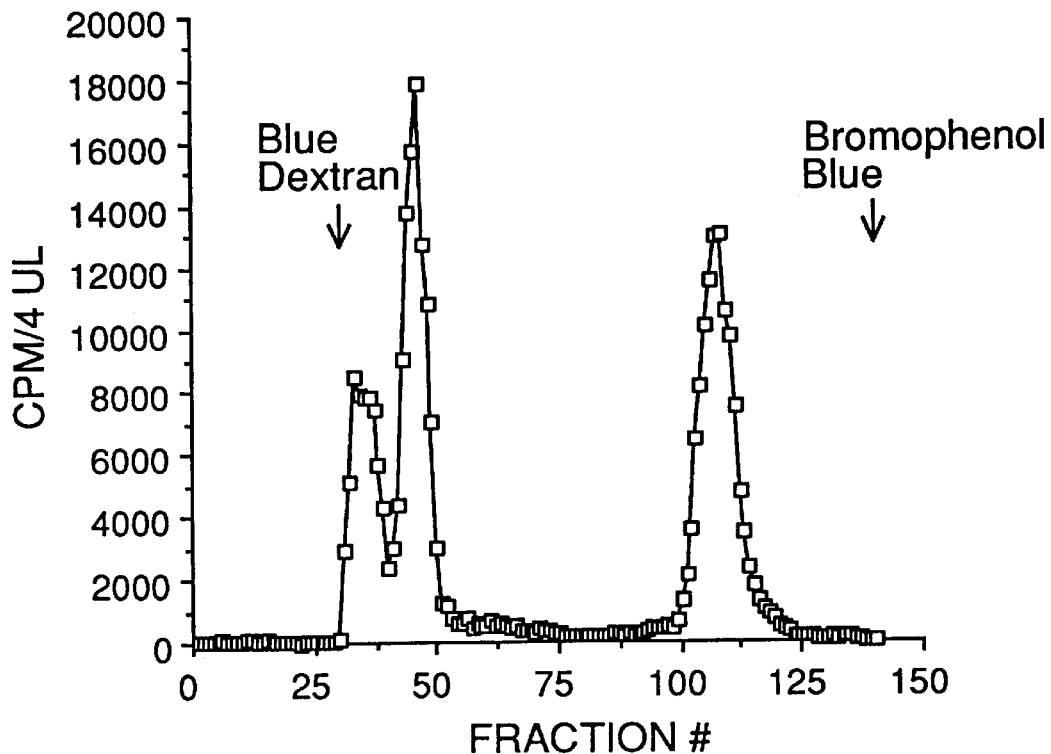
FIGS. 7A–7C show gel filtration chromatography of radioactively labelled hIL-10.
Figure 7B:
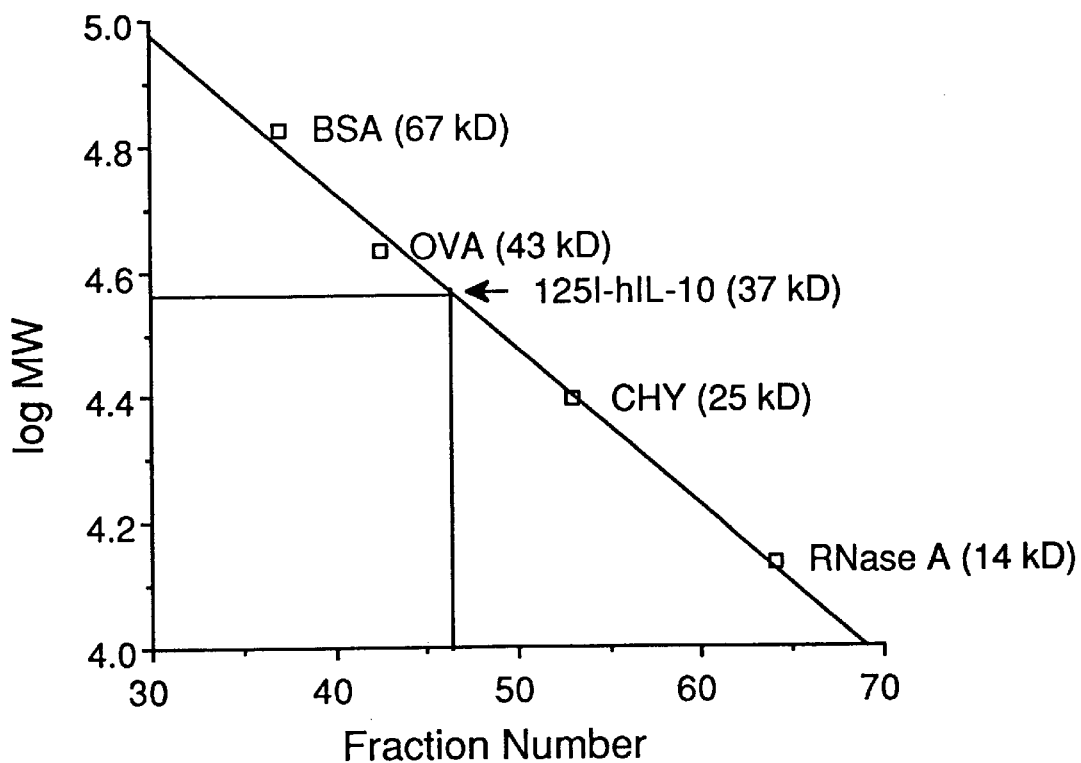
Figure 7C:
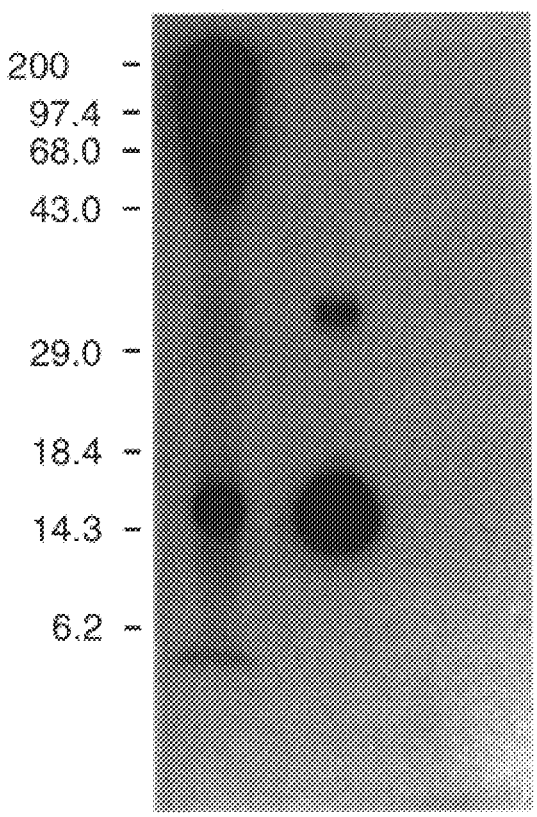

The labeled protein mixture, when passed through a Sephadex G-75 gel-filtration column, was resolved into three distinct species (FIG. 7A). This fractionation was found to be necessary to reduce background binding to target cells. The largest species was a high molecular weight form which elutes with the excluded volume. The smallest species eluted between the lowest molecular weight standard (13.7 kDa) and the dye marker Bromophenol Blue. Sizing with molecular weight standards showed the second species to be approximately 37 kDa (FIG. 7B), consistent with the predicted molecular weight for a hIL-10 dimer. Polyacrylamide gel electrophoresis of the three species in the presence of SDS (FIG. 7C) revealed that the high molecular weight form ran as an aggregate between 43 kDa and 200 kDa. The second species migrated under these conditions at approximately 18 kDa, while the third species was not observed at all. The radioactivity associated with the largest and the second species was TCA precipitable while that associated with the small species was not.

EXAMPLE 8

Radioiodinated hIL-10 Binds Specifically to its Cellular Receptors

Figure 8:
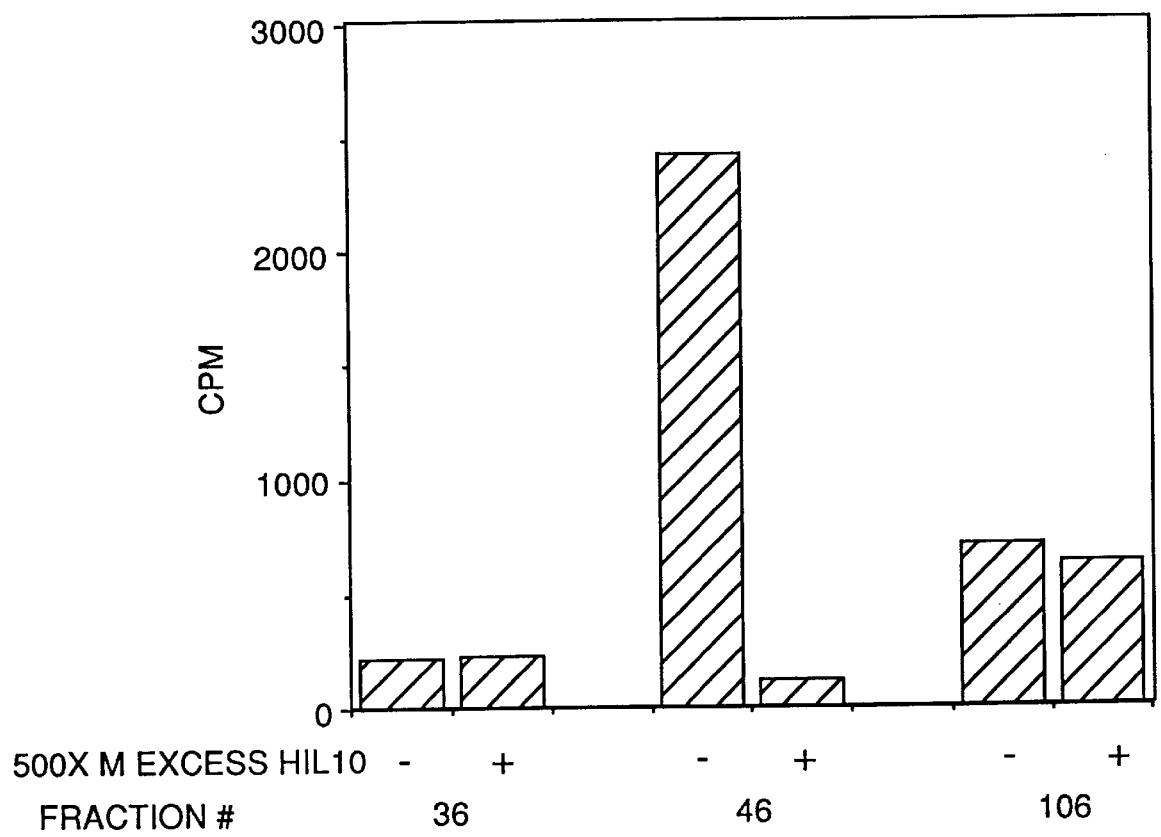
FIG. 8 shows radioiodinated hIL-10 fractions in MC/9 cell binding assays. Duplicate aliquots of the fractions obtained in FIG. 6 were tested for binding to MC/9 cells in the presence or absence of a 500-fold molar excess of unlabeled hIL-10. The concentration of iodinated hIL-10 in the assay was 100 pM.

Based on the observation that the radioiodinated hIL-10 was biologically active, fractionated samples were tested for their ability to bind specifically to candidate cell lines. MC/9 cells respond to hIL-10 by proliferation, so they were first used to determine the binding specificity of hIL-10. FIG. 8 shows that when the three species fractionated from the G-75 column were tested for binding to MC/9 cells, the 37 kDa species, but not the other two, was able to bind to a high degree; moreover, a 500-fold molar excess of unlabeled IL-10 protein could block greater than 90% of the labeled IL-10 binding.

Figure 9:
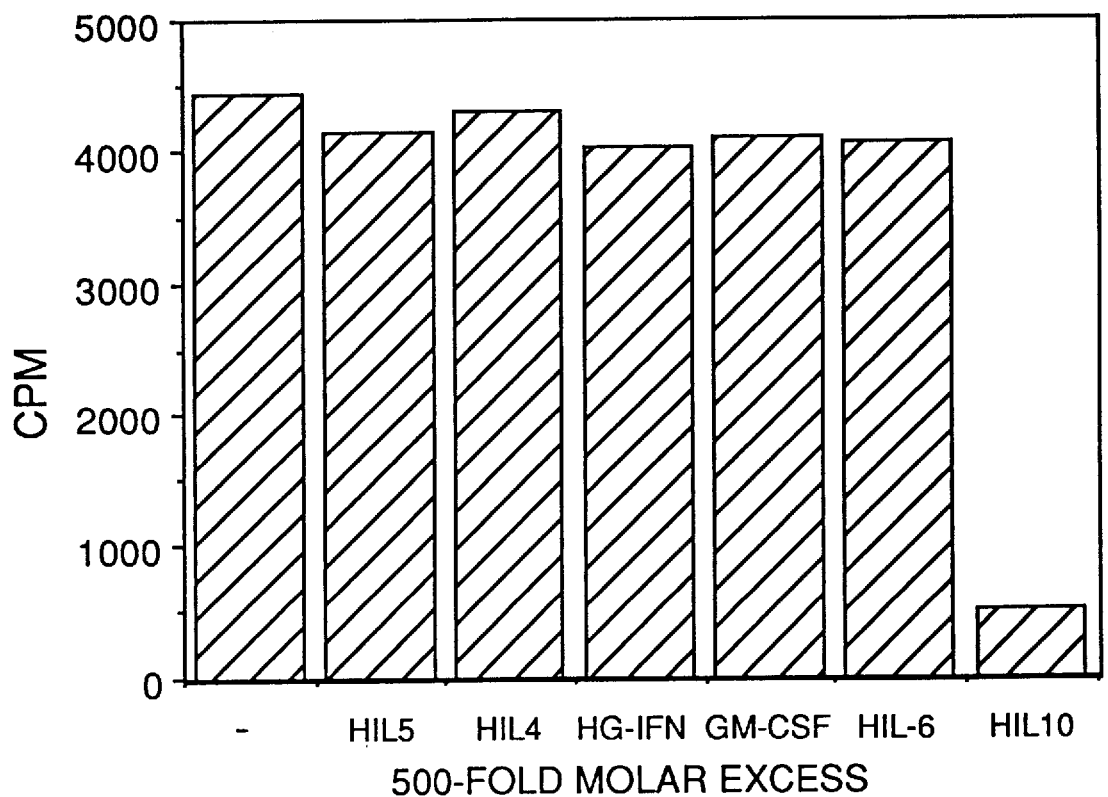
FIG. 9 shows a binding competition assay. Radioiodinated hIL-10 at a concentration of 150 pM was tested for binding to TF-1 cells in the absence or presence of 500-fold molar excess of unlabeled cytokine. Radioactivity bound was determined after washing and pelleting the cells.
Figure 10:
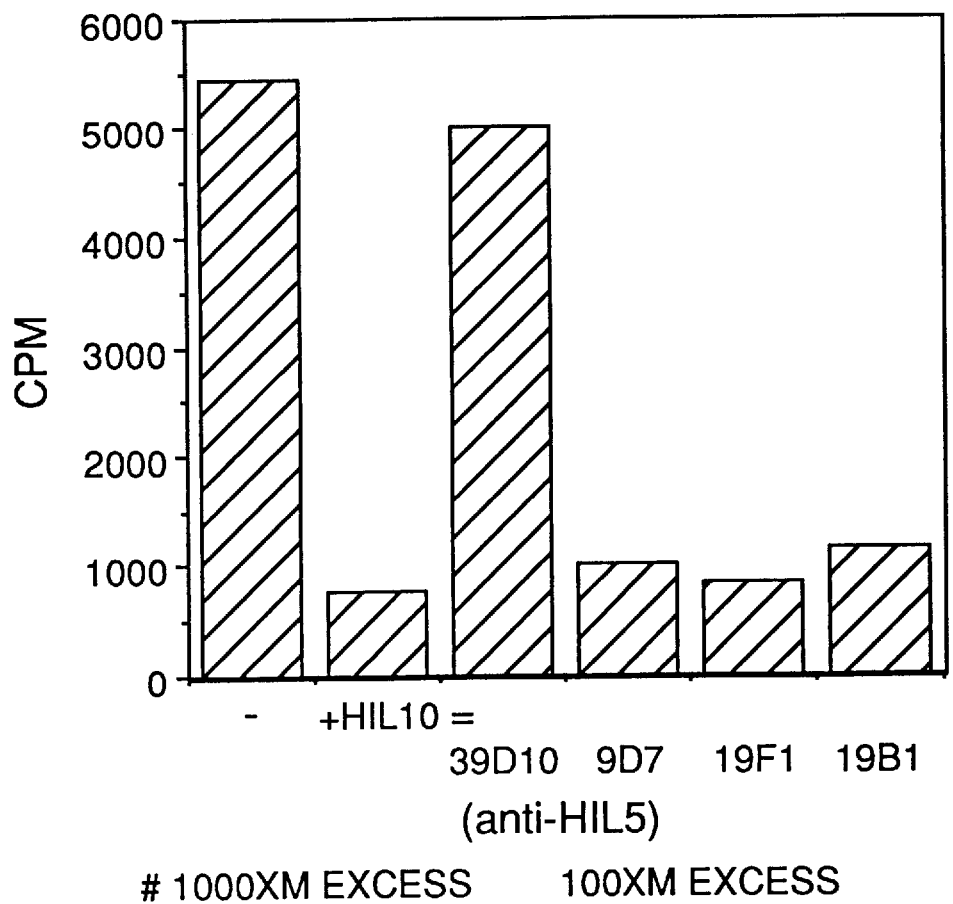
FIG. 10 shows monoclonal antibody inhibition of radioiodinated hIL-10 binding to TF-1 cells. The iodinated hIL-10 at 150 pM was tested for binding to TF-1 cells in the presence or absence of 500 fold molar excess of unlabeled hIL-10 or 100 fold molar excess of purified anti-hIL-5 monoclonal antibody 39D10 or anti-hIL-10 monoclonal antibodies 9D7, 19F1, and 19B1.

In order to ascertain the specificity of hIL-10 binding to its receptor, other cytokines, as well as monoclonal antibodies to hIL-10, were tested for their ability to inhibit the binding of iodinated hIL-10 to its cell surface receptor. FIG. 9 shows that excess hIL-10 was capable of competing with labeled hIL-10 in binding to TF-1 cells. In contrast, hIL-5, hIL-4, IFN-$\gamma$, GM-CSF, and hIL-6 were ineffective in competition. In order to further demonstrate that the binding of hIL-10 to TF-1 cells was specific, monoclonal antibodies to hIL-10 and hIL-5 were examined for their ability to block binding of iodinated hIL-10 to its receptor. FIG. 10 shows that neutralizing monoclonal antibodies generated against hIL-10 were capable of inhibiting the binding of labeled hIL-10 to TF-1 cells, while an anti-human IL-5 monoclonal antibody was unable to block binding of labeled IL-10 as expected.

Figure 11A:
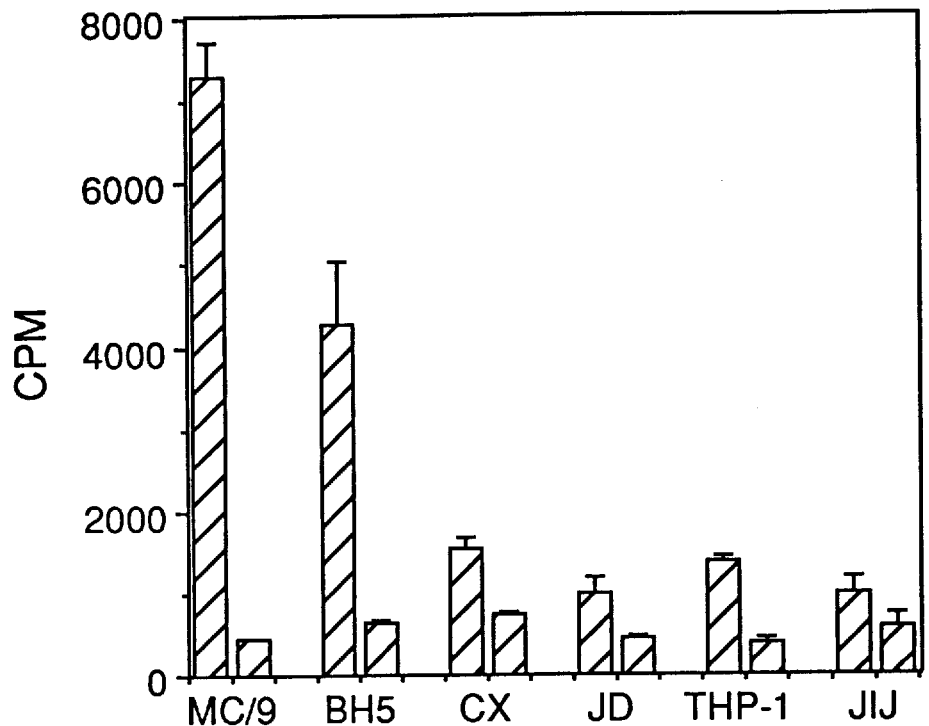
FIGS. 11A–11B show binding of radiolabeled hIL-10 to different cell lines. Approximately $5 \times 10^6$ cells were used for each sample.
Figure 11B:
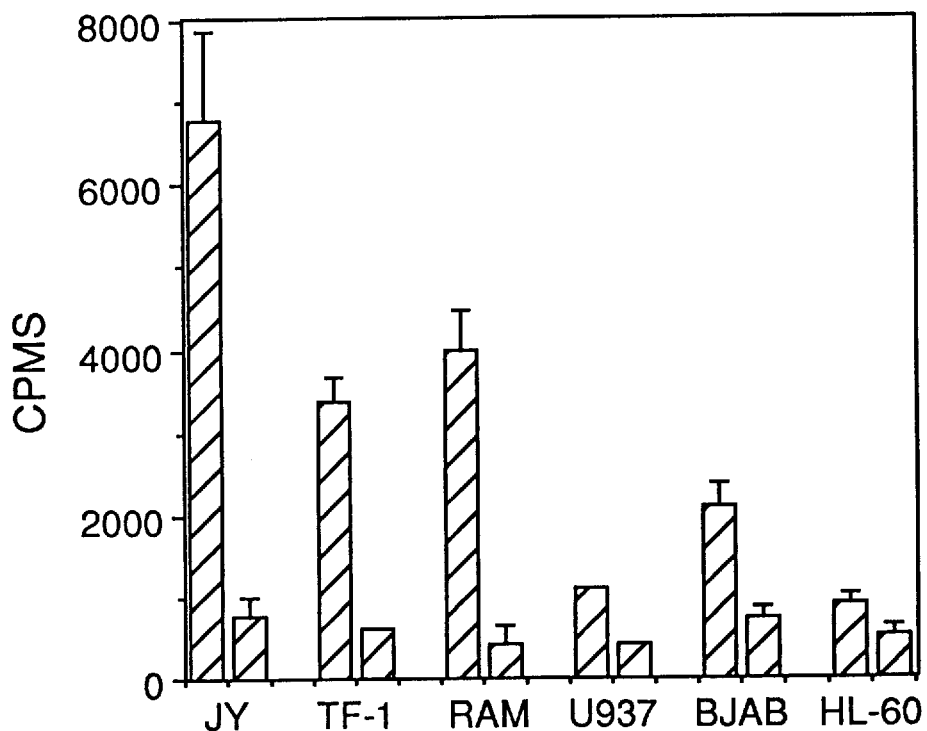

Binding assays with a number of different cell lines indicated that hIL-10 was able to bind to most of these lines to varying extents (FIGS. 11A–11B). The highest degree of binding was seen with the mouse mast cell line MC/9 and the human B-lymphoma line JY. TF-1 (a human erythroleukemia line) as well as Ramos and BH5 (human B-lymphoma lines) show a reduced level of binding relative to JY and MC/9 . Human IL-10 binds to the other cell lines examined at relatively low levels. A binding assay with WEHI 265.1, a mouse monocytic cell line, also shows a relatively low level of binding.

EXAMPLE 9

Human IL-10 Binds to Cellular Receptors with High Affinities

Figure 12A:
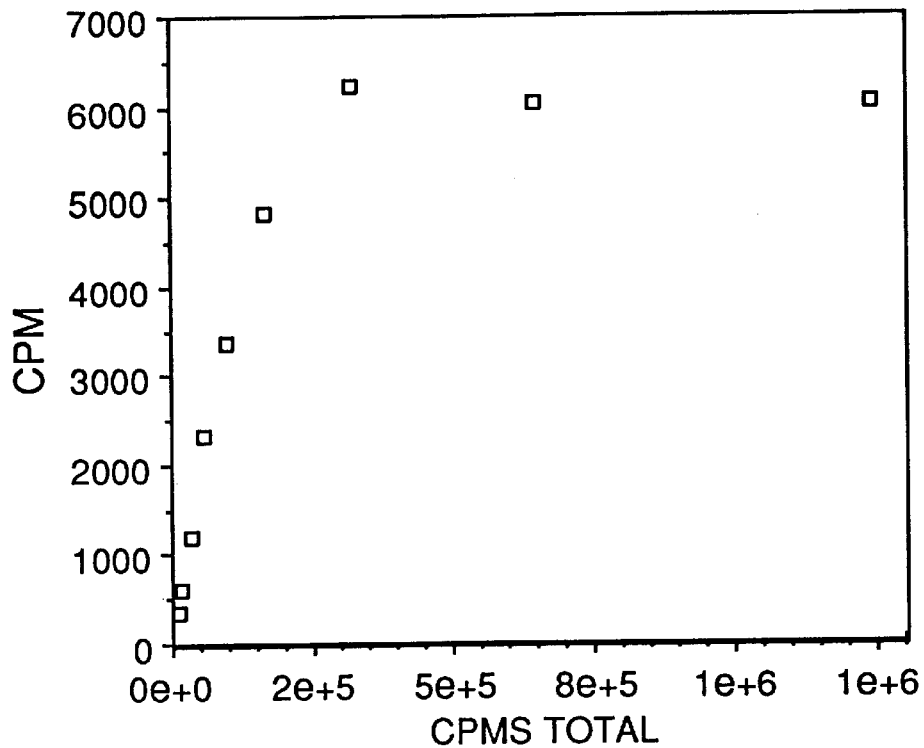
FIGS. 12A–12B show saturation binding of MC/9 cells with radioactive hIL-10.
Figure 12B:
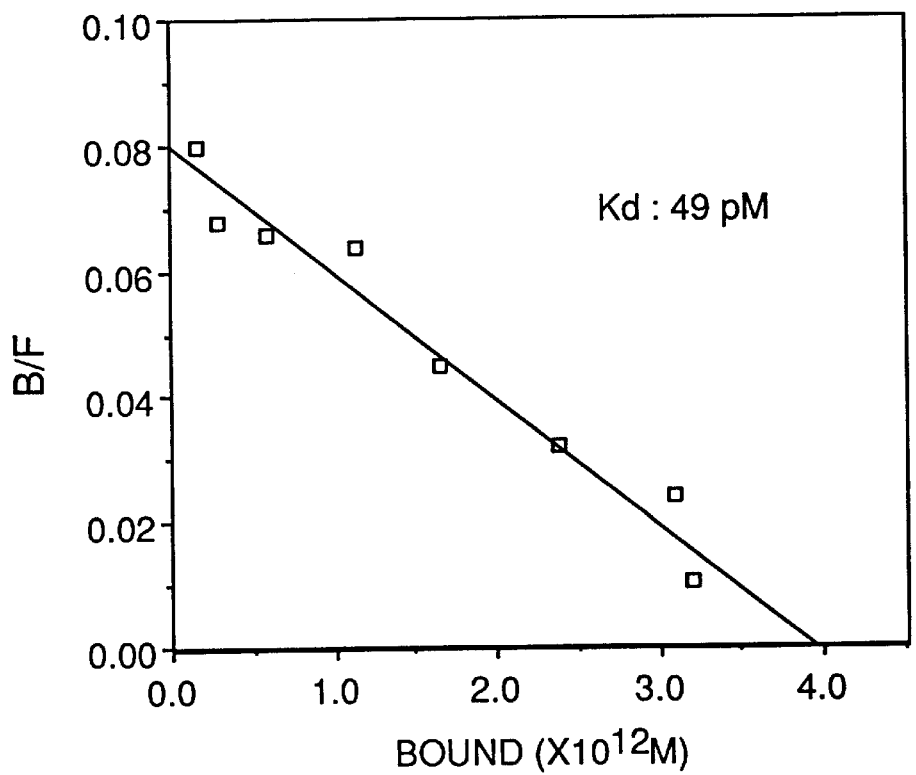
Figure 13A:
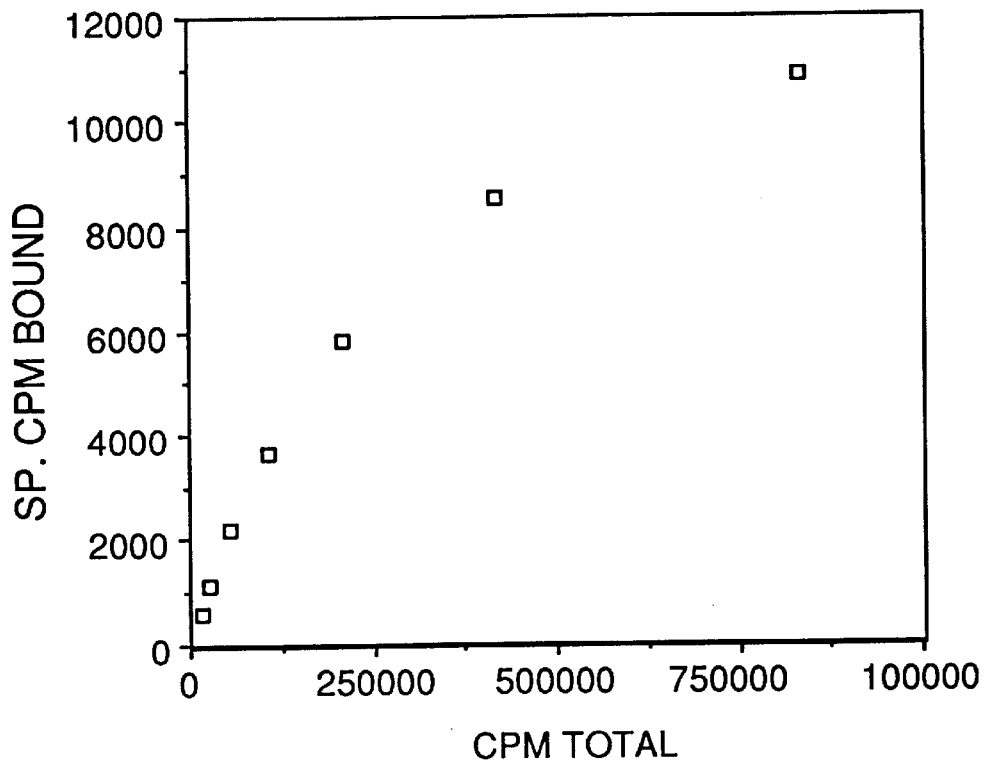
FIGS. 13A–13B show saturation binding of JY cells with fractionated radioactive hIL-10.
Figure 13B:
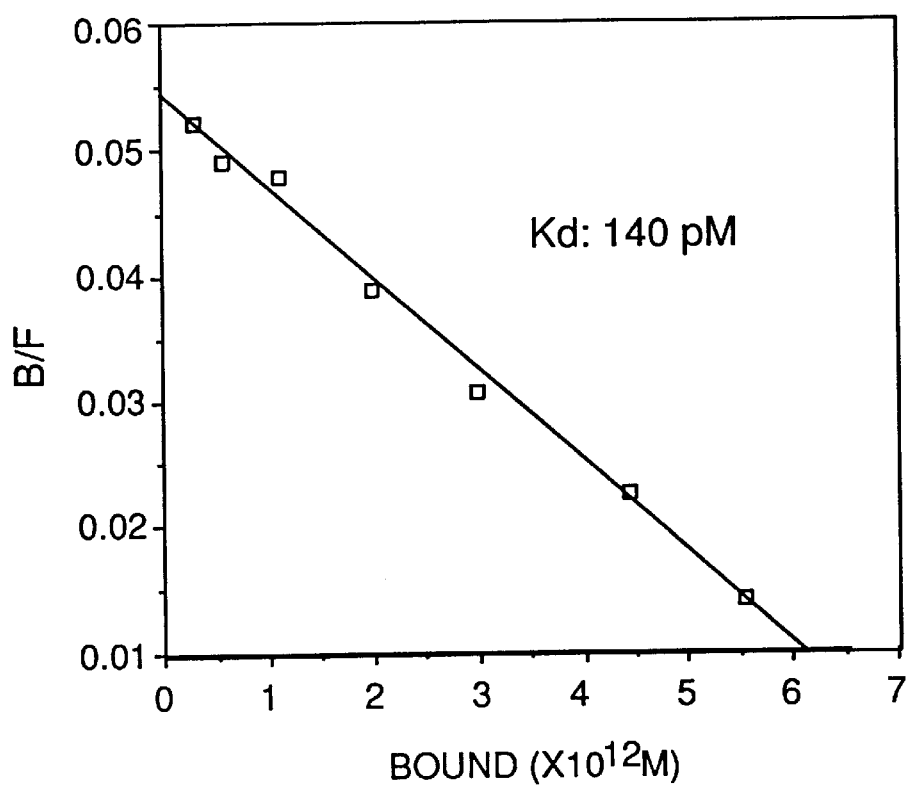

After demonstrating the specific binding of fractionated, iodinated hIL-10 to target cell lines, and the retention of biological activity of this labeled protein, it was decided to determine the binding affinity and estimate the number of binding sites/receptors per cell. Typical saturation binding curves with JY and MC/9 cells are shown in FIGS. 12A and 13A, respectively. Maximal binding occurs at approximately 300 to 400 pM of labeled hIL-10 for both cell lines. Scatchard analyses of representative binding data (FIGS. 12B for JY and 13B for MC/9 ) provided linear graphs with slopes yielding a Kd of approximately 150 pM for the JY cell line and 49 pM for the MC/9 line. Bmax values obtained, which represented the maximal concentration of ligand bound to cells, were 4.0 pM and 7.5 pM for MC/9 and JY cells, respectively. Assuming that one hIL-10 dimer ligand molecule binds one receptor, these results provide an estimate of approximately 100 unoccupied receptors per cell for MC/9 and 180 unoccupied receptors per cell for JY. From several independent experiments, the human IL-10 binding affinity for JY and MC/9 cells was approximately 50 to 170 pM, with between 100 and 300 unoccupied receptors per cell.

EXAMPLE 10

Figure 14A:
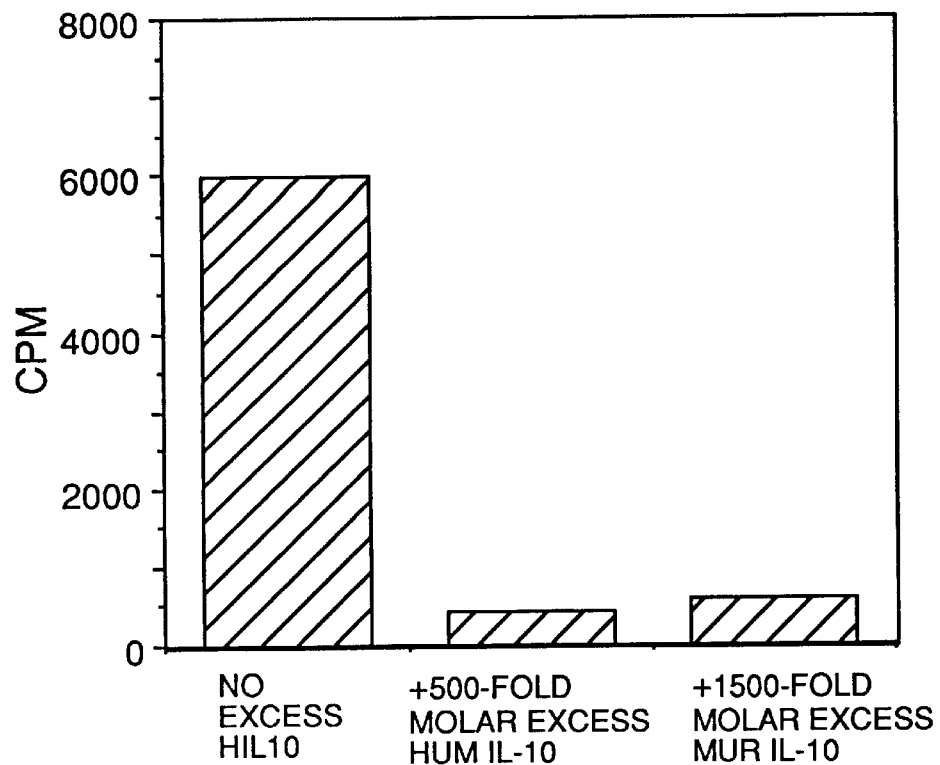
FIGS. 14A–14B show human or mouse IL-10 competition with radioiodinated hIL-10 binding to MC/9 or JY cells.
Figure 14B:
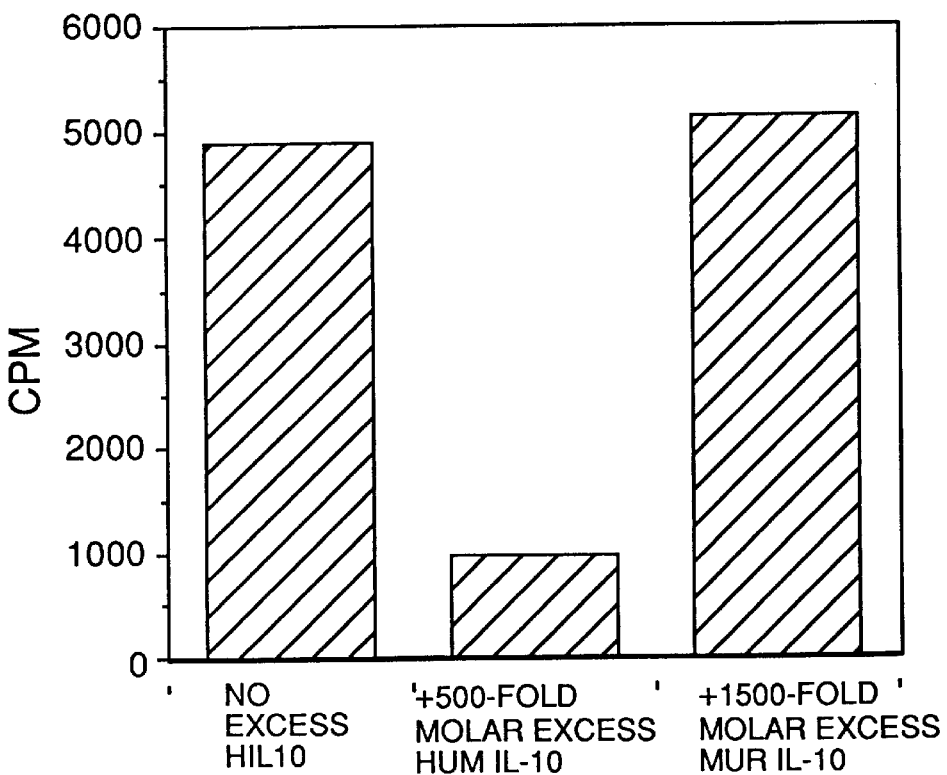

Mouse IL-10 Receptor Binding Appears to be Species-Specific whereas Human IL-10 Receptor Binding is Not In order to examine the species-specificity of receptor binding, the ability of mouse and human IL-10 to compete with labeled human IL-10 for binding to mouse and human cell lines was examined. FIGS. 14A–14B show the results of such competition experiments. Because the specific biological activity of E. coli-derived murine IL-10 was 60–70% of human IL-10, as determined by the MC/9 biological assay, the concentrations of human and murine IL-10 in the competition experiments were adjusted accordingly. FIG. 14A shows that both mouse and human IL-10 were able to block the binding of labeled hIL-10 to the mouse MC/9 line. In contrast, FIG. 14B shows that human IL-10, but not mouse IL-10, is able to successfully compete with the binding of labeled hIL-10 to the human B lymphoma line JY.

EXAMPLE 11

Multiple Complexes were Found after Chemical Cross-Linking of Radiolabeled hIL-10 to its Receptors To characterize the receptor for hIL-10 in JY and MC/9 cells, cells were first incubated with 1 nM $^{125}$I-hIL-10, and then treated with bifunctional linker disuccinimidyl suberate, and analyzed by SDS-PAGE and autoradiography. A few relatively faint and two relatively strong bands were detectable with apparent relative molecular weight (Mr) of 110–180 kDa (minor bands), 98 kDa, and 83 kDa, respectively, with JY cells. The apparent Mrs were estimated based on co-electrophoresed prestained molecular size standards. The 98 kDa and 83 kDa bands were also observed with MC/9 cells although the signals were relatively weaker. Formation of all cross-linked complexes was completely inhibited by the presence of 1000-fold excess amount of unlabeled hIL-10. Upon reevaluation of the migration of the prestained molecular weight standards, the major bands were reassigned molecular weights of about 90–110 kD.

EXAMPLE 12

Specificity of Binding to Human IL-10

Figure 15A:
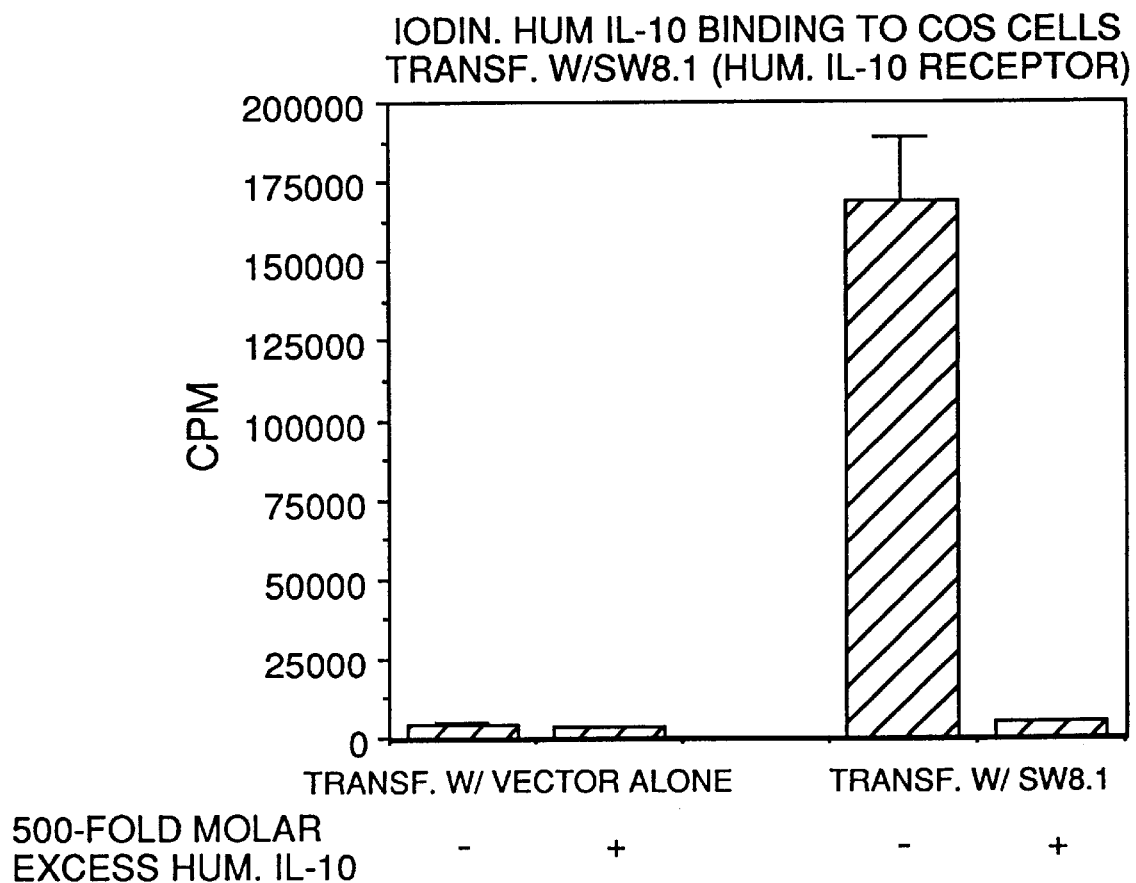
FIGS. 15A–15B show specificity of binding to labeled human IL-10. COS7 cells were transfected with either the human (SW8.1) and mouse (m3.14) cDNA clones, allowed to express the clone for 72 hours, then tested for binding to iodinated human IL-10.
Figure 15B:
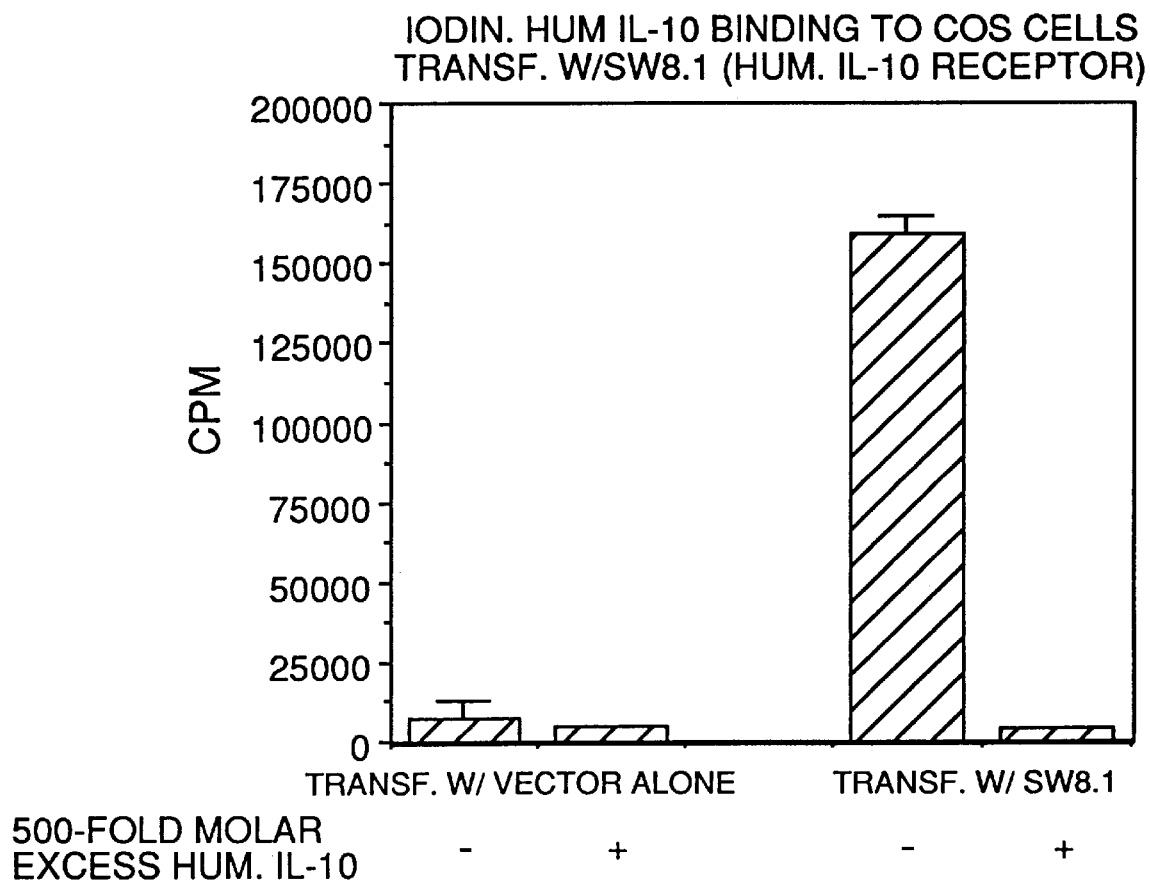
Figure 16A:
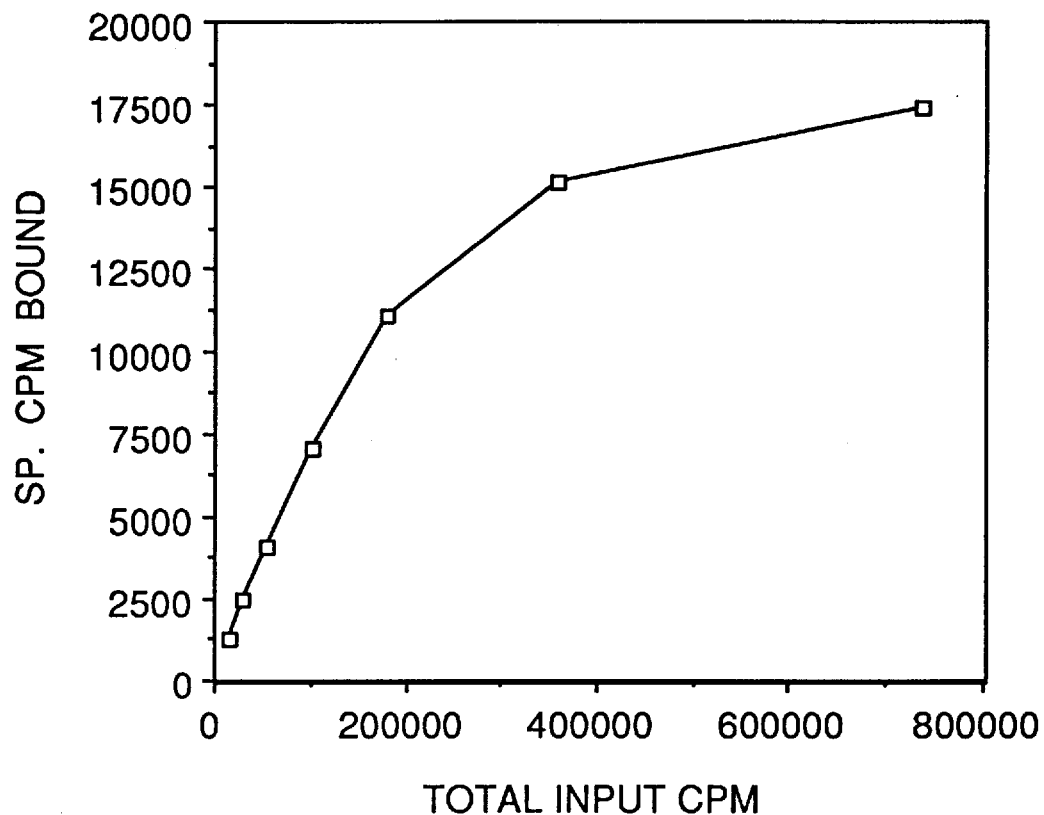
FIGS. 16A–16B show saturation binding of cloned human IL-10 receptor with labeled human IL-10.
Figure 16B:
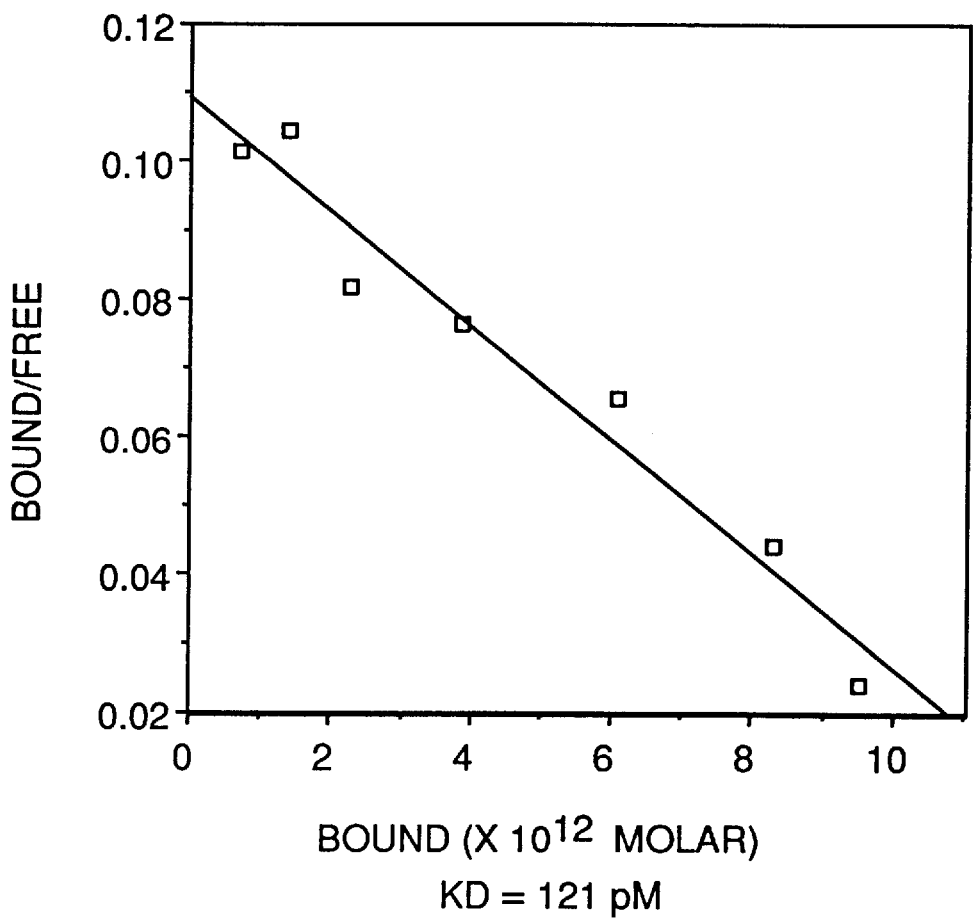
Figure 17A:
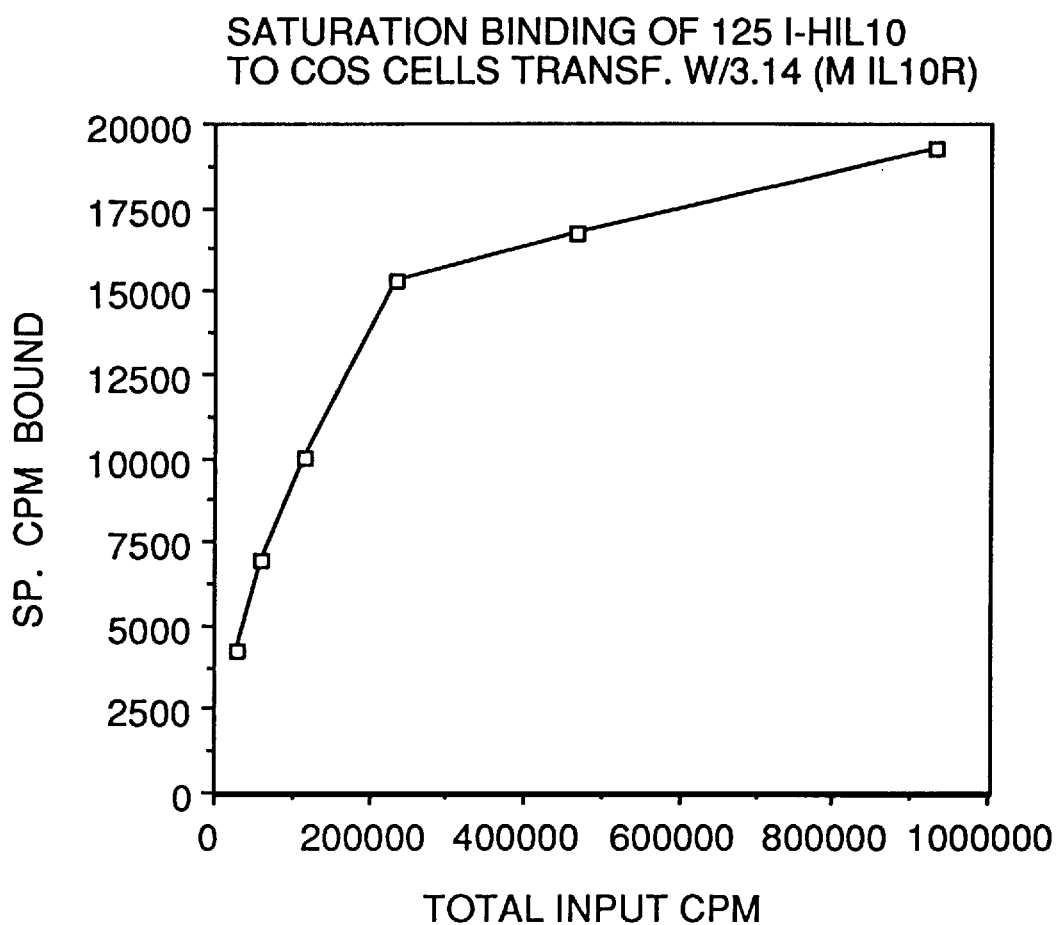
FIGS. 17A–17B show saturation binding of cloned mouse IL-10 receptor with labeled human IL-10.
Figure 17B:
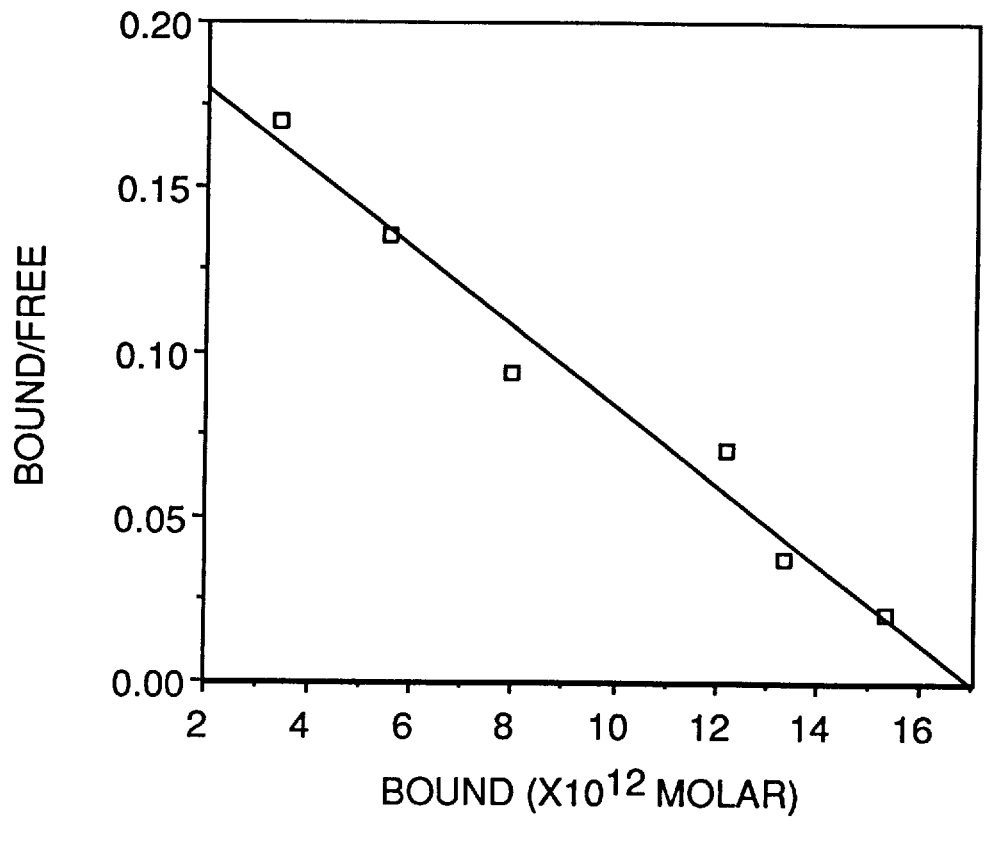

COS7 cells were transfected with the human or mouse cDNA clones, allowed to express the vector for 72 hours, and tested for binding to radioiodinated human IL-10. FIG. 15A shows the human IL-10 receptor and FIG. 15B shows the mouse IL-10 receptor.

These results show that unlike the vector alone, the cloned receptor cDNA is able to confer specific binding ability for human IL-10 on COS cells. Both the human and mouse clones are able to bind human IL-10.

EXAMPLE 13

Scatchard Analysis of Binding of Human IL-10 to the Human or Mouse Receptors

Binding assays were performed as described in the Brief Description of the Drawings section above.

---

What is claimed is:

1. An antibody or antigen binding fragment thereof that specifically binds to a recombinant IL-10 receptor of SEQ ID NO: 2 or 4.

2. The antibody of claim 1, wherein said receptor is mouse or human.

3. The antibody of claim 1, which:
   a) blocks binding of IL-10 to said receptor;
   b) is covalently attached to a toxic moiety; or
   c) is detectably labeled.

4. A cell which produces an antibody of claim 1.

5. The antibody of claim 1, which is a polyclonal antibody.

6. The antibody of claim 1, wherein said receptor has a sequence of at least one polypeptide segment of at least 18 amino acids of SEQ ID NO: 2 or 4.

7. The antibody of claim 1, which is attached to a solid support.

8. The antibody of claim 1, wherein said antibody has a binding affinity measured by a $K_D$ of at least about 300 μM.

9. The antibody of claim 1, wherein said antibody has a binding affinity measured by a $K_D$ of at least about 30 nM.

10. The antibody of claim 1, which binds to:
    a) an extracellular domain of an IL-10R; or
    b) an intracellular domain of an IL-10R.

11. The antigen binding fragment of claim 1 comprising an antigen binding portion of said antibody.

12. A kit comprising:
    a) said antigen binding fragment of claim 11 in a compartment; and
    b) instructions for use.

13. The antigen binding fragment of claim 11, which is separated from other proteins by specific binding to IL-10 receptor.

14. A monoclonal antibody which binds to human IL-10 receptor of SEQ ID NO: 2.

15. The antibody of claim 14, which is raised to and specifically binds to an IL-10 receptor immunogen or extracellular domain thereof.

16. The antibody of claim 14, wherein said IL-10 receptor is in an inactive form.

17. An antigen binding fragment comprising an antigen binding portion of the antibody of claim 14.

18. The antigen binding fragment of claim 17, which:
    a) blocks binding of IL-10 to said receptor;
    b) is detectably labeled; or
    c) is attached to a solid support.

19. A cell which produces said antigen binding fragment of claim 17.

20. A composition comprising the purified antigen binding fragment of claim 17 and a pharmaceutically acceptable carrier.

21. The antibody of claim 1 which is raised to and specifically binds to an immunogen selected from the group consisting of:
    a) a recombinant receptor for IL-10; and
    b) an extramembrane fragment of at least 10 amino acids from said receptor.

22. The antibody of claim 21, wherein said immunogen is an extramembrane fragment of at least 16 amino acids from said receptor.

23. A kit comprising:
    a) said antigen binding fragment of claim 17 in a compartment; and
    b) instructions for use.

24. A method of making the antibody of claim 1, comprising immunizing a mammal with a polypeptide of SEQ ID NO: 2 or 4, and collecting said antibody.

25. A method of making said monoclonal antibody of claim 14, comprising culturing a hybridoma making said antibody in a culture medium.

* * * * *